United States Patent
Superak

(10) Patent No.: US 8,669,413 B2
(45) Date of Patent: Mar. 11, 2014

(54) BREEDING AND SELECTION FOR RESISTANCE TO MELON SEVERE MOSAIC VIRUS (MESMV)

(75) Inventor: Ted Superak, Davis, CA (US)

(73) Assignee: HM.Clause, Inc., Modesto, CA (US)

(*) Notice: Subject to any disclaimer, the term of this patent is extended or adjusted under 35 U.S.C. 154(b) by 371 days.

(21) Appl. No.: 12/954,712

(22) Filed: Nov. 26, 2010

(65) Prior Publication Data

US 2011/0138493 A1 Jun. 9, 2011

Related U.S. Application Data

(60) Provisional application No. 61/264,584, filed on Nov. 25, 2009.

(51) Int. Cl.
*A01H 1/04* (2006.01)
*A01H 5/08* (2006.01)

(52) U.S. Cl.
USPC ............ 800/265; 800/269; 800/310; 800/309

(58) Field of Classification Search
None
See application file for complete search history.

(56) References Cited

U.S. PATENT DOCUMENTS

| | | | |
|---|---|---|---|
| 5,569,823 A | 10/1996 | Schreier et al. | |
| 5,773,700 A | 6/1998 | Van Grinsven et al. | |
| 5,898,097 A | 4/1999 | Beachy et al. | |
| 5,919,705 A | 7/1999 | De Haan | |
| 6,057,492 A | 5/2000 | De Haan | |
| 7,019,195 B1 | 3/2006 | Heifetz et al. | |
| 2009/0031447 A1 | 1/2009 | Yeh et al. | |

FOREIGN PATENT DOCUMENTS

| | | |
|---|---|---|
| EP | 0426195 B | 10/2001 |
| EP | 0722498 B | 5/2005 |
| IT | RM980526 A1 | 2/2000 |
| WO | WO 94/00582 | 1/1994 |
| WO | WO 94/16550 | 8/1994 |
| WO | WO 98/37223 | 8/1998 |
| WO | WO 02/086146 | 10/2002 |
| WO | WO 2007/080126 | 7/2007 |

OTHER PUBLICATIONS

Paris et al. (Ann. appl. Biol. (2000), 136:209-214).*
Giampan et al. (Scientia Horticulturae, 114, (2007), pp. 129-132).*
Ciuffo et al., "A New *Tospovirus* sp. in Cucurbit Crops in Mexico", *Plant Disease*, May 2009, 93(5):467-474.
Turina et al., "A previously unreported *Tospovirus* species isolated from melon crops in Mexico", *Journal of Plant Pathology*, Aug. 2008, 90(2, Supplement), S2.81-S2.465, ICPP 2008 9th International Congress of Plant Pathology, Abstracts of invited and offered papers, p. S2.438.
Adkins et al., "Tospoviruses (Family Bunyaviridae, Genus *Tospovirus*)", University of Florida IFAS Extension, Fact Sheet PP-212, Oct. 2005, pp. 1-5.
English translation of abstract of Italian Patent Application publication No. IT RM980526 (A1), May 8, 1998.

* cited by examiner

*Primary Examiner* — David T Fox
*Assistant Examiner* — Jared Shapiro
(74) *Attorney, Agent, or Firm* — Cooley LLP

(57) ABSTRACT

The invention provides methods of detecting MeSMV; methods of screening plants for resistance or susceptibility to MeSMV; and methods of breeding to produce plants that are resistant to MeSMV; and to the resistant plants produced by such methods.

5 Claims, 9 Drawing Sheets

Melon

SEQUENCE LISTING

```
<160> NUMBER OF SEQ ID NOS: 14

<210> SEQ ID NO 1
<211> LENGTH: 3283
<212> TYPE: DNA
<213> ORGANISM: Melon Severe Mosaic Virus

<400> SEQUENCE: 1
```

-continued

| | |
|---|---|
| agagcaattg tgtcagtttt ataattcata ttcaaccata tcttccttcc tttgcaaagt | 60 |
| taataagaaa atcccctgaa atgagttcaa gttgcttaga ttcgattgtt caatccaaag | 120 |
| cctctgtctg gggcacatcc gtgtctggta aatctattct agacacttac tggatacatg | 180 |
| attatgagac aggcaaacct ttattggaaa cacaacttta ctctgattct aggagcaaaa | 240 |
| gcagtttctg ttatacaaac aaagttgatg atattcctat tgcagatgct gaactggtta | 300 |
| gcgatgccag tgttttctca ttgcttgatg atatcgattt ttctatgacc attgaggagt | 360 |
| cattcataac tgtctctgtc tgttcaaaca cagtaaacac taatggagtg aagcaccagg | 420 |
| gtcatttaaa aataatttca acacagaaac cagtggcatt gaatttcttg gcagaatcgg | 480 |
| accacattct gaaaagattt aacttgaagg agaccgatat tgtccctgaa gaccgtttca | 540 |
| tagctgcagc aaatagagga tctttatcct gtgtcaaaga aataatgtat gagactaaga | 600 |
| caagcaataa ccaagcttat ggcaaggtca atgtcctatc tccaaacaga aattctaatg | 660 |
| aatggattta cactgttaaa cctatgttca atcaaactga aacaaacaac agaactgtga | 720 |
| actcgttggc tattaaatct ttgcttttgt ctgctgtgaa cgacatttcc ccttgttctc | 780 |
| aggtgttttt gaaagctttt actgataaat cttcaagct gtctttctgg ttgagaatcc | 840 |
| caaaagtcct caaacacaca gacttttata aatgcttcaa aataccgaat ggttcttcca | 900 |
| acctttccct aacaataaac tgtatcccaa actacaacaa cattgaaacg gcactgaact | 960 |
| tttctctggt gtctctgaag ccaaaggaac cattgagtgc tcctaaacag ggtaagtttg | 1020 |
| tcatcaactt ctctagttta aagaaccat gctgcaatgt ttttgatctt acttatcccc | 1080 |
| aaagaattgt ccactcactg ctcgaagttc atacatctct tgctaaaaaa ctatcagatt | 1140 |
| ttttacgaga agaagtcatt atatacactt tgaatctgcc agaaactgaa gtgaaaaagc | 1200 |
| tcgatcttgc tggaagaact cttaattaca atgaaagtcc ttctggaaag aagtattttc | 1260 |
| tgtctcaaac cttaaactgc ctccctaaaa actctcagag tttggcttat cttaacagtt | 1320 |
| tccaattctg ttctttgcat gtcgactaca ttagaggcga aatatgtgtt ttaccgactt | 1380 |
| tgtcttcagc ctccagagca aatttgcgat tggacatagc atcaactatg tccaaaagcc | 1440 |
| cttttttgaag tgtaattcat tttccttatt tatgtattat tatttaagta tatgttatat | 1500 |
| ctttgtcttt atttattccg atcaatttat gtgttctatg tttgttatca atgcaatata | 1560 |
| ttagaatatt aagctgtaac ttaggtaagt aactatattg ttaaaacaaa aacacaaaaa | 1620 |
| aatcaaaaaa caaaaaaccc aaaaagatcc ctaacgggac aatattggtc tgtctaatag | 1680 |
| gaaattatgc catttaatta acagacattg agtatcaagt aattagattg tatcagatgg | 1740 |
| ttcaatgatg cagagagtgt gtcaatttat ccacattgct agtgcatgat ttggactaag | 1800 |
| taaagagaat taaaaatata gtgtctgaat gccttaggtt gattttgctt tttgatacac | 1860 |
| agactcatgt attgatcttg ttcaaaggat catatcctac tggtagaaaa cagcatggtg | 1920 |
| tttaaacact acaagtatt ctcagttcc cagtaacttt gatcagttcg ataggtcca | 1980 |
| cacaagttaa gctcaaatgt gtttatctaa tttatcttaa aactgttatg catgatattt | 2040 |
| gaaccaatcc tctgagtgaa gaggtcaaaa agttttttgt tttttggttt ttgttttttat | 2100 |
| tatattttg atttttctgt gttttttgat agttttttaa ttttttgta ttttttgtat | 2160 |
| tttgtatttt gtattttata atttagattt aaaatattat tattttttggt ttatatctta | 2220 |
| gtacatatat tagcttgatt aacacagtta aaacacacaa gaaataacac ttaatgataa | 2280 |
| aacagattaa acttattttt aacacacata tagatacaat acatcattta acaaattaaa | 2340 |
| tctcaaaaac tttgctggtt gaagctttct tcgatccaga aacaccaaag atctcataga | 2400 |

| | |
|---|---|
| tctgcttcaa cccagcttca taatgattca tagccatgtc tcccttgagc ttaggatcac | 2460 |
| atttgctgag gatttgtgca tacatttag cttttctccag ttgatcatta tccatcacat | 2520 |
| agcctttgct tttcaaaaca gtgcaaactt ttccaatagc ttctttagta tcatatttct | 2580 |
| tctggtctat tcccagctcc tgtgatttag catcttgata aacagcaaga acaaggcaaa | 2640 |
| tagcttcata atgcggaatg gaagctagaa gaggcaggct tcctcccaag agacaagcaa | 2700 |
| ttcttgcaga ttttgcatca ttaacatcaa ggctgtaagc catgacgaga gggtgtgatg | 2760 |
| atatcttaac cttaattatt tccaatgcct cgtctttggc agtaaactca atcattttg | 2820 |
| ctcttatcat ggcatctagc ctcctgaaag tcatatcttt tggctctatc tttggttttg | 2880 |
| attttttgat tgtgatccca ttaaaagtaa aatcagcttg tttaacaact ttcattatgc | 2940 |
| tttgcctgtt cttaagaaag gtcaaacatg acatcactgt catgttttg agcttttcta | 3000 |
| catttgcatc aaaaaatgta tcaaattgga aagtagattg gttttgttct tcttcaaatt | 3060 |
| caatttcagc attactgctc aagagcttga tgatattgtc ttttgtaagc ttgactttag | 3120 |
| acattttgca atctaaagag ggttaagaat caggtctgga ttattgctta taagagagaa | 3180 |
| ataacctata cagaggattc tcaacagcac agaagcggtt tatatcttca aaggtaaatg | 3240 |
| aaattaagta ttgctaagga attataatcg acacaattgc tct | 3283 |

<210> SEQ ID NO 2
<211> LENGTH: 1368
<212> TYPE: DNA
<213> ORGANISM: Melon Severe Mosaic Virus

<400> SEQUENCE: 2

| | |
|---|---|
| atgagttcaa gttgcttaga ttcgattgtt caatccaaag cctctgtctg gggcacatcc | 60 |
| gtgtctggta aatctattct agacacttac tggatacatg attatgagac aggcaaacct | 120 |
| ttattggaaa cacaacttta ctctgattct aggagcaaaa gcagtttctg ttatacaaac | 180 |
| aaagttgatg atattcctat tgcagatgct gaactggtta gcgatgccag tgttttctca | 240 |
| ttgcttgatg atatcgattt ttctatgacc attgaggagt cattcataac tgtctctgtc | 300 |
| tgttcaaaca cagtaaacac taatggagtg aagcaccagg tcatttaaa ataatttca | 360 |
| acacagaaac cagtggcatt gaatttcttg gcagaatcgg accacattct gaaaagattt | 420 |
| aacttgaagg agaccgatat tgtccctgaa gaccgtttca tagctgcagc aaatagagga | 480 |
| tcttttatcct gtgtcaaaga aataatgtat gagactaaga caagcaataa ccaagcttat | 540 |
| ggcaaggtca atgtcctatc tccaaacaga aattctaatg aatggattta cactgttaaa | 600 |
| cctatgttca atcaaactga aacaaacaac agaactgtga actcgttggc tattaaatct | 660 |
| ttgcttttgt ctgctgtgaa cgacatttcc ccttgttctc aggtgttttt gaaagctttt | 720 |
| actgataaat ctttcaagct gtctttctgg ttgagaatcc caaaagtcct caaacacaca | 780 |
| gactttttata aatgcttcaa aataccgaat ggttcttcca acctttccct aacaataaac | 840 |
| tgtatcccaa actacaacaa cattgaaacg gcactgaact tttctctggt gtctctgaag | 900 |
| ccaaaggaac cattgagtgc tcctaaacag ggtaagtttg tcatcaactt ctctagttta | 960 |
| aaagaaccat gctgcaatgt ttttgatctt acttatcccc aaagaattgt ccactcactg | 1020 |
| ctcgaagttc atacatctct tgctaaaaaa ctatcgagatt ttttacgaga gaagtcatt | 1080 |
| atatacactt tgaatctgcc agaaactgaa gtgaaaagc tcgatcttgc tggaagaact | 1140 |
| cttaattaca atgaaagtcc ttctggaaag aagtattttc tgtctcaaac cttaaactgc | 1200 |
| ctccctaaaa actctcagag tttggcttat cttaacagtt tccaattctg ttctttgcat | 1260 |

| | |
|---|---:|
| gtcgactaca ttagaggcga aatatgtgtt ttaccgactt tgtcttcagc ctccagagca | 1320 |
| aatttgcgat tggacatagc atcaactatg tccaaaagcc cttttttga | 1368 |

<210> SEQ ID NO 3
<211> LENGTH: 789
<212> TYPE: DNA
<213> ORGANISM: Melon Severe Mosaic Virus

<400> SEQUENCE: 3

| | |
|---|---:|
| atgtctaaag tcaagcttac aaaagacaat atcatcaagc tcttgagcag taatgctgaa | 60 |
| attgaatttg aagaagaaca aaaccaatct actttccaat tgatacatt ttttgatgca | 120 |
| aatgtagaaa agctcaaaaa catgacagtg atgtcatgtt tgacctttct taagaacagg | 180 |
| caaagcataa tgaaagttgt taaacaagct gattttactt ttaatgggat cacaatcaaa | 240 |
| aaatcaaaac caaagataga gccaaaagat atgactttca ggaggctaga tgccatgata | 300 |
| agagcaaaaa tgattgagtt tactgccaaa gacgaggcat tggaaataat taaggttaag | 360 |
| atatcatcac accctctcgt catggcttac agccttgatg ttaatgatgc aaaatctgca | 420 |
| agaattgctt gtctcttggg aggaagcctg cctcttctag cttccattcc gcattatgaa | 480 |
| gctatttgcc ttgttcttgc tgtttatcaa gatgctaaat cacaggagct gggaatagac | 540 |
| cagaagaaat atgatactaa agaagctatt ggaaaagttt gcactgtttt gaaaagcaaa | 600 |
| ggctatgtga tggataatga tcaactggag aaagctaaaa tgtatgcaca aatcctcagc | 660 |
| aaatgtgatc ctaagctcaa gggagacatg gctatgaatc attatgaagc tgggttgaag | 720 |
| cagatctatg agatctttgg tgtttctgga tcgaagaaag cttcaaccag caaagttttt | 780 |
| gagatttaa | 789 |

<210> SEQ ID NO 4
<211> LENGTH: 1466
<212> TYPE: DNA
<213> ORGANISM: Melon Severe Mosaic Virus

<400> SEQUENCE: 4

| | |
|---|---:|
| ctacttcatc attaatacaa ggttaagttc tagcctttg aagtttttga cagaattgct | 60 |
| cataggtctt atcattctat ctcaaatgcc tatgtctcta gcacagacag caaaatgcat | 120 |
| tgacacttgc ttgtatgttg caggctgtaa taagctggtt acgagtaagt atgaaaaatg | 180 |
| tcctccagaa gatcaatgtt cctgcactat aacagatagt ggaatcatag aaaacatttg | 240 |
| gcattctggc attattgtca aggagtctaa caattgcttg aaaaaccaaa tatgtgcatc | 300 |
| agcctaccct tttgagcatc ttgtaaagtg cagaatcgga tgcgattact tgaacttgat | 360 |
| taagagtaaa cccctacctt caggatttgt tgattattca ggtgatctgt taaatctaga | 420 |
| cataaccagc ttgcattaca tgaaaaggct aagaggtgga attatagatt catataatat | 480 |
| gacagacacc ctcaccaaca tcttcccggg tgatgtgaca ttcaagggct tccctagaat | 540 |
| cccagagaat atactttcca ggcaatctct gatttatgat tctgttgttg atggaaaata | 600 |
| tagataccta atagaacagg ctctactagg tggaggaggg acagtcttc tgcttaatga | 660 |
| caaaacatct ggtgctgtgc agaagcttgt ggtttatgtt gagaaagtag gtgtccatta | 720 |
| tgaagtctca gaaaaataca ctacagctcc tatacaaagc actcacactg atttctactc | 780 |
| aacttgcaca gggaattgtg gtacatgtag aagaaatcaa cctgtaacag ggtatcaaga | 840 |
| ttttgcatc actcccacat cttactgggg ctgtgaagaa gcatggtgct ggctataaaa | 900 |
| tgaaggagcc acgtgcggtt tttgcagaaa tgtttatgac atggacaaag cttacaaaat | 960 |

```
ttattcagct ctgaaaacaa cgatcaaatc caccatttgt ttctccggtt tcccaggtgc    1020
atcttgtcat gaaataaatg aagaagttcc attagagaca acatactttc aagctgacat    1080
aatagcagac ctacacaacg atgaaattgt tgtgggtgaa ctcatagccc acagttctga    1140
tagccacatc tacaaaggaa acattacagg attgaatgac cctgtgaaaa tgtttggtca    1200
tccacagcta tcatttgaag ggaaacctat ctttagtaaa aaggttttag atggagatga    1260
tctttcttgg gattgtgcag ctataggaa aaagactgta aaaattaagt cttgtggtta    1320
tgacacttat agatttaaat ctggcttaga gcaattgtct tctattcctg ttactttcca    1380
agaccacaaa agcttttttct tagaaaagtc cttcaacctt ggaaagctaa agatcattat    1440
tgatctacca acagaattat ttaaag                                         1466
```

<210> SEQ ID NO 5
<211> LENGTH: 1019
<212> TYPE: DNA
<213> ORGANISM: Melon Severe Mosaic Virus

<400> SEQUENCE: 5

```
ctaatagaga aaagatgac caggatcaac tcctcaacag caggtaggtt cactgtatca     60
aatgttattc tctcgcacaa cagtgagttg aatacaatcc aaaagcagat tgtttggctt    120
tataatatgg gattgtgtag tgagaagaca ttagaatttg tcataagata tatcagaagg    180
agtgatgtta gatatgttag gactgaagag caagatgaaa tgggaaatta cgtctctggt    240
accgtgtaca aaactggtat catgacacag aattgctatg tccaactgat ggcatcagac    300
caggatatct cagtttcttt gaaaacacct ttcagcattc tgaatgaaag gaaccatctt    360
tatgatacgt ataagaaag catagaaaaa ttgcttcaca atacatgtt ggacaaatct     420 aacattgtaa agtctaaatt gccacagact acatatttag aacctggaca agcatgcttg    480
aggatgacat ctgacaacaa aatgattgtc aaagtcaatg ccactccaag gcagataaag    540
atggagaatg tcaaaatggt aattaatatt aaatatgaga atgtggattc agatttatgg    600
gaaattattg aaaaccagaa aactgtgact ttgaggaaac cagatccagg gaatgttttt    660
tctgagatgt acaaaacatt agattcagaa tcgagaatga taagtgcaat caagaacaa    720 ctggctaagt cattaacttt tttaaataca tttgaaaact tgtcaaatca aatagacgat    780
gttgaggaag aagacagcag ggaaaccttg caagacctgt tgcaacaatt gcaagaatct    840
tgtcttgaag ggttaggtca atgcaaaagc gtagaagaat acagcatgtt cttggatagc    900
aatgggtttt cccagactat agagcttttt aaaggcattt tagactcata tgatagcttt    960
gagtcagaat acagttctct attctcatcc ataatagaca aaactaccag gtttaccat    1019
```

<210> SEQ ID NO 6
<211> LENGTH: 455
<212> TYPE: PRT
<213> ORGANISM: Melon Severe Mosaic Virus

<400> SEQUENCE: 6

```
Met Ser Ser Ser Cys Leu Asp Ser Ile Val Gln Ser Lys Ala Ser Val
1               5                   10                  15

Trp Gly Thr Ser Val Ser Gly Lys Ser Ile Leu Asp Thr Tyr Trp Ile
            20                  25                  30

His Asp Tyr Glu Thr Gly Lys Pro Leu Leu Glu Thr Gln Leu Tyr Ser
        35                  40                  45

Asp Ser Arg Ser Lys Ser Ser Phe Cys Tyr Thr Asn Lys Val Asp Asp
    50                  55                  60
```

```
Ile Pro Ile Ala Asp Ala Glu Leu Val Ser Asp Ala Ser Val Phe Ser
65                  70                  75                  80

Leu Leu Asp Asp Ile Asp Phe Ser Met Thr Ile Glu Glu Ser Phe Ile
                85                  90                  95

Thr Val Ser Val Cys Ser Asn Thr Val Asn Thr Asn Gly Val Lys His
            100                 105                 110

Gln Gly His Leu Lys Ile Ile Ser Thr Gln Lys Pro Val Ala Leu Asn
        115                 120                 125

Phe Leu Ala Glu Ser Asp His Ile Leu Lys Arg Phe Asn Leu Lys Glu
    130                 135                 140

Thr Asp Ile Val Pro Glu Asp Arg Phe Ile Ala Ala Ala Asn Arg Gly
145                 150                 155                 160

Ser Leu Ser Cys Val Lys Glu Ile Met Tyr Glu Thr Lys Thr Ser Asn
                165                 170                 175

Asn Gln Ala Tyr Gly Lys Val Asn Val Leu Ser Pro Asn Arg Asn Ser
            180                 185                 190

Asn Glu Trp Ile Tyr Thr Val Lys Pro Met Phe Asn Gln Thr Glu Thr
        195                 200                 205

Asn Asn Arg Thr Val Asn Ser Leu Ala Ile Lys Ser Leu Leu Leu Ser
    210                 215                 220

Ala Val Asn Asp Ile Ser Pro Cys Ser Gln Val Phe Leu Lys Ala Phe
225                 230                 235                 240

Thr Asp Lys Ser Phe Lys Leu Ser Phe Trp Leu Arg Ile Pro Lys Val
                245                 250                 255

Leu Lys His Thr Asp Phe Tyr Lys Cys Phe Lys Ile Pro Asn Gly Ser
            260                 265                 270

Ser Asn Leu Ser Leu Thr Ile Asn Cys Ile Pro Asn Tyr Asn Asn Ile
        275                 280                 285

Glu Thr Ala Leu Asn Phe Ser Leu Val Ser Leu Lys Pro Lys Glu Pro
    290                 295                 300

Leu Ser Ala Pro Lys Gln Gly Lys Phe Val Ile Asn Phe Ser Ser Leu
305                 310                 315                 320

Lys Glu Pro Cys Cys Asn Val Phe Asp Leu Thr Tyr Pro Gln Arg Ile
                325                 330                 335

Val His Ser Leu Leu Glu Val His Thr Ser Leu Ala Lys Lys Leu Ser
            340                 345                 350

Asp Phe Leu Arg Glu Glu Val Ile Ile Tyr Thr Leu Asn Leu Pro Glu
        355                 360                 365

Thr Glu Val Lys Lys Leu Asp Leu Ala Gly Arg Thr Leu Asn Tyr Asn
    370                 375                 380

Glu Ser Pro Ser Gly Lys Lys Tyr Phe Leu Ser Gln Thr Leu Asn Cys
385                 390                 395                 400

Leu Pro Lys Asn Ser Gln Ser Leu Ala Tyr Leu Asn Ser Phe Gln Phe
                405                 410                 415

Cys Ser Leu His Val Asp Tyr Ile Arg Gly Glu Ile Cys Val Leu Pro
            420                 425                 430

Thr Leu Ser Ser Ala Ser Arg Ala Asn Leu Arg Leu Asp Ile Ala Ser
        435                 440                 445

Thr Met Ser Lys Ser Pro Phe
    450                 455
```

<210> SEQ ID NO 7
<211> LENGTH: 262
<212> TYPE: PRT
<213> ORGANISM: Melon Severe Mosaic Virus

```
<400> SEQUENCE: 7

Met Ser Lys Val Lys Leu Thr Lys Asp Asn Ile Ile Lys Leu Leu Ser
1               5                   10                  15

Ser Asn Ala Glu Ile Glu Phe Glu Glu Gln Asn Gln Ser Thr Phe
            20                  25                  30

Gln Phe Asp Thr Phe Phe Asp Ala Asn Val Glu Lys Leu Lys Asn Met
        35                  40                  45

Thr Val Met Ser Cys Leu Thr Phe Leu Lys Asn Arg Gln Ser Ile Met
50                  55                  60

Lys Val Val Lys Gln Ala Asp Phe Thr Phe Asn Gly Ile Thr Ile Lys
65                  70                  75                  80

Lys Ser Lys Pro Lys Ile Glu Pro Lys Asp Met Thr Phe Arg Arg Leu
                85                  90                  95

Asp Ala Met Ile Arg Ala Lys Met Ile Glu Phe Thr Ala Lys Asp Glu
            100                 105                 110

Ala Leu Glu Ile Ile Lys Val Lys Ile Ser Ser His Pro Leu Val Met
        115                 120                 125

Ala Tyr Ser Leu Asp Val Asn Asp Ala Lys Ser Ala Arg Ile Ala Cys
130                 135                 140

Leu Leu Gly Gly Ser Leu Pro Leu Leu Ala Ser Ile Pro His Tyr Glu
145                 150                 155                 160

Ala Ile Cys Leu Val Leu Ala Val Tyr Gln Asp Ala Lys Ser Gln Glu
                165                 170                 175

Leu Gly Ile Asp Gln Lys Lys Tyr Asp Thr Lys Glu Ala Ile Gly Lys
            180                 185                 190

Val Cys Thr Val Leu Lys Ser Lys Gly Tyr Val Met Asp Asn Asp Gln
        195                 200                 205

Leu Glu Lys Ala Lys Met Tyr Ala Gln Ile Leu Ser Lys Cys Asp Pro
210                 215                 220

Lys Leu Lys Gly Asp Met Ala Met Asn His Tyr Glu Ala Gly Leu Lys
225                 230                 235                 240

Gln Ile Tyr Glu Ile Phe Gly Val Ser Gly Ser Lys Lys Ala Ser Thr
                245                 250                 255

Ser Lys Val Phe Glu Ile
            260

<210> SEQ ID NO 8
<211> LENGTH: 488
<212> TYPE: PRT
<213> ORGANISM: Melon Severe Mosaic Virus

<400> SEQUENCE: 8

Tyr Phe Ile Ile Asn Thr Arg Leu Ser Ser Ser Leu Leu Lys Phe Leu
1               5                   10                  15

Thr Glu Leu Leu Ile Gly Leu Ile Ile Leu Ser Gln Met Pro Met Ser
            20                  25                  30

Leu Ala Gln Thr Ala Lys Cys Ile Asp Thr Cys Leu Tyr Val Ala Gly
        35                  40                  45

Cys Asn Lys Leu Val Thr Ser Lys Tyr Glu Lys Cys Pro Pro Glu Asp
50                  55                  60

Gln Cys Ser Cys Thr Ile Thr Asp Ser Gly Ile Ile Glu Asn Ile Trp
65                  70                  75                  80

His Ser Gly Ile Ile Val Lys Glu Ser Asn Asn Cys Leu Lys Asn Gln
                85                  90                  95
```

```
Ile Cys Ala Ser Ala Tyr Pro Phe Glu His Leu Val Lys Cys Arg Ile
            100                 105                 110

Gly Cys Asp Tyr Leu Asn Leu Ile Lys Ser Lys Pro Leu Pro Ser Gly
            115                 120                 125

Phe Val Asp Tyr Ser Gly Asp Leu Leu Asn Leu Asp Ile Thr Ser Leu
            130                 135                 140

His Tyr Met Lys Arg Leu Arg Gly Gly Ile Ile Asp Ser Tyr Asn Met
145                 150                 155                 160

Thr Asp Thr Leu Thr Asn Ile Phe Pro Gly Asp Val Thr Phe Lys Gly
                165                 170                 175

Phe Pro Arg Ile Pro Glu Asn Ile Leu Ser Arg Gln Ser Leu Ile Tyr
            180                 185                 190

Asp Ser Val Val Asp Gly Lys Tyr Arg Tyr Leu Ile Glu Gln Ala Leu
            195                 200                 205

Leu Gly Gly Gly Gly Thr Val Phe Leu Leu Asn Asp Lys Thr Ser Gly
            210                 215                 220

Ala Val Gln Lys Leu Val Val Tyr Val Glu Lys Val Gly Val His Tyr
225                 230                 235                 240

Glu Val Ser Glu Lys Tyr Thr Thr Ala Pro Ile Gln Ser Thr His Thr
                245                 250                 255

Asp Phe Tyr Ser Thr Cys Thr Gly Asn Cys Gly Thr Cys Arg Arg Asn
            260                 265                 270

Gln Pro Val Thr Gly Tyr Gln Asp Phe Cys Ile Thr Pro Thr Ser Tyr
            275                 280                 285

Trp Gly Cys Glu Glu Ala Trp Cys Leu Ala Ile Asn Glu Gly Ala Thr
            290                 295                 300

Cys Gly Phe Cys Arg Asn Val Tyr Asp Met Asp Lys Ala Tyr Lys Ile
305                 310                 315                 320

Tyr Ser Ala Leu Lys Thr Thr Ile Lys Ser Thr Ile Cys Phe Ser Gly
                325                 330                 335

Phe Pro Gly Ala Ser Cys His Glu Ile Asn Glu Glu Val Pro Leu Glu
            340                 345                 350

Thr Thr Tyr Phe Gln Ala Asp Ile Ile Ala Asp Leu His Asn Asp Glu
            355                 360                 365

Ile Val Val Gly Glu Leu Ile Ala His Ser Ser Asp Ser His Ile Tyr
            370                 375                 380

Lys Gly Asn Ile Thr Gly Leu Asn Asp Pro Val Lys Met Phe Gly His
385                 390                 395                 400

Pro Gln Leu Ser Phe Glu Gly Lys Pro Ile Phe Ser Lys Lys Val Leu
                405                 410                 415

Asp Gly Asp Asp Leu Ser Trp Asp Cys Ala Ala Ile Gly Lys Lys Thr
            420                 425                 430

Val Lys Ile Lys Ser Cys Gly Tyr Asp Thr Tyr Arg Phe Lys Ser Gly
            435                 440                 445

Leu Glu Gln Leu Ser Ser Ile Pro Val Thr Phe Gln Asp His Lys Ser
            450                 455                 460

Phe Phe Leu Glu Lys Ser Phe Asn Leu Gly Lys Leu Lys Ile Ile Ile
465                 470                 475                 480

Asp Leu Pro Thr Glu Leu Phe Lys
                485

<210> SEQ ID NO 9
<211> LENGTH: 339
<212> TYPE: PRT
<213> ORGANISM: Melon Severe Mosaic Virus
```

<400> SEQUENCE: 9

```
Leu Ile Glu Lys Lys Met Thr Arg Ile Asn Ser Ser Thr Ala Gly Arg
1               5                   10                  15

Phe Thr Val Ser Asn Val Ile Leu Ser His Asn Ser Glu Leu Asn Thr
            20                  25                  30

Ile Gln Lys Gln Ile Val Trp Leu Tyr Asn Met Gly Leu Cys Ser Glu
        35                  40                  45

Lys Thr Leu Glu Phe Val Ile Arg Tyr Ile Arg Arg Ser Asp Val Arg
    50                  55                  60

Tyr Val Arg Thr Glu Gln Asp Glu Met Gly Asn Tyr Val Ser Gly
65                  70                  75                  80

Thr Val Tyr Lys Thr Gly Ile Met Thr Gln Asn Cys Tyr Val Gln Leu
                85                  90                  95

Met Ala Ser Asp Gln Asp Ile Ser Val Ser Leu Lys Thr Pro Phe Ser
            100                 105                 110

Ile Leu Asn Glu Arg Asn His Leu Tyr Asp Thr Tyr Lys Glu Ser Ile
        115                 120                 125

Glu Lys Leu Leu His Lys Tyr Met Leu Asp Lys Ser Asn Ile Val Lys
    130                 135                 140

Ser Lys Leu Pro Gln Thr Thr Tyr Leu Glu Pro Gly Gln Ala Cys Leu
145                 150                 155                 160

Arg Met Thr Ser Asp Asn Lys Met Ile Val Lys Val Asn Ala Thr Pro
                165                 170                 175

Arg Gln Ile Lys Met Glu Asn Val Lys Met Val Ile Asn Ile Lys Tyr
            180                 185                 190

Glu Asn Val Asp Ser Asp Leu Trp Glu Ile Ile Glu Asn Gln Lys Thr
        195                 200                 205

Val Thr Leu Arg Lys Pro Asp Pro Gly Glu Cys Phe Ser Glu Met Tyr
    210                 215                 220

Lys Thr Leu Asp Ser Glu Ser Arg Met Ile Ser Ala Ile Lys Glu Gln
225                 230                 235                 240

Leu Ala Lys Ser Leu Thr Phe Leu Asn Thr Phe Glu Asn Leu Ser Asn
                245                 250                 255

Gln Ile Asp Asp Val Glu Glu Leu Asp Ser Arg Glu Thr Leu Gln Asp
            260                 265                 270

Leu Leu Gln Gln Leu Gln Glu Ser Cys Leu Glu Gly Leu Gly Gln Cys
        275                 280                 285

Lys Ser Val Glu Glu Tyr Ser Met Phe Leu Asp Ser Asn Gly Phe Ser
    290                 295                 300

Gln Thr Ile Glu Leu Phe Lys Gly Ile Leu Asp Ser Tyr Asp Ser Phe
305                 310                 315                 320

Glu Ser Glu Tyr Ser Ser Leu Phe Ser Ser Ile Ile Asp Lys Thr Thr
                325                 330                 335

Arg Phe Thr
```

<210> SEQ ID NO 10
<211> LENGTH: 23
<212> TYPE: DNA
<213> ORGANISM: Artificial Sequence
<220> FEATURE:
<223> OTHER INFORMATION: MeSMV specific primer 2490-F

<400> SEQUENCE: 10
tgctgaggat ttgtgcatac att                                    23

```
<210> SEQ ID NO 11
<211> LENGTH: 25
<212> TYPE: DNA
<213> ORGANISM: Artificial Sequence
<220> FEATURE:
<223> OTHER INFORMATION: MeSMV specific primer 2900-R

<400> SEQUENCE: 11
gggatcacaa tcaaaaaatc aaaac                                              25

<210> SEQ ID NO 12
<211> LENGTH: 18
<212> TYPE: DNA
<213> ORGANISM: Artificial Sequence
<220> FEATURE:
<223> OTHER INFORMATION: MeSMV specific primer 2510-R

<400> SEQUENCE: 12
tggataatga tcaactgg                                                      18

<210> SEQ ID NO 13
<211> LENGTH: 18
<212> TYPE: DNA
<213> ORGANISM: Artificial Sequence
<220> FEATURE:
<223> OTHER INFORMATION: MeSMV specific primer 1380-F

<400> SEQUENCE: 13
gtcttcagcc tccagagc                                                      18

<210> SEQ ID NO 14
<211> LENGTH: 18
<212> TYPE: DNA
<213> ORGANISM: Artificial Sequence
<220> FEATURE:
<223> OTHER INFORMATION: MeSMV specific primer 1020-R

<400> SEQUENCE: 14
cctaaacagg gtaagttt                                                      18
```

BREEDING AND SELECTION FOR RESISTANCE TO MELON SEVERE MOSAIC VIRUS (MESMV)

CROSS-REFERENCE TO RELATED APPLICATIONS

This application claims priority to U.S. Provisional Application No. 61/264,584, filed Nov. 25, 2009, which is hereby incorporated by reference in its entirety.

TECHNICAL FIELD

The application relates to identification of plants with resistance to Melon Severe Mosaic Virus (MeSMV), methods of developing plants (e.g., through plant breeding) with resistance to said virus; and to the resistant plants developed by such methods.

BACKGROUND

The cucurbit family includes a number of valuable crop species (melon, cucumber, squash/pumpkin, watermelon, et al.). Production of cucurbit crops in large quantities is important worldwide, since cucurbits are important commercially in many regions, and are increasingly available throughout the year. According to Food and Agriculture Organization (FAO, 2002), world production of watermelon exceeded 80 million tons worldwide; cucumber exceeded 36 million tons; melon exceeded 22 million tons, and squash exceeded 17 million tons.

However, a wide range of pathogens (virus, fungi, bacteria, nematodes, and insects) affects productivity of cucurbits (Blanchard et al., 1994, A color atlas of cucurbit diseases, New York: Manson Publishing/John Wiley; Zitter et al., 1996 Compendium of cucurbit diseases. St Paul, Minn.: APS Press). Among these, virus diseases of cucurbits are an important limitation in production. Massive damage up to total loss can be caused by virus, which prevents the growth of some cucurbit crops in certain area. Cucurbits are susceptible to many viruses from several virus families and virus resistance is therefore of major agricultural importance (Provvidenti, 1993, Resistance to viral disease of cucurbits. In: Kyle, M. M., ed. *Resistance to viral diseases of vegetables*. Portland, Oreg.: Timber Press; 1993:8-43).

The genus Tospovirus (Bunyaviridae) (9, 18) includes some of the most important plant viruses causing severe diseases in agricultural, ornamental, and horticultural, crops (16, 26, 34, 100). The type member of the genus is Tomato spotted wilt virus (TSWV; 20).

Cucurbit-infecting Tospovirus spp. have been identified in different countries since the 1980s, particularly in South America and Asia. Two cucurbit-infecting Tospovirus spp. are included in the list of the species accepted by the International Committee on Taxonomy of Viruses (ICTV): Watermelon silver mottle virus (WSMoV), originally reported on *Citrullus lanatus* in Okinawa, Japan in 1982 and in 1992 in Taiwan (40); and Zucchini lethal chlorosis virus (ZLCV), reported on *Cucurbita pepo* in Brazil in 1999 (1). In addition, two tentative species from cucurbits have been proposed: Watermelon bud necrosis virus (WBNV), reported on cucurbits in India (13); and, more recently, Melon yellow spot virus (MYSV) on netted melon in Japan and Thailand (14; 101).

A novel Tospovirus (Bunyaviridae) species was recently isolated (Ciuffo et al., "A New *Tospovius* sp. in Cucurbit Crops in Mexico", *Plant Disease*, May 2009, 93(5):467-474). In the state of Guerrero, Mexico, several honeydew melon (*Cucumis melo*) plants exhibiting mosaic, leaf blistering, leaf deformation, and fruit splitting were observed. Electron-microscopic analysis of leaf-dip extracts showed only particles with the morphological features of viruses of the Tospovirus genus. Biological, serological, and molecular properties and phylogenetic analysis showed that this Tospovirus sp. is a new and distinct species in the genus Tospovirus and is tentatively named Melon Severe Mosaic Virus MeSMV). Subsequent surveys showed its widespread occurrence in cucurbit crops in Mexico. Methods of screening plants for resistance, tolerance or susceptibility to such virus; and methods of producing plants resistant or tolerant to such virus are provided herein.

SUMMARY

The present invention provides methods for diagnosing a plant for MeSMV. In one embodiment, the methods comprise detecting the presence of any proteins derived from MeSMV, based on immunological detection. In another embodiment, said MeSMV protein is one or more MeSMV proteins as described elsewhere herein. In another embodiment, the methods comprise detecting the presence of one or more MeSMV-specific nucleic acid sequences corresponding to the one or more isolated MeSMV nucleic acid sequences as described elsewhere herein, based on nucleotide hybridization or amplification. In one embodiment, said plant is a cucurbit crop. For example, the plant is a melon, a watermelon, a squash, or a cucumber.

In one embodiment, the methods comprise: a) contacting a biological sample with one or more antibodies as described elsewhere herein, under conditions for antibody binding, and b) detecting presence or absence of the binding. In one embodiment, said biological sample is a plant extract. In one embodiment, the detecting step comprises an immunological detection test selected from the group consisting of precipitation and agglutination tests, immunogold labeling, immunosorbent electron microscopy, enzyme linked immunosorbent assay (ELISA), Western blot, radioimmunoassay (RIA), and dot blot. In one embodiment, the ELISA is a direct antibody sandwich enzyme linked immunosorbent assay (DAS-ELISA). In another embodiment, the ELISA is a Lateral Flow test.

In another embodiment, the methods comprise a) extracting nucleic acids from a biological sample and b) detecting the presence or absence of one or more MeSMV-specific nucleic acids. In one embodiment, the MeSMV-specific nucleic acid sequences are in one or more different regions. In one embodiment, said regions can be of one or more different genes of a MeSMV. In one embodiment, the biological sample can be prepared by any method, wherein the sample contains a template selected from the group consisting of DNA, RNA, and otherwise, so long as the template fits the criteria for amplification purposes by those skilled in the art. In one embodiment, said amplification method is RT-PCR. In one embodiment, the RT PCR is performed using a real time PCR technique. In another embodiment, the detecting step comprises nucleic acid hybridization between the MeSMV-specific nucleic acid and one or more MeSMV-specific probes. In one embodiment, said nucleic acid hybridization is a Northern blot or a Southern blot.

The present invention also provides methods of screening a plant population, plant, plant part, plant tissue, and/or plant cell that is resistant or susceptible to MeSMV, comprising: a) growing the plant population, plant, plant tissue, or plant cell; b) challenging the plant population, plant, plant tissue, plant cell with the isolated MeSMV strain as described elsewhere herein; and c) evaluating the resistance in the plant population, plant, plant tissue, plant cell, wherein a plant population, plant, plant tissue, plant cell that is resistant or susceptible to MeSMV is identified.

In one embodiment, said plant is a dicot. In another embodiment said plant is a monocot. In some embodiments, said plant is a cucurbit crop. For example, the plant can be a squash, a melon, a watermelon, a cucumber, or a zucchini.

In one embodiment, said evaluating step comprises visual estimation. In one embodiment, said evaluating step comprising a molecular test or a biological test of virus density. In one embodiment, said visual observation comprises a resistance or tolerance scoring system. In one embodiment, said molecular test comprises evaluating the density of MeSMV-specific nucleic acids corresponding to any nucleic acid sequences as described above, or the density of MeSMV-specific amino acids as described above. In one embodiment, said density of MeSMV-specific nucleic acids is evaluated by molecular method comprising nucleic acids test selected from the group consisting of RT-PCR, Northern blot and Southern blot. In one embodiment, said molecular method comprises testing the density of MeSMV protein corresponding to any amino acid sequences as described above. In one embodiment, said method is performed in an ELISA (e.g., Lateral Flow test, or DAS-ELISA), Western blot, RIA, or dot blot. In one embodiment, said density of MeSMV-specific amino acids is evaluated by molecular method comprising an immunological detection test selected from the group consisting of precipitation and agglutination tests, immunogod labeling, immunosorbent electron microscopy, enzyme linked immunosorbent assay (ELISA, e.g., Lateral Flow test, or DAS-ELISA), Western blot, radioimmunoassay (RIA), and dot blot. The present invention also provides an isolated plant population, plant part, plant, plant tissue or plant cell wherein the plant population, plant, plant part, plant tissue or plant cell is resistant or tolerant to MeSMV. In one embodiment, the isolated plant is a dicot. In another embodiment, the plant is a monocot. In further embodiments, the plant is a cucurbit crop.

The present invention also provides a tissue culture of the isolated plant population, plant, plant part, plant tissue or plant cell, wherein said tissue culture retains resistance or tolerance to MeSMV.

The present invention also provides a seed derived from the isolated plant population, plant, plant part, plant tissue or plant cell, wherein said seed can give rise to a plant that is also resistant or tolerant to MeSMV.

The present invention also provides a progeny derived from the isolated plant as described above, whether produced sexually or asexually, wherein said progeny retains resistance or tolerance to MeSMV.

The present invention also provides a method of isolating a nucleic acid sequence conferring resistance or tolerance to MeSMV, comprising: a) crossing a plant resistant or tolerant to MeSMV as a donor with a suitable plant that is susceptible to said virus to produce offspring plants as a mapping population; b) challenging said offspring plants with said virus and determining the resistance in said offspring plants; and c) cloning the nucleic acid. In one embodiment, said cloning step comprises map-based cloning. In another embodiment, said cloning step comprises association mapping.

The present invention also provides a method of isolating one or more quantitative trait locus (QTL) contributing to the resistance or tolerance to the isolated virus of present invention, comprising: a) crossing the isolated plant resistant to the isolated virus of the present invention as a donor with a suitable plant that is susceptible to said virus to produce offspring plants; b) challenging one or more said offspring plants with an infective dosage of said virus; c) quantitatively determining the resistance or tolerance in said one or more offspring plants; d) establishing a genetic linkage map that links the observed resistance or tolerance to the presence of chromosomal markers of said donor plant in said one or more offspring plants; and e) assigning to a QTL the contiguous markers on said map that are linked to enhanced disease resistance or tolerance.

The present invention also provides a plant population, plant, plant part, plant tissue, or plant cell that is resistance to the isolated virus of present invention, wherein the plant population, plant, plant part, plant tissue, or plant cell is produced by transferring a nucleic acid sequence conferring resistance or tolerance to MeSMV, and/or one or more QTLs contributing to the resistance or tolerance isolated by the methods described above, to a plant population, plant, plant part, plant tissue, or plant cell of interest. In one embodiment, the nucleic acid sequence and/or the QTLs can be transferred by breeding methods. In one embodiment, said breeding method comprises using introgression line library. In another embodiment, the nucleic acid sequence and/or the QTLs can be transferred by plant transformation.

The present invention further provides methods of breeding cucurbit plants that are resistant to Melon Severe Mosaic Virus (MeSMV). In some embodiments, the methods comprise the steps of: (i) providing a first cucurbit plant, said first cucurbit plant is resistant to MeSMV; (ii) crossing the cucurbit plant provided in step (i) with a second cucurbit plant to produce progeny plants; (iii) selecting one or more progeny plants that are resistant to MeSMV from the progeny of step (ii); (iv) backcrossing the selected progeny plants of step (iii) or selfed offspring thereof with the second cucurbit plant of step (ii) to produce backcross progeny plants; (v) selecting for backcross progeny plants that are resistant to MeSMV from the backcross progeny plants of step (iv); and (vi) repeating steps (iv) and (v) three or more times in succession to produce selected fourth or higher backcross progeny plants that are resistant to MeSMV.

In some embodiments, the first cucurbit plant resistant to MeSMV is a *Cucurbita moschata* plant or a *Cucurbita maxima* plant. In some embodiments, the *C. moschata* plant is 'Menian Rajada Seca', 'Nigerian', 'Native squash' (Ns), 'Butterfly', Mexican 'land race' (Ws), Shimer Kobocha (Sk), or hybrid thereof.

In some embodiments, wherein the second cucurbit plant is a plant having desired trait and physiological and morphological characteristics. For example, the second cucurbit plant is a commercial elite cucurbit plant that is susceptible to MeSMV.

In some embodiments, the second cucurbit plant is a *Cucurbita pepo* plant. For example, the second cucurbit plant is Vigne squash variety, Zucchini Elite, Hurakon, Linda, Citlali, SSXP 4511, Golden Arrow, SSXP 4506, Huaso, SSXP 4507, Arte, SSXP 4512, or hybrid thereof.

Accordingly, the present invention provides cucurbit plants produced by the breeding methods described above. In some further embodiments, the present invention provides a cucurbit plant, plant part, or plant cell derived from the plant produced by the breeding methods described above, for example, cucurbit plant seeds derived from said selected plant.

The present invention also provides methods of breeding melon resistant to Melon Severe Mosaic Virus (MeSMV), wherein the method comprising the steps of (i) providing a first melon plant, said first melon plant is resistant to MeSMV; (ii) crossing the melon plant provided in step (i) with a second melon plant to produce progeny plants; (iii) selecting one or more progeny plants that are resistant to MeSMV from the progeny of step (ii);

(iv) backcrossing the selected progeny plants of step (iii) or selfed offspring thereof with the second melon plant of step (ii) to produce backcross progeny plants; (v) selecting for backcross progeny plants that are resistant to MeSMV from the backcross progeny plants of step (iv); and (vi) repeating steps (iv) and (v) three or more times in succession to produce selected fourth or higher backcross progeny plants that are resistant to MeSMV.

In another embodiment, the present invention provides methods of breeding a cucurbit plant, wherein the methods comprise the steps of: (i) providing a first cucurbit plant, said first cucurbit plant being resistant to MeSMV; (ii) crossing the cucurbit plant provided in step (i) with a second cucurbit plant to produce progeny plants; and (iii) selecting one or more progeny plants that are resistant to MeSMV from the progeny of step (ii). In other embodiments, this method ruther comprises crossing the selected progeny plants of step (iii) or selfed offspring thereof with another cucurbit plant and harvesting the resulted seeds. The present invention also provides one or more plants, or populations of plants, or cultivars grown from the resultant seeds produced by such methods, wherein the plants, plant populations or cultivars are resistant to MeSMV.

In some embodiments for the methods of the present invention, the first melon plant resistant to MeSMV is a variety selected from the MeSMV resistant melon varieties in Table 8, Table 9, or variety TGR 1551.

In some embodiments, the second melon plant is a plant having desired trait and physiological and morphological characteristics. For example, the second melon plant is a commercial elite melon plant that is susceptible to MeSMV.

Accordingly, the present invention provides melon plants produced by the breeding methods described above. In some further embodiments, the present invention provides a melon plant, plant part, or plant cell derived from the plant produced by the breeding methods described above, for example, melon plant seeds derived from said selected plant.

BRIEF DESCRIPTION OF THE DRAWINGS

FIG. 4 depicts Western blot analysis of leaf extracts from *Nicotiana benthamiana* plants infected with Tomato spotted wilt virus (TSWV), Impatiens necrotic spot virus (INSV), and MeSMV using antibodies against the nucleocapsid of TSWV and MeSMV. Lower panel is a Coomassie stain of the gel to show the amount of total protein loaded.

FIG. 5 depicts phylogenetic analysis of MeSMV proteins. A, Consensus phylogenetic tree obtained from alignments of the nucleocapsid (N) protein sequences of 21 Tospovirus spp., including accepted and tentative species: Capsicum chlorosis virus (CaCV) ABC86907, Calla lily chlorotic spot (CCSV) AAW58115, Chrysanthemum stem necrosis virus (CSNV) AAF04197, Groundnut bud necrosis virus (GBNV) AAR24021, Gloxinia ringspot virus (GloxRSV) AAQ83791, Groundnut ring spot virus (GRSV) AAF25255, Iris yellow spot virus (IYSV) AAF75556, Melon yellow severe virus (MYSV) BAB79455, Peanut bud necrosis virus (PBNV) AAM76063, Peanut chlorotic fanspot virus (PCFV) AAC99405, Polygonum ringspot virus (PolRSV) EF445397, Physalis severe mosaic virus (PhySMV) AAD34201, Peanut yellow spot virus (PYSV) AAB94022, Tomato chlorotic spot virus (TCSV) AAG23654, Tomato necrosis virus (TomNecrV) AAT68025, Tomato spotted wilt virus (TSWV) BAA03025, Tomato yellow ring virus (TYRV) ABF59486, Watermelon bud necrosis virus (WBNV) ABD39046, Watermelon silver mottle virus (WSMoV) AAW64930, Zucchini lethal chlorosis virus (ZLCV) AAF04198, Impatiens necrotic spot virus (INSV) AAA47974, and Bunyamwera virus NP_047213. PBNV is now considered a strain of GBNV (10). B, Consensus phylogenetic tree obtained from alignments of G protein sequence fragments of 15 Tospovirus spp. or isolates. Branches at nodes with a bootstrap value <50 have been collapsed to politomy. Viruses: La crosse virus (AAB62803.1), GBNV (NP_619703.1), Gloxinia tospovirus (GTV) (AAC15466.1), GRSV (AAU10600.2), INSV (ABD93457.1), MYSV (YP_717935.1), PolRSV (ABX65310.1), TCSV (AAU10599.2), Tomato zonate spot virus (TZSV) (YP_001740046.1), TSWV (AAV28056.1), WSMoV (NP_620767.1), ZLCV (BAF62147.1), IYSV (AAL62023.1), CaCV (YP_717926.1), and CSNV (BAF62146.1).

DESCRIPTION OF THE TEXT FILE SUBMITTED ELECTRONICALLY

Figure 1:
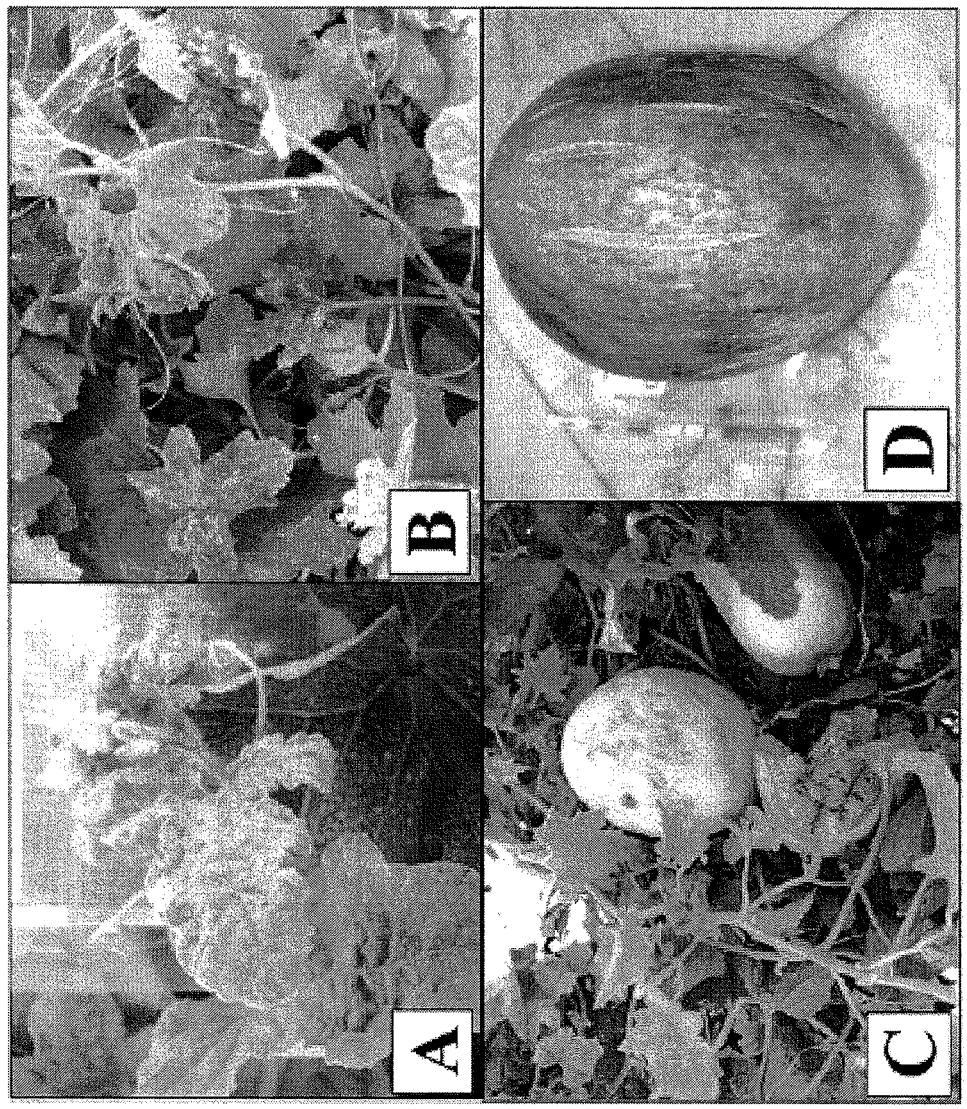
FIG. 1 depicts symptoms of melon plants infected with Melon Severe Mosaic Virus (MeSMV) in a field in Mexico. A, Early onset of mosaic and leaf blistering symptoms on honeydew melon leaves; B, advanced blistering, mosaic, and leaf deformation on honeydew melon; C, necrotic lesions on mature honeydew melon; and D, and immature honeydew fruit exhibiting necrotic fruit splitting.

The contents of the text file submitted electronically herewith are incorporated herein by reference in their entireties: A computer readable format copy of the Sequence Listing (filename: HAMO-001-01US.txt, date recorded: Nov. 24, 2010, file size 26 kilobytes).

DETAILED DESCRIPTION

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

DEFINITIONS

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom). This includes familiar organisms such as but not limited to trees, herbs, bushes, grasses, vines, ferns, mosses and green algae. The term refers to both monocotyledonous plants, also called monocots, and dicotyledonous plants, also called dicots. Examples of particular plants include but are not limited to corn, potatoes, roses, apple trees, sunflowers, wheat, rice, bananas, tomatoes, opo, pumpkins, squash, lettuce, cabbage, oak trees, *guzmania*, geraniums, hibiscus, clematis, poinsettias, sugarcane, taro, duck weed, pine trees, Kentucky blue grass, zoysia, coconut trees, *brassica* leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other *brassica* leafy vegetable crops), bulb vegetables (e.g. garlic, leek, onion (dry bulb, green, and Welch), shallot, and other bulb vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of *cucumis* melons), watermelon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatoes, barberries, currants, elderberryies, gooseberries, honeysuckles, mayapples, nannyberries, Oregon-grapes, seebuckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, and quinoa), pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fibber crops (e.g. hemp, cotton), ornamentals, and the like. For example, the plant is a cucurbit crop (e.g., melon, watermelon, squash/pumpkin, cucumber, and zucchini.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "chimeric protein" refers a constructs that links at least two heterologous proteins into a single macromolecule (fusion protein).

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "homologous" or "homologue" or "ortholog" is known in the art and refers to related sequences that share a common ancestor or family member and are determined based on the degree of sequence identity. The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71.

Some alignment programs are MacVector (Oxford Molecular Ltd, Oxford, U.K.) and ALIGN Plus (Scientific and Educational Software, Pennsylvania). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations containing alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art, As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "agent", as used herein, means a biological or chemical compound such as a simple or complex organic or inorganic molecule, a peptide, a protein or an oligonucleotide that modulates the function of a nucleic acid or polypeptide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

As used herein, the term "at least a portion" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

As used herein, the term "substantially complementary" means that two nucleic acid sequences have at least about 65%, preferably about 70% or 75%, more preferably about 80% or 85%, even more preferably 90% or 95%, and most preferably about 98% or 99%, sequence complementarities to each other. This means that primers and probes must exhibit sufficient complementarity to their template and target nucleic acid, respectively, to hybridise under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

As used herein the term "immunological detection" or "protein hybridization" refers to methods of detecting certain amino acid sequence. Non-limiting examples include, precipitation and agglutination tests, ELISA (e.g., Lateral Flow test, or DAS-ELISA), Western blot, RIA, immunogod labeling, immunosorbent electron microscopy (ISEM), and/or dot blot.

As used herein, the term "isolated virus" refers to a whole virus or a fragment of a virus which is obtained from any source whatsoever (e.g., from soil, from an insect, from a plant, or from part of a plant) through a method selected from the group consisting of physical, chemical, and/or biological separation/transfection methods, which includes, but are not limited to grinding, squeezing, smashing, cutting, soaking, washing, centrifuging, gradient centrifuging, ultra-centrifuging, thin layer centrifuging, chromatography, electrophoresis, electro-extraction, immunoprecipitation, inoculation, transfection, et al. The isolated virus can be in a liquid form, a solid form, or a mixture thereof. For example, said isolated virus is directly obtained by grinding plant leaf tissue and collecting the grinded material. An isolated virus can be used in the following exemplary infection procedures: 1) growing a healthy scion on a virus-infected rootstock, or vice versa; 2) exposing a healthy plant to transmission vectors containing the virus; 3) introducing into a healthy plant an expression vector harboring a coding region of the virus genome; 4) use of agro-infectious clones, such as *Agrobacterium tumefaciens* strains containing an expression vector harboring a coding region of the virus genome. Thus, in the context of the present invention, methods for challenging a plant, plant part, and/or plant cell to an infective dosage of MeSMV are not limited to any particular method. For example, infection may comprise mechanical inoculation of the virus on healthy plants. In one embodiment, a portion of a diseased leaf may be rubbed directly onto a leaf of a plant that is to be challenged.

As used herein, the term "substantially pure virus" refers to a whole virus or a fragment or a particle of a virus which is obtained from any source whatsoever wherein the virus or virus fragment or particle is substantially separated from other components which may accompany it and/or are naturally associated with it. Thus, a substantially pure virus may be one wherein the composition comprising the virus also contains minor amounts of other substances, also known as impurities, such as small amounts of plant tissue or soil minerals. Generally, a virus or virus fragment or particle is considered to be substantially pure if it contains less than about 5% of other materials, or if it contains less than about 4% of other materials, or if it contains less than about 3% of other materials, or if it contains less than about 2% of other materials, or if it contains less than about 1% of other materials, or if it contains less than about 0.5% of other materials.

As used herein, the term "suppression" or "disruption" of regulation refers to reduced activity of regulatory proteins, and such reduced activity can be achieved by a variety of mechanisms including antisense, mutation knockout or RNAi. Antisense RNA will reduce the level of expressed protein resulting in reduced protein activity as compared to wild type activity levels. A mutation in the gene encoding a protein may reduce the level of expressed protein and/or interfere with the function of expressed protein to cause reduced protein activity.

As used herein, the terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T en G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M $Na^+$ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001.

The term "antigen" refers to a substance capable of triggering an immune response in a vertebrate, resulting in production of an antibody as part of the defense against said substance. Antigens can be virus proteins that can provoke the antibody production in for instance blood cells, cells of lymph nodes, and spleen of vertebrates.

The term "antibody" includes reference to antigen binding peptides and refers to antibodies, monoclonal antibodies, to an entire immunoglobulin or antibody or any functional fragment of an immunoglobulin molecule. Examples of such peptides include complete antibody molecules, antibody fragments, such as Fab, F(ab')2, complementarity determining regions (CDRs), VL (light chain variable region), VH (heavy chain variable region), and any combination of those or any other functional portion of an antibody peptide. The temi "antibody" refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The terms "substantially pure" and "isolated" as they relate to proteins, peptides and/or nucleic acids are used interchangeably and describe a protein, peptide or nucleic acid which is substantially separated from other (sub)cellular components which naturally accompany it. The term embraces a nucleic acid or protein which has been removed from its naturally occurring environment, and includes recombinant or cloned DNA isolates and chemically synthesized analogues or analogues biologically synthesized by heterologous systems. Generally, the term refers to a purified protein and nucleic acid having a purity of at least about 75%, for example 85%, 95% or 98% by weight. Minor variants or chemical modifications typically share the same polypeptide or nucleotide sequence. A substantially pure protein or nucleic acid will typically comprise about 85 to 100% (w/w) of a protein or nucleic acid sample, more usually about 95%, and preferably will be over about 99% pure. Protein or nucleic acid purity or homogeneity can be indicated by a number of means well known in the art, such as polyacrylamide gel electrophoresis of a protein sample, followed by visualizing a single polypeptide band on a polyacrylamide gel upon staining, or by agarose gel electrophoresis of a nucleic acid sample, followed by visualizing a single polynucleotide band on an agarose gel upon staining. "Staining" may either refer to the use of a-specific peptide or nucleic acid stains such as silver and Coomassie stains, or ethidium bromide and SYBR® stains, or may refer to the use of specific peptide or nucleic acid stains such as contacting the peptide with an antibody and visualizing the antibody using a labeled secondary antibody (e.g. conjugated to alkaline phosphatase) in the case of proteins or peptides, or contacting the nucleic acid with a complementary probe labeled for visualizing the presence of hybridization between the nucleic acid and the probe. For certain purposes higher resolution can be provided by using high performance liquid chromatography (HPLC) or a similar means for purification. Such methods are in the area of common general knowledge (see e.g. Katz, et al., 1998).

As used herein, "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, "regulatory sequences" may include, but are not limited to, promoters, translation leader sequences, introns, and polyadenylation recognition sequences.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

As used herein, the "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

As used herein, "RNA transcript" refers to the product resulting from RNA polymerase-catalyzed transcription of a DNA sequence. When the RNA transcript is a perfect complementary copy of the DNA sequence, it is referred to as the primary transcript. An RNA transcript is referred to as the mature RNA when it is an RNA sequence derived from post-transcriptional processing of the primary transcript. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

As used herein, the term "recombinant" refers to an artificial combination of two otherwise separated segments of sequence, e.g., by chemical synthesis or by the manipulation of isolated segments of nucleic acids by genetic engineering techniques.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. The term "expression", as used herein, refers to the production of a functional end-product e.g., an mRNA or a protein (precursor or mature).

As used herein, "antisense inhibition" or "antisense silencing" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

As used herein, the phrase "plant-expressible selectable or screenable marker" refers to a genetic marker functional in a plant cell. A selectable marker (e.g. a kanamycin resistance gene) allows cells containing and expressing that marker to grow under conditions unfavorable to growth of cells not expressing that marker. A screenable marker (e.g. a beta-galactosidase gene) facilitates identification of cells which express that marker.

As used herein, the term "inbred", "inbred plant" is used in the context of the present invention, this also includes any single gene conversions of that inbred. The term single allele converted plant as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "infective dosage" is defined as a dosage of viral particles or virus nucleic acid capable of infecting a plant, which dosage may vary between plants and between viruses tested. Infection in this way may be achieved by mechanical inoculation of purified virus particles or virus nucleic acid on plants.

As used herein, the term "resistant", or "resistance", describes a plant, line or cultivar that shows fewer or reduced symptoms to a biotic pest or pathogen than a susceptible (or more susceptible) plant, line or variety to that biotic pest or pathogen. These terms are variously applied to describe plants that show no symptoms as well as plants showing some symptoms but that are still able to produce marketable product with an acceptable yield. Some lines that are referred to as resistant are only so in the sense that they may still produce a crop, even though the plants may appear visually stunted and the yield is reduced from that of uninfected plants. As defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest or pathogen can depend on the analytical method employed. Resistance is defined by the ISF as the ability of a plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under nomial pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance is well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 5 being the resistance score applied to the most resistant plants (e.g., no symptoms, or with the least symptoms), and 1 the score applied to the plants with the most severe symptoms, then a line is rated as being resistant when at least 75% of the plants have a resistance score at a 3, 4, or 5 level, while susceptible lines are those having more than 25% of the plants scoring at a 1 or 2 level. If a more detailed visual evaluation is possible, then one can use a scale from 1 to 10 so as to broaden out the range of scores and thereby hopefully provide a greater scoring spread among the plants being evaluated. Alternatively or in addition to such visual evaluations, the evaluation can also be performed by determining the virus bio-density in a plant or plant part through molecular biological methods, such as protein hybridization (e.g., ELISA, measuring viral protein density) and/or nucleic acid hybridization (e.g., RT-PCR, measuring viral RNA density). A plant is resistant to the virus strain if it has a virus RNA and/or protein density that is about 50%, about 40%, about 30%, about 20%, about 10%, about 5%, about 2%, about 1%, about 0.1%, about 0.01%, about 0.001%, or about 0.0001% of the RNA and/or protein density in a susceptible plant.

As used herein, the term "full resistance" is referred to as complete failure of the virus to develop after infection, and may either be the result of failure of the virus to enter the cell (no initial infection) or may be the result of failure of the virus to multiply in the cell and infect subsequent cells (no subliminal infection, no spread). The presence of full resistance may be determined by establishing the absence of viral particles or viral RNA in cells of the plant, as well as the absence of any disease symptoms in said plant, upon exposure of said plant to an infective dosage of virus (i.e. after 'infection'). Among breeders, this phenotype is often referred to as "immune". "Immunity" as used herein thus refers to a form of resistance characterized by absence of viral replication even when virus is actively transferred into cells by e.g. electroporation.

As used herein, the term "partial resistance" is referred to as reduced multiplication of the virus in the cell, as reduced (systemic) movement of the virus, and/or as reduced symptom development after infection. The presence of partial resistance may be determined by establishing the systemic presence of low titres of viral particles or viral RNA in the plant and the presence of decreased or delayed disease-symptoms in said plant upon exposure of said plant to an infective dosage of virus. Virus titres may be determined by using a quantitative detection method (e.g. an ELISA method or a quantitative reverse transcriptase-polymerase chain reaction (RT-PCR)). Among breeders, this phenotype is often referred to as "intermediate resistant."

As used herein, the term "hypersensitive" refers to a foam of resistance whereby the infection remains local and does not systemically spread, for instance due to local necrosis of infected tissue or lack of systemic movement beyond inoculated tissue. Hypersensitive plants show local, but severe disease symptoms and the local presence of the virus can be established in such plants.

As used herein, the term "tolerant" is used herein to indicate a phenotype of a plant wherein disease-symptoms remain absent upon exposure of said plant to an infective dosage of virus, whereby the presence of a systemic or local viral infection, virus multiplication, at least the presence of viral genomic sequences in cells of said plant and/or genomic integration thereof can be established. Tolerant plants are therefore resistant for symptom expression but symptomless carriers of the virus. Sometimes, viral sequences may be present or even multiply in plants without causing disease symptoms. This phenomenon is also known as "latent infection". Some DNA and RNA viruses, may become undetectable following a primary infection only to reappear later and produce acute disease. In latent infections, the virus may exist in a truly latent non-infectious occult form, possibly as an integrated genome or an episomal agent (so that viral particles cannot be found in the cytoplasm, while PCR protocols may indicate the present of viral nucleic acid sequences) or as an infectious and continuously replicating agent. A reactivated virus may spread and initiate an epidemic among susceptible contacts. The presence of a "latent infection" is indistinguishable from the presence of a "tolerant" phenotype in a plant.

As used herein, the term "susceptible" is used herein to refer to a plant having no or virtually no resistance to the virus resulting in entry of the virus into the plant's cells and multiplication and systemic spread of virus, resulting in disease symptoms. The term "susceptible" is therefore equivalent to "non-resistant". A susceptible plant exhibits normal virus titres in its cells upon infection. Susceptibility may thus be determined by establishing the presence of normal (i.e. relative to other viral infections in plants) titres of viral particles or of viral RNA in cells of the plant and the presence of normal disease symptoms in said plant upon exposure of said plant to an infective dosage of virus.

As used herein, the term "sensitive" reflects the symptomatic reaction of a susceptible plant upon virus infection. The reaction or symptoms can be more or less severe depending on the level of sensitivity of the plant. If the plant is injured or even killed by the virus, said plant is qualified as "sensitive".

As used herein the term "MeSMV-resistant," is to be interpreted as referring to the resistance of a plant, plant tissue, or plant cell, in particular a cucurbit, to the establishment of an infection, or the establishment of a disease caused by a the new virus as defined in the present invention, unless expressly stated or intended otherwise.

As used herein, the term "MeSMV-specific" as used herein refers to a nucleic acid sequence, or an amino acid sequence having a sequence that is specific for the genus of viruses comprising the virus as defined in the present invention. With the term "specific" is meant that the nucleic acid sequence or the amino acids sequence is capable of hybridizing specifically under stringent hybridization conditions to the nucleic acid of said virus, or to an antibody of a MeSMV-specific protein of the said virus.

As used herein, the term "sample" includes a sample from a plant, a plant part, a plant cell, or from a transmission vector, or a soil, water or air sample.

As used herein, the term "transmission vector" as used herein refers to the disease-spreading agent or substance.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus. As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the term "mass selection" refers to a form of selection in which individual plants are selected and the next generation propagated from the aggregate of their seeds.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the terms "mutant" or "mutation" refer to a gene, cell, or organism with an abnormal genetic constitution that may result in a variant phenotype.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "self-crossing", "self pollinated" or "self-pollination" means the pollen of one flower on one plant is applied (artificially or naturally) to the ovule (stigma) of the same or a different flower on the same plant.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

As used herein, the term "transposition event" refers to the movement of a transposon from a donor site to a target site.

As used herein, the term "variety" refers to a subdivision of a species, consisting of a group of individuals within the species that are distinct in form or function from other similar arrays of individuals.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

As used herein, the term "QTL" is used herein in its art-recognized meaning. A QTL may for instance comprise one or more genes of which the products confer the genetic resistance. Alternatively, a QTL may for instance comprise regulatory genes or sequences of which the products influence the expression of genes on other loci in the genome of the plant thereby conferring the virus resistance. The QTLs of the present invention may be defined by indicating their genetic location in the genome of the respective virus-resistant accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

Plant Diseases Resistance

Plant disease resistance is crucial to the reliable production of food, and it provides significant reductions in agricultural use of fuel, water, land and other inputs. There are numerous examples of devastating plant disease impacts (see Irish Potato Famine, Chestnut blight) as well as recurrent severe plant disease issues (see Rice blast, Soybean cyst nematode, Citrus canker). It is estimated that diseases typically reduce plant yields by at least 10% every year.

Plant disease resistance derives both from pre-formed defenses and from infection-induced responses mediated by the plant immune system. Disease outcome is determined by the three-way interaction of the pathogen, the plant, and the environmental conditions (an interaction known as the disease triangle). Defense-activating compounds can move cell-to-cell and systemically through the plant vascular system, but plants do not have circulating immune cells so most cell types in plants retain the capacity to express a broad suite of antimicrobial defenses. Although obvious qualitative differences in disease resistance can be observed when some plants are compared (allowing classification as "resistant" or "susceptible" after infection by the same pathogen strain at similar pathogen pressure in similar environments), a gradation of quantitative differences in disease resistance is more typically observed between plant lines or genotypes.

Preformed structures and compounds that contribute to resistance in plants include, but are not limited to, plant cuticle/surface, plant cell walls, antimicrobial chemicals (e.g., glucosides, saponins), antimicrobial proteins, enzyme inhibitors, detoxifying enzymes that break down pathogen-derived toxins, receptors that perceive pathogen presence and active inducible plant defenses. Inducible plant defenses that are generated upon or after infection include, but are not limited to, cell wall reinforcement (e.g., increased callose, lignin, suberin, cell wall proteins), antimicrobial chemicals (e.g., reactive oxygen species such as hydrogen peroxide, peroxynitrite, or complex phytoalexins such as genistein or camalexin), antimicrobial proteins (e.g., defensins, thionins, or pathogenesis-related (PR) proteins), antimicrobial enzymes (e.g., chitinases, beta-glucanases, peroxidases), hypersensitive response (e.g., rapid host cell death response associated with defense mediated by resistance genes), and post-translation gene silencing.

Plant immune systems show some mechanistic similarities and apparent common origin with the immune systems of insects and mammals, but also exhibit many plant-specific characteristics. As in most cellular responses to the environment, defenses are activated when receptor proteins directly or indirectly detect pathogen presence and trigger ion channel gating, oxidative burst, cellular redox changes, protein kinase cascades, and/or other responses that either directly activate cellular changes (such as cell wall reinforcement), or activate changes in gene expression that then elevate plant defense responses.

Plants, like animals, have a basal immune system that includes a small number of pattern recognition receptors that are specific for broadly conserved microbe-associated molecular patterns (MAMPs, also called pathogen-associated molecular patterns or PAMPs). Examples of these microbial compounds that elicit plant basal defense include bacterial flagellin or lipopolysaccharides, or fungal chitin. The defenses induced by MAMP perception are sufficient to repel most potentially pathogenic microorganisms. However, pathogens express effector proteins that are adapted to allow them to infect certain plant species; these effectors often enhance pathogen virulence by suppressing basal host defenses.

Importantly, plants have evolved R genes (resistance genes) whose products allow recognition of specific pathogen effectors, either through direct binding of the effector or by recognition of the alteration that the effector has caused to a host protein. R gene products control a broad set of disease resistance responses whose induction is often sufficiently rapid and strong to stop adapted pathogens from further growth or spread. Plant genomes each contain a few hundred apparent R genes, and the R genes studied to date usually confer specificity for particular strains of a pathogen species. As first noted by Harold Flor in the mid-20th century in his formulation of the gene-for-gene relationship, the plant R gene and the pathogen "avirulence gene" (effector gene) must have matched specificity for that R gene to confer resistance. The presence of an R gene can place significant selective pressure on the pathogen to alter or delete the corresponding avirulence/effector gene. Some R genes show evidence of high stability over millions of years while other R genes, especially those that occur in small clusters of similar genes, can evolve new pathogen specificities over much shorter time periods.

The use of receptors carrying leucine-rich repeat (LRR) pathogen recognition specificity domains is common to plant, insect, jawless vertebrate and mammal immune systems, as is the presence of Toll/Interleukin receptor (TIR) domains in many of these receptors, and the expression of defensins, thionins, oxidative burst and other defense responses (Jones and Dangl. 2006 The plant immune system. *Nature* 444:323-329. Ting et al. 2008. NLRs at the intersection of cell death and immunity. *Nat Rev Immunol.* 8:372-379. which are incorporated herein by reference in their entireties).

Some of the key endogenous chemical mediators of plant defense signal transduction include salicylic acid, jasmonic acid or jasmonate, ethylene, reactive oxygen species, and nitric oxide. Numerous genes and/or proteins have been identified that mediate plant defense signal transduction (Hammond-Kosack and Parker, 2003, Deciphering plant-pathogen communication: fresh perspectives for molecular resistance breeding. Curr Opin Biotechnol. 14:177-193). Cytoskeleton and vesicle trafficking dynamics help to target plant defense responses asymmetrically within plant cells, toward the point of pathogen attack.

Plant immune systems can also respond to an initial infection in one part of the plant by physiologically elevating the capacity for a successful defense response in other parts of the plant. These responses include systemic acquired resistance, largely mediated by salicylic acid-dependent pathways, and induced systemic resistance, largely mediated by jasmonic acid-dependent pathways. Against viruses, plants often induce pathogen-specific gene silencing mechanisms mediated by RNA interference. These are primitive forms of adaptive immunity.

In a small number of cases, plant genes have been identified that are broadly effective against an entire pathogen species (against a microbial species that is pathogenic on other genotypes of that host species). Examples include barley MLO against powdery mildew, wheat Lr34 against leaf rust, and wheat Yr36 against stripe rust. An array of mechanisms for this type of resistance may exist depending on the particular gene and plant-pathogen combination. Other reasons for effective plant immunity can include a relatively complete lack of co-adaptation (the pathogen and/or plant lack multiple mechanisms needed for colonization and growth within that host species), or a particularly effective suite of pre-formed defenses.

Disease resistant plants offer an effective, safe, and relatively less expensive method of controlling many crop diseases. Most available commercial varieties of crop plants bear resistance to at least one, and often several, pathogens. Resistant or immune varieties are critically important for low-value crops in which other controls are unavailable, or their expense makes them impractical. Much has been accomplished in developing disease-resistant varieties of field crops, vegetables, fruits, turf grasses, and ornamentals.

Resistance to disease varies among plants. It may be either total (a plant is immune to a specific pathogen) or partial (a plant is tolerant to a pathogen, suffering minimal injury). The two broad categories of resistance to plant diseases are vertical (specific) and horizontal (nonspecific). A plant variety that exhibits a high degree of resistance to a single race, or strain, of a pathogen is said to be vertically resistant; this ability usually is controlled by one or a few plant genes. Horizontal resistance, on the other hand, protects plant varieties against several strains of a pathogen, although the protection is not as complete. Horizontal resistance is more common and involves many genes.

Several means of obtaining disease-resistant plants are commonly employed alone or in combination. These include, but are not limited to, introduction from an outside source, selection, and induced variation. All three may be used at different stages in a continuous process; for example, varieties free from injurious insects or plant diseases may be introduced for comparison with local varieties. The more promising lines or strains are then selected for further propagation, and they are further improved by promoting as much variation as possible through hybridization or special treatment. Finally, selection of the plants showing greatest promise takes place.

Methods used in breeding plants for disease resistance are similar to those used in breeding for other characters. It is necessary to know as much as possible about the nature of inheritance of the resistant characters in the host plant and the existence of physiological races or strains of the pathogen.

The techniques of genetic engineering can be used to manipulate the genetic material of a cell in order to produce a new characteristic in an organism. Genes from plants, microbes, and animals can be recombined (recombinant DNA) and introduced into the living cells of any of these organisms. The production of pathogen-resistant transgenic plants has been achieved by this method. Certain genes are inserted into the plant's genome that confer resistance to such pathogens as viruses, fungi, and insects.

Tospovirus

The Tospoviruses are a genus (Tospovirus) of negative RNA virus found within the family Bunyaviridae. They are the sole group of plant infecting viruses in this family, as all other described members of the Bunyaviridae infect animals. The genus takes its name from the discovery of Tomato Spotted Wilt Virus (TSWV) in Australia in 1915. It remained the only member of the family until the early 1990's when genetic characterization of viruses discovered in plants became more common. There are now at least twenty viral "species" in the family with more being recorded and described on a relatively regular basis. Together, these viruses have been documented infecting over eight hundred different plant species from 82 different families. Three tospoviruses, Tomato Spotted Wilt Virus (TSWV), Impatiens necrotic spot virus (INSV), and Iris yellow spot virus (IYSC) are known to occur in US.

Non-limiting examples of Tospovirus include, Capsicum chlorosis virus, Calla Lily Chlorotic Spot Virus, Chrysanthemum stem necrosis virus, Groundnut bud necrosis virus, Groundnut ringspot virus, Goundnut yellow spot virus, Impatiens necrotic spot virus, Iris yellow spot virus, Melon yellow spot virus, Peanut bud necrosis virus, Peanut chlorotic fan virus, Peanut yellow spot virus, Tomato chlorotic spot virus, Tomato spotted wilt tospovirus, Tomato yellow fruit ring virus, Tomato yellow ring virus, Watermelon bud necrosis virus, Watermelon silver mottle virus, and Zucchini lethal chlorosis tospovirus.

Tospoviruses have a unique particle morphology, genome organization and expression strategies. The pleomophic virus particles are about 80-120 nm in size and have surface projections composed of two viral glycoproteins. This virus has a single stranded RNA genome with negative polarity, therefore it is classified as a Class V virus ((−)ssRNA viruses). The structure of the genome resembles that of the genus Phlebovirus. The genome is linear and is about 15 kb in size to about 20 kb in size, with the average being about 17 kb in sizes to about 18 kb in size. Specific examples of the genome size are about 16.9 kb, about 17.0 kb, 17.1 kb, about 17.2 kb, about 17.3 kb, about 17.4 kb, about 17.5 kb, about 17.6 kb, about 17.7 kb, about 17.8 kb, about 17.9 kb, about 18.0 kb and/or about 18.1 kb. Even more specific examples of genome size are about 17.2 kb in size to about 17.6 kb in size. Tospovirus spp. all possess a tripartite, single-stranded RNA genome with a negative, or antisense expression strategy (34). Genomic RNAs are encapsidated by nucleocapsid, proteins (N) and enveloped by a lipoprotein membrane (34). The three genome segments are referred to as small (S), medium (M), and large (L). Each genome RNA is encapsidated by multiple copies of the viral nucleocapsid protein to form ribonucleoprotein structures also known as nucleocapsids. The S segment encodes a nonstructural protein and the M and S RNA segments encode for proteins in an antisense orientation protein (NSs) in the viral sense (2,11,31) and the N protein in the viral complementary sense (11). The M segment encodes in the viral sense a nonstructural protein (NSm) (28,29) and, in the viral complementary sense, the precursor of the two membrane glycoproteins (27,38,39). The L segment encodes the RNA-dependent RNA polymerase protein in the viral complementary sense (11).

Tospoviruses are arboviruses usually vectored by a thrips. At least ten species of thrips belonging to family Thripidae have been confirmed as vectors for the transmission of thirteen or more tospoviruses. *Frankliniella occidentalis* (Western flower thrips), *F. fusca* (tobacco thrips) and *Thrips tabaci* (onion thrips) are the major vectors of the tospoviruses currently present in the US. The thrips vectors are not closely related, implying an independent origin of infection for each thrips, possibly transmitted horizontally through shared hosts. There may be other species of thrips competent to transmit similar viruses, but they have not been documented on crops of economic significance. Recent research concludes that thrips can only be infected by tospovirus during the larval phases of development, as pupation and metamorphosis separate the connection between the salivary glands and the infected muscle tissue of the mid-gut. Adults transmit the virus from infected salivary glands, and uninfected adults will not transmit the virus. Obviously, controlling the infection by limiting transmission from infected plants to larval thrips or by preventing adult dispersal from infected plants are key strategies in preventing an epidemic of the disease.

Infection with the virus results in spotting and wilting of the plant, reduced vegetative output, and eventually death. No antiviral cures have been developed for plants infected with a Tospovirus, and infected plants should be removed from a field and destroyed in order to prevent the spread of the disease. There are a large number of plant families that are known to be affected by viruses of the Tospovirus genus. These include, but are not limited to, both food crops (such as peanuts, watermelons, melon, squash, cucumber, capsicums, tomatoes, zucchinis, et al.) as well as ornamental species which are important to flower farms (calla lily, impatiens, crysanthemums, iris, et al.). Plant families that can be infected by Tospovirus include, but are not limited to, Acanthaceae, Agavaceae, Aizoaceae, Amaranthaceae, Amaryllidaceae, Apocynaceae, Araceae, Araliaceae, Aristolochiaceae, Asclepiadaceae, Balsaminaceae, Begoniaceae, Boraginaceae, Bromeliaceae, Cactaceae, Campanulaceae, Cannaceae, Caricaceae, Caryophyllaceae, Chenopodiaceae, Compositae (Asteraceae), Convolvulaceae, Crassulaceae, Cruciferae, Cucurbitaceae, Dipsacaceae, Euphorbiaceae, Gentianaceae, Geraniaceae, Gesneriaceae, Gramineae, Iridaceae, Labiatae, Leguminosae, Liliaceae, Lobeliaceae, Malvaceae, Martyniaceae, Nolanaceae, Onagraceae, Paeoniaceae, Papaveraceae, Pedaliaceae, Phytolaccaceae, Plantaginaceae, Plumbaginaceae, Polemoniaceae, Polygonaceae, Portulacaceae, Primulaceae, Ranunculaceae, Rubiaceae, Saxifragaceae, Scrophulariaceae, Solanaceae, Tetragoniaceae, Tropaeolaceae, Umbelliferae, Urticaceae, Verbenaceae, Violaceae, and Zygophyllaceae.

Leaf symptoms caused by most tospoviruses consist of necrotic (brown) and/or chlorotic (yellow) rings or ring patterns on many hosts. Necrotic and/or chlorotic lesions may also form on stems. Wilting and/or purpling of leaves and stems can occur. Young leaves of TSWV-infected tomatoes frequently turn bronze and later develop numerous small, dark brown lesions. TSWV-infected tomato plants may develop a one-sided growth habit, leaves may be severely distorted, or the entire plant maybe be stunted with drooping leaves suggestive of a vascular wilt. Growing tips may also die. Plants infected early in the season may produce no fruit, whereas plants infected after fruit set has occurred may produce fruits with chlorotic or necrotic ringspots. Green fruit have slightly raised areas with faint concentric rings; on ripe fruit, these turn into obvious rings which become red and white or red and yellow. The chlorotic lesions are difficult to observe at the 'breaker' stage of picking but are highly visible at full color. Similar undesirable fruit color may be observed with TSWV infection of pepper. INSV infection induces chlorotic or necrotic ringspots on leaves and stems. IYSV infection leads to chlorotic (sometimes with a distinct diamond shape) or necrotic lesions on the seed stalk and bulb leaves of onion, chive and leek.

Currently, both diagnosis and treatment of Tospovirus are problematic in agriculture. Early symptoms of infection are difficult to diagnose. In young infected plants the characteristic symptoms consist of inward cupping of leaves and leaves that develop a bronze cast followed by dark spots. As the infection progresses additional symptoms develop which include dark streaks on the main stem and wilting of the top portion of the plant. Fruit may be deformed, show uneven ripening and often have raised bumps on the surface. Once a plant becomes infected the disease cannot be controlled. Control of this disease is difficult. One of the reasons for this is that the wide host range allows the virus to successfully overseason from one crop to the next. To prevent spread of the virus infected plants should be immediately removed away from neighboring plants. Control of insects, especially thrips, is important to reduce spread of the virus by vectors. Thus, it is very important that such virus infection is accurately detected as early as possible. Insecticides have been used to reduce thrips larval development and thus limit secondary virus spread. The use of UV reflective mulches, acibenzolar-S-methyl (Actigard), and insecticides has provided excellent management of TSWV in commercial tomato fields.

Cucurbitaceae

Cucurbitaceae is a plant family commonly known as melons, gourds or cucurbits and includes crops like cucumbers, squashes (including pumpkins), luffas, melons and watermelons. The family is predominantly distributed around the tropics, where those with edible fruits were amongst the earliest cultivated plants in both the Old and New Worlds.

Cucurbits is a general term for the species of the Cucurbitaceae family, comprising about 140 genera and more that 900 species of which only a few are cultivated. The world production of cucurbit crops is in excess of 115 million metric tons, on a total area harvested of 6.9 million hectares throughout the world (FAPSTAT database, 2000). The world production and the harvested area has increased three-fold in the last three decades.

Most of the plants in this family are annual vines but there are also woody lianas, thorny shrubs, and trees (*Dendrosicyos*). Many species have large, yellow or white flowers. The stems are hairy and pentangular. Tendrils are present at 90° to the leaf petioles at nodes. Leaves are exstipulate alternate simple palmately lobed or palmately compound. The flowers are unisexual, with male and female flowers on different plants (dioecious) or on the same plant (monoecious). The female flowers have inferior ovaries. The fruit is often a kind of berry called a pepo.

There are about more than 140 extant genera in Cucurbitaceae, including over 900 species. Cucurbitaceae includes subfamily Zanonioideae and subfamily cucurbitoideae.

Subfamily Zanonioideae includes subtribe Fevilleinae (e.g., *Fevillea*), subtribe Zanoniinae (e.g., *Alsomitra, Zanonia, Siolmatra, Gerrardanthus, Zygosicyos, Xerosicyos, Neoalsomitra*), subtribe Gomphogyninae (e.g., *Hemsleya,*

*Gomphogyne, Gynostemma*), subtribe Actinostemmatinae (e.g., *Bolbostemma, Actinostemma*), and subtribe Sicydiinae (e.g., *Sicydium Chalema Pteropepon Pseudosicydium Cyclantheropsis*).

Subfamily cucurbitoideae includes subtribe Dendrosicyinae (e.g., *Kedrostis, Dendrosicyos, Corallocarpus, Ibervillea, Tumamoca, Halosicyos, Ceratosanthes, Doyerea, Trochomeriopsis, Seyrigia, Dieterlea, Cucurbitella, Apodanthera, Guraniopsis, Melothrianthus, Wilbrandia*), subtribe Guraniinae (e.g., *Helmontia, Psiguria, Gurania*), subtribe Cucumerinae (e.g., *Melancium, Cucumeropsis, Posadaea, Melothria, Muellarargia, Zehneria, Cucumis* (including: *Mukia, Dicaelospermum, Cucumella, Oreosyce*, and *Myrmecosicyos*)), subtribe Trochomeriinae (e.g., *Solena, Trochomeria, Dactyliandra, Ctenolepsis*), tribe Schizopeponeae (e.g., *Schizopepon*), subtribe Thladianthinae (e.g., *Indofevillea, Siraitia, Thladiantha, Momordica*), subtribe Telfairiinae (*Telfaria*), subtribe Hodgsoniinae (*Hodgsonia*), subtribe Ampelosicyinae (e.g., *Ampelosicyos, Peponium*), subtribe Trichosanthinae (e.g., *Gymnopetalum, Trichosanthes, Tricyclandrai*), subtribe Herpetosperminae (e.g., *Cephalopentandra, Biswarea, Herpetospermum, Edgaria*), subtribe Benincasinae (e.g., *Cogniauxia, Ruthalicia, Lagenaria, Benincasa, Praecitrullus, Citrullus, Acanthosicyos, Eureiandra, Bambekea, Nothoalsomitra, Coccinia, Diplocyclos, Raphidiocystis, Lemurosicyos, Zombitsia, Ecballium, Bryonia*), subtribe Luffinae (*Luffa*), tribe Cucurbiteae (e.g., *Cucurbita, Sicana, Tecunumania, Calycophysum, Peponopsis, Anacaona, Polyclathra, Schizocarpum, Penelopeia, Cionosicyos, Cayaponia, Selysia, Abobra*), subtribe cyclantherinae (e.g., *Hanburia, Echinopepon, Marah, Echinocystis, Vaseyanthus, Brandegea, Apatzingania, Cremastopus, Elateriopsis, Pseudocyclanthera, Cyclanthera, Rytidostylis*), and subtribe Sicyinae (e.g., *Sicyos, Sicyosperma, Parasicyos, Microsechium, Sechium, Sechiopsis, Pterosicyos*).

Cucumber

The cucumber (*Cucumis sativus* L.) is a widely cultivated plant in the gourd family Cucurbitaceae. Non-limiting examples of cucumber varieties include, English cucumbers, East Asian cucumbers, Mediterranean cucumbers. Armenian cucumbers (a.k.a. yard long), Persian cucumbers, Beit Alpha cucumbers, pickling cucumbers, slicers, manroot (wild cucumber), *Dosakai* (yellow cucumber in India), *Kekiri* (Srilanka), and c-thru-cumber (a thin-skinned variety which reportedly does not require peeling).

Squash

Squash is the common name for a collection of plants that produce edible seeds, fruits and flowers. Squashes generally refer to four species of the genus *Cucurbita* native to Mexico and Central America, also called marrows depending on variety or the nationality of the speaker. It is also natively grown in other parts of North America, and in Europe, India, and Australia. In North America, squash is loosely grouped into summer squash or winter squash, as well as autumn squash (another name is cheese squash) depending on whether they are harvested as immature vegetables (summer squash) or mature vegetables (autumn squash or winter squash). Gourds are from the same family as squashes. Well known types of squash include the pumpkin and zucchini. Giant squash are derived from *Curcurbita maxima* and are routinely grown to weights nearing those of giant pumpkins. Non-limiting examples of squash species include, *C. maxima* (winter squash), *C. mixta* (cushaw squash), *C. moschata* (winter crookneck squash, e.g., butternut squash), *C. pepo* var. *pepo* (most pumpkins, acorn squash), *C. pepo* var. *melopepo* (e.g., summer squash (bush summer squash zucchini)), ambercup squash, autumn cup squash, banana squash, buttercup squash, carnival squash, delicata squash, gold nugget squash, kabocha squash, spaghetti squash, sweet dumpling squash, hubbard squash, and turban squash.

Winter squashes are the mature fruits of three Cucurbit species: *Cucurbita maxima, Cucurbita moschata* and *Cucurbita pepo*. Fruit from winter squash varieties are grown to physiological maturity and typically stored for consumption during the winter months or used for ornamental purposes. Examples of common winter squashes are acorn, butternut, hubbard, and spaghetti squash, as well as the Halloween type pumpkins. *Cucurbita maxima* is one of the most diverse domesticated species, perhaps with more cultivated forms than any other crop. This species originated in South America from the wild *C. maxima* ssp. andreana over 4000 years ago. Different squash types of this species were introduced into North America as early as the 16th century. By the early 19th century, at least three varieties are known to have been commercially introduced in North America from seeds obtained from Native Americans. Secondary centers of diversity include India, Bangladesh, Bunna, and possibly the southern Appalachians. Non-limiting examples of *Cucurbita maxima* include, Banana squash, Buttercup squash, Jarrandale pumpkin, Kabocha, Lakota squash, Arikara squash, and Hubbard squash. Candyroaster landrace *Cucurbita moschata* is a species that includes some varieties of squash and pumpkin. *C. moschata* squash are generally more tolerant of hot, humid weather than *C. maxima* or *C. pepo*. They also generally display a greater resistance to disease and insects, especially to the squash vine borer. Non-limiting examples of *C. moschata* include, butternut squash, Dickinson field pumpkin, Kentucky field pumpkin, Long Island cheese pumpkin, Calabaza pumpkin, Seminole pumpkin, Neck pumpkin, and Long of Naples squash. *Cucurbita pepo* is the main economic squash species. It includes varieties of squash, gourd, and pumpkin. Non-limiting example of *Cucurbita pepo* include, Acorn squash, Delicata squash, Gem squash, Heart of gold squash, Pattypan squash, Some types of Pumpkin, Spaghetti squash, Sweet dumpling squash, Yellow crookneck squash, Yellow summer squash, and Zucchini.

Most summer squash varieties are *Cucurbita pepo*, and their fruits are typically harvested and consumed at an immature stage. The flowers of summer squash can also be harvested for consumption. There are many types of summer squash, including yellow crookneck, yellow straightneck, scallop, Lebanese, and green and gray zucchini. Green zucchini is the type of *C. pepo* squash preferred by consumers in Europe and many parts of the North America, as well as in other regions. Unlike winter squashes, summer squash fruit have a short shelf life, and are typically consumed within days of harvest. Because of the extended ability to ship produce over long distances there are some markets where the terms "summer" and "winter" squash no longer reflect a restriction on availability and all types can be found in these markets year round.

Melon

Melon is a name given to various members of the Cucurbitaceae family with fleshy fruit. Melon can refer to either the plant or the fruit, which is a false berry. Many different cultivars have been produced, particularly of muskmelons. The plant grows as a vine. Although the melon is a fruit, some varieties may be considered "culinary vegetables".

Non-limiting example of melons include, bitter melon (genus *Momordica*), winter melon (genus *Benincasa*); watermelon (genus *Citrullus*); horned melon (*Cucumis metuliferus*); European cantaloupe and Algerian melon (*cucumis melo cantalupensis*); Canary melon, Casaba, Kolkhoznitsa melon, Hami melon, honeydew, Navajo Yellow, Piel de Sapo/

Santa Claus, sugar melon, tigger (tiger) melon, and Japanese melons (*Cucumis melo indodorus*); true muskmelons, with netted skin. Examples include Bailan melon, North American cantaloupe, Galia, Ogen, Persian, Sharlyn melons (*Cucumis melo reticulatus*); Crenshaw (Casaba X Persian), Crane (Japanese X N.A. cantaloupe) (Modern crossbred varieties); *Cucumeropsis mannii*.

Watermelon

Watermelon (*Citrullus lanatus* (Thunb.) Matsum & Nakai, family Cucurbitaceae) refers to both fruit and plant of a vine-like (scrambler and trailer) herb originally from southern Africa and one of the most common types of melon. This flowering plant produces a special type of fruit known by botanists as a pepo, a berry, which has a thick rind (exocarp) and fleshy center (mesocarp and endocarp); pepos are derived from an inferior ovary and are characteristic of the Cucurbitaceae. The watermelon fruit, loosely considered a type of melon (although not in the genus *Cucumis*), has a smooth exterior rind (green, yellow, and sometimes white) and a juicy, sweet interior flesh (usually pink, but sometimes orange, yellow, red, and sometimes green if not ripe). There are more than twelve hundred varieties (see, Icebox watermelon seed sources, Washington State University, Retrieved on October 2009) of watermelon ranging in size from less than a pound, to more than two hundred pounds with flesh that is red, orange, yellow, or white. Some non-limiting examples of watermelon varieties include, Carolina cross, yellow crimson watermelon, orangeglo, Moon and Starts, Cream of Saskatchewan, Melitopolski, and densuke watermelon.

Isolated Virus Strain, Viral Nucleic Acid Sequences and Amino Acid Sequences

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information (http://www.hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (B) of 10, a cutoff of 100, M=5, N=−4, and a comparison of both strands. For amino acid sequences, the BLASTP program uses as defaults a word length (W) of 3, an expectation (B) of 10, and the BLOSUM62 scoring matrix (see Henikoff & Henikoff (1989) Proc. Natl. Acad. Sci, USA 89:10915).

Phylogenetic analysis based on the nucleotide sequence or the amino acid sequence can be performed to determine the relationships between the isolated virus and other viruses from the genera Tospovirus, which is presented in the Examples below. The results indicate that the isolated virus is within the Tospovirus species, but very distinct from any other known virus members. Thus, it is a novel isolated Tospovirus.

It is understood that homologies may be large when two sequences are compared over a small comparison window since local regions of sequence similarity can often be found when two long nucleotide sequences are compared. However, the skilled person is aware that sequence homology requires the establishment of common motifs between the sequences, among which the sequence identity may locally be as high as 35 to 100%, but may be as low as 10-20% in other parts of the sequence. Thus, when reference is made herein that a sequence has a nucleotide sequence and/or an amino acid sequence homology of at least 80% to any one of SEQ ID NOs: 1-14 this may refer to the sequence homology between regions amongst common motifs, where homology is greatest, but also between the other part the sequence. Note that sequence homologies may differ between the various genes or proteins in the genome (see Examples).

A MeSMV can be identified by the percentages of homology of the viral proteins or nucleic acids to be identified in comparison with viral proteins or nucleic acids identified herein. It is generally known that virus species, especially RNA virus species, often constitute a quasi species wherein a cluster of said viruses displays heterogeneity among its members. Thus it is expected that each isolate may have a somewhat different percentage homology with the sequences of the isolate as provided herein. Therefore, other viral isolates that exhibit sufficient sequence homology to viral proteins or nucleic acids identified herein are considered to belong to the same virus. Similar to other viruses, a certain degree of variation can be expected to be found between MeSMV viruses isolated from different sources. Suitable nucleic acid genome fragments each useful for phylogenetic analyses are for example any portion of nucleic acid sequences of the virus, such as the fragment of the Large, Medium and Small RNA fragments, or fragment of any genes (e.g., nonstructural protein NSs gene, nucleocapsid protein N gene, glycoprotein G gene, RNA dependent polymerase (RdRp) gene).

The term "variant" with respect to a protein refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. General texts which describe molecular biological techniques, which are applicable to the present invention, such as cloning, mutation, and the like, include Berger and Kimmel, Guide to Molecular Cloning Techniques, Methods in Enzymology, Vol. 152 Academic Press, Inc., San Diego, Calif. ("Berger"); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating the present genes etc. Thus, the invention also encompasses using known methods of protein engineering and recombinant DNA technology to improve or alter the characteristics of the proteins expressed in algae. Various types of mutagenesis can be used to produce and/or isolate variant nucleic acids that encode for protein molecules and/or to further modify/mutate the proteins of the present invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Methods of cloning said genes are known in the art. The gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Proteins of an isolated MeSMV may be separated by electrophoresis using for instance Tricine-SDS-PAGE (Schagger and Von Jagow, 1987) or Glycine-SDS-PAGE (Laemmli, 1970). Other electrophoresis systems that are capable of resolving the various proteins comprised in the virus isolate, or transcribed from its genome and expressed in a suitable expression system, may of course also be employed, such as non-denaturing gel electrophoresis. The area of the PAGE gel including the target protein may be excised and the target polypeptides may be eluted therefrom, for instance by using an Elutrap® device (Schleicher & Schuell, Dassel, Germany). A target protein may be identified by its mobility relative to reference polypeptides in a gel. To increase purity the eluted protein may be run on a second SDS-PAGE gel and eluted a second time. The protein or peptide contained in the excised gel fragment may then be eluted again and is suitable for use in immunization or in protein sequencing.

Proteins of an isolated MeSMV may also be purified by affinity chromatography using an antibody (such as a monoclonal antibody) that specifically binds to a protein of the present isolated virus. The antibody may be covalently coupled to solid supports such as celluloses, polystyrene, polyacrylamide, cross-linked dextran, beaded agarose or controlled pore glass using bifunctional coupling agents that react with functional groups on the support and functional groups (i.e., reactive amino acid side chains) on the antibody molecule. Such methods are readily available to the skilled person. The resulting antibody-bearing solid phase is contacted with purified or partially purified virus under reducing conditions using pH, ionic strength, temperature and residence times that permit the protein of interest to bind to the immobilized antibody. The virus or protein is eluted from the column by passing an eluent that dissociates hydrogen bonds through the bed. Buffers at specific pH or NaCl solutions above about 2 M are commonly used eluents.

Methods for carrying out affinity chromatography using antibodies as well as other methods for immunoaffinity purification of proteins (such as viral capsid proteins) are well known in the art (see e.g., Harlow and Lane, 1988).

Antibodies

Antibodies, either monoclonal or polyclonal, can be generated to a purified or partially purified protein or peptide fragment of the present isolated virus in a variety of ways known to those skilled in the art including injection of the protein as an antigen in animals, by hybridoma fusion, and by recombinant methods involving bacteria or phage systems (see Marks et al., 1992a; Marks et al., 1992b; Lowman et al., 1991; Lerner et al., 1992, each of which reference discloses suitable methods).

Antibodies against viral particles, proteins or peptides of the virus may be produced by immunizing an appropriate vertebrate, preferably mammalian host, e.g., rabbits, goats, rats, chicken and mice with the particles, proteins or peptides alone or in conjunction with an adjuvant. Usually two or more immunizations will be involved, and the blood or spleen will be harvested a few days after the last injection. For polyclonal antisera, the immunoglobulins may be precipitated, isolated and (affinity) purified. For monoclonal antibodies, the splenocytes will normally be fused with an immortalized lymphocyte, e.g., a myeloid line, under selective conditions for hybridomas. The hybridomas may then be cloned under limiting dilution conditions and their supernatants screened for antibodies having the desired specificity. Techniques for producing (monoclonal) antibodies and methods for their preparation and use in various procedures are well known in the literature (see e.g. U.S. Pat. Nos. 4,381,292, 4,451,570, and 4,618,577; Harlow and Lane, 1988; Ausubel, et al., 1998; Rose et al., 1997; Coligan et al., 1997). Typically, an antibody directed against a virus-associated protein will have a binding affinity of at least $1 \times 10^5$ to $1 \times 10^7 M^{-1}$.

Methods of Diagnosing Plants

Diagnostic means and methods can be employed in the detection of MeSMV virus in a plant. The detection of MeSMV is performed with reagents that are most specific for MeSMV virus. This by no means however excludes the possibility that less specific, but sufficiently cross-reactive reagents are used instead, for example because they are more easily available and sufficiently address the task at hand.

Methods of Detection Based on Immunological Detection

An immunological detection for the presence of one or more MeSMV-specific proteins can be accomplished by contacting a biological sample with one or more MeSMV-specific antibodies, under conditions for antibody binding, wherein the MeSMV-specific antibody binds to an MeSMV-specific amino acids in the biological sample and detecting the binding.

The detecting step can comprise an immunological detection method such as instance classical immunofluorescence (IF), immunohistochemical techniques or comparable antigen detection assays. For example, non-limiting examples of immunological detection tests include, precipitation and agglutination tests, ELISA, Western blot, RIA, immunogod labeling, immunosorbent electron microscopy (ISEM), and/or dot blot. In one embodiment, the ELISA is a direct antibody sandwich enzyme linked immunosorbent assay (DAS-ELISA). In another embodiment, the ELISA is a Lateral Flow test. Examples of types of immunoassays that can utilize antibodies of the invention are competitive and non-competitive immunoassays in either a direct or indirect format. Antibodies can be utilized in immunoassays in the liquid phase or bound to a solid phase carrier. In addition, the antibodies in these immunoassays can be detectably labeled in various ways. Those skilled in the art will know, or can readily discern, suitable immunoassay formats without undue experimentation. Assay formats are well known in the literature and are described, for example, in Harlow and Lane (Harlow, E. and Lane, D. *Antibodies: A Laboratory Manual*, Cold Spring Harbor Laboratory, Cold Spring Harbor, N.Y. 1988).

A variety of immunoassay formats may be used to select antibodies specifically reactive with a particular polypeptide according to the invention, such as MeSMV viral coat proteins. For example, solid-phase ELISA immunoassays are routinely used for this purpose. See Harlow and Lane (1988), for a description of immunoassay formats and conditions that can be used to determine selective binding.

Antibodies can be bound to many different carriers and used to detect the presence of the target molecules. Alternatively, antigens may be bound to many different carriers and used to detect the presence of the antibody. Examples of well-known carriers include glass, polystyrene, polypropylene, polyethylene, dextran, nylon, amylases, natural and modified celluloses, polyacrylamides, agarose and magnetite. The nature of the carrier can be either soluble or insoluble for purposes of the invention. Those skilled in the art will know of other suitable carriers for binding antibodies, or will be able to ascertain such using routine experimentation.

Western blot assays are described generally in Harlow and Lane (1988). According to this method the viral proteins (and other proteins in the virus preparation) are separated by gel electrophoresis and transferred to a solid phase (i.e., a membrane such as nitrocellulose). The immobilized antigen is subsequently reacted with an antibody and detection system (e.g., an alkaline phosphatase-conjugated second antibody). As will be apparent to those of skill, it will be advantageous to include appropriate negative and positive control materials in the assay.

ELISA is a biochemical technique used mainly in immunology to detect the presence of an antibody or an antigen in a sample. The ELISA has been used as a diagnostic tool in medicine and plant pathology, as well as a quality control check in various industries. In simple terms, in ELISA an unknown amount of antigen is affixed to a surface, and then a specific antibody is washed over the surface so that it can bind to the antigen. This antibody is linked to an enzyme, and in the final step a substance is added that the enzyme can convert to some detectable signal. Thus in the case of fluorescence ELISA, when light of the appropriate wavelength is shone upon the sample, any antigen/antibody complexes will fluoresce so that the amount of antigen in the sample can be inferred through the magnitude of the fluorescence.

Performing an ELISA involves at least one antibody with specificity for a particular antigen. The sample with an unknown amount of antigen is immobilized on a solid support (usually a polystyrene micro-titer plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates enabling much higher sensitivity. ELISA methods include, but are not limited to, indirect ELISA, Lateral Flow test, DAS-ELISA, competitive ELISA, reverse ELISA.

Lateral flow tests are also known as Lateral Flow Immunochromatographic Assays, which comprise a simple device intended to detect the presence (or absence) of a target analyte in sample (matrix). Most commonly these tests are used for medical diagnostics either for home testing, point of care testing, or laboratory use. Often produced in a dipstick format, Lateral flow tests are a form of immunoassay in which the test sample flows along a solid substrate via capillary action. After the sample is applied to the test it encounters a colored reagent which mixes with the sample and transits the substrate encountering lines or zones which have been pretreated with an antibody or antigen. Depending upon the analytes present in the sample the colored reagent can become bound at the test line or zone. Lateral Flow Tests can operate as either competitive or sandwich assays. In principle any colored particle can be used, however most commonly either latex (blue color) or nanometer sized particles of gold (red color) are used. The gold particles are red in color due to localized surface plasmon resonance. Fluorescent or magnetic labeled particles can also be used—however these require the use of an electronic reader to assess the test result. In sandwich assays, the sample first encounters colored particles which are labeled with antibodies raised to the target analyte. The test line will also contain antibodies to the same target, although it may bind to a different epitope on the analyte. The test line will show as a colored band in positive samples. In competitive assays, the sample first encounters colored particles which are labeled with the target analyte or an analogue. The test line contains antibodies to the target/its analogue. Unlabeled analyte in the sample will block the binding sites on the antibodies preventing uptake of the colored particles. The test line will show as a colored band in negative samples. In quantitative tests, most tests are intended to operate on a purely qualitative basis. However it is possible to measure the intensity of the test line to determine the quantity of analyte in the sample. Implementing a Magnetic immunoassay (MIA) in the lateral flow test fowl also allows for getting a quantified result.

RIA is a very sensitive technique used to measure concentrations of antigens (for example, hormone levels in the blood) without the need to use a bioassay. It was developed by Rosalyn Yalow and Solomon Aaron Berson in the 1950s. Although the RIA technique is extremely sensitive and extremely specific, it requires specialized equipment and is costly. It also requires special precautions, since radioactive substances are used. Therefore, today it has been largely supplanted by the ELISA method, where the antigen-antibody reaction is measured using colorimetric signals instead of a radioactive signal.

To perforin a radioimmunoassay, a known quantity of an antigen is made radioactive, frequently by labeling it with gamma-radioactive isotopes of iodine attached to tyrosine. This radiolabeled antigen is then mixed with a known amount of antibody for that antigen, and as a result, the two chemically bind to one another. Then, a sample of serum from a patient containing an unknown quantity of that same antigen is added. This causes the unlabeled (or "cold") antigen from the serum to compete with the radiolabeled antigen ("hot") for antibody binding sites. As the concentration of "cold" antigen is increased, more of it binds to the antibody, displacing the radiolabeled variant, and reducing the ratio of antibody-bound radiolabeled antigen to free radiolabeled antigen. The bound antigens are then separated from the unbound ones, and the radioactivity of the free antigen remaining in the supernatant is measured. Using known standards, a binding curve can then be generated which allows the amount of antigen in the patient's serum to be derived.

Dot blot (or Slot blot) is a technique in molecular biology used to detect biomolecules. It represents a simplification of the northern blot, Southern blot, or western blot methods. In a dot blot the biomolecules to be detected are not first separated by chromatography. Instead, a mixture containing the molecule to be detected is applied directly on a membrane as a dot. This is then followed by detection by either nucleotide probes (for a northern blot and Southern blot) or antibodies (for a western blot). The technique offers significant savings in time, as chromatography or gel electrophoresis, and the complex blotting procedures for the gel are not required. However, it offers no information on the size of the target biomolecule. Furthermore, if two molecules of different sizes are detected, they will still appear as a single dot. Dot blots therefore can only confirm the presence or absence of a biomolecule or biomolecules which can be detected by the DNA probes or the antibody.

Methods of Detection Based on Nucleic Acid Detection

The presence or absence of one or more MeSMV-specific nucleic acid sequences may be detected by extracting nucleic acids from a plant or plant part and detecting the presence or absence of one or more MeSMV-specific nucleic acids.

The MeSMV-specific nucleic acid sequences may be in one or more different regions. The regions may be of one or more different genes of a MeSMV. A suitable biological sample can be prepared by any method, wherein the sample contains a template selected from the group consisting of DNA, RNA, and otherwise, so long as the template fits the criteria for amplification purposes by those skilled in the art. For example, said the method can comprise amplification of said MeSMV-specific nucleic acid sequence with one or more MeSMV-specific primer sets. The amplification method used can be RT-PCR, wherein the RT-PCR is performed using a real time PCR technique. In another method, the detecting step comprises nucleic acid hybridization between a MeSMV-specific nucleic acid sequence with a MeSMV-specific probe. The nucleic acid hybridization may be a Northern blot or a Southern blot. One skilled in the art will be able to design suitable probe for this purpose.

By recombinant DNA technology it is possible to produce probes that directly or indirectly hybridize to the viral nucleic acids, (e.g., viral RNA, complement thereof, or cDNA produced therefrom by reverse transcription), which can be used in assays for the detection of the virus. Nucleic acid amplification techniques allow the amplification of fragments of viral nucleic acids, which may be present in very low amounts.

The oligonucleotide primers for RT-PCT may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di- or tri-ester method, the diethylphosphoramidate method and the solid support method disclosed in e.g. U.S. Pat. No. 4,458,066. The primers may be labeled, if desired, by incorporating means detectable by for instance spectroscopic, fluorescence, photochemical, biochemical, immunochemical, or chemical means.

Template-dependent extension of the oligonucleotide primer(s) is catalyzed by a polymerizing agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, T4 DNA polymerase, and Taq DNA polymerase. The reaction conditions for catalyzing DNA synthesis with these DNA polymerases are known in the art.

The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

In order to develop nucleic acid-based detection methods, virus-specific sequences must be determined for which primers or probes may then be developed. For example, to detect MeSMV by nucleic acid amplification and/or probe hybridization, the viral genomic RNA was isolated from purified virus, reverse transcribed into cDNA and directly cloned and/or sequenced. Using either the cloned nucleic acid as a hybridization probe, using sequence information derived from the clone, or by designing degenerate primers based on the amino acid sequence of the MeSMV, nucleic acid hybridization probes and/or nucleic acid amplification primers may be designed an used in a detection assay for detecting the presence of the virus in a sample as defined herein.

Methods in which nucleic acids are detected can in principle be performed by using any nucleic acid amplification method, such as the Polymerase Chain Reaction (PCR; Mullis and Faloona, 1987; U.S. Pat. Nos. 4,683,195; 4,683,202; and 4,800,159) or by using amplification reactions such as Ligase Chain Reaction (LCR; Barany, 1991; EP 0 320 308), Self-Sustained Sequence Replication (3SR; Guatelli et al., 1990), Strand Displacement Amplification (SDA; Walker et al., 1992; U.S. Pat. Nos. 5,270,184 and 5,455,166), Transcriptional Amplification System (TAS; Kwoh et al., 1989), Q-Beta Replicase (Lizardi et al., 1988), Rolling Circle Amplification (RCA; U.S. Pat. No. 5,871,921), Nucleic Acid Sequence Based Amplification (NASBA; Compton, 1991), Cleavase Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of nucleic acids.

MeSMV is an RNA virus, a suitable detection method may comprise isolating the viral nucleic acids from a sample, for instance from an infected plant, a plant suspected to be infected, by using methods known per se to the skilled person (e.g. Chomczynski and Sacchi, 1987; Boom et al., 1990) or commercially available systems (e.g. the RNeasy total RNA isolation kit or RNeasy plant RNA isolation kit from QIAGEN GmbH, Hilden, Germany, or the High-Pure-RNA-Isolation-Kit® (Roche Diagnostics, a division of F. Hoffmann-La Roche Ltd, Basel, Switzerland).

Total RNA may for instance be extracted from a plant, or any part of a plant, e.g., leaf material or protoplasts of plant cells and the total RNA, or specifically the viral genomic RNA, or a part thereof, may then be reverse transcribed into cDNA by using for instance an Auian myeloblastosis virus (AMV) reverse transcriptase or Moloney murine leukemia virus (M-MuLV) reverse transcriptase. A suitable method may for instance include mixing into a suitable aqueous buffering system (e.g. a commercially available RT buffer) a suitable amount of total RNAs (e.g. 1 to 5 µg), a suitable amount (e.g. 10 pmol) of a reverse transcription primer, a suitable amount of dNTPs and the reverse transcriptase, denaturing the nucleic acids by boiling for 1 min, and chilling them on ice, followed by reverse transcription at for instance 45° C. for 1 h as recommended for the specific reverse transcriptase used, to obtain cDNA copies of the viral sequences.

As a reverse transcription primer a polynucleotide according to the present invention may be used, for instance an 18-25 nt oligonucleotide comprising a nucleotide sequence complementary to the MeSMV genomic sequence or preferably at least capable of hybridizing under stringent conditions to other MeSMV-specific fragments thereof. Alternatively, an A-specific polyT primer (oligo dT primer) may be used in order to start reverse transcription from polyA RNA motifs. In another embodiment, random primers can be used.

Following the RT-step, the cDNA obtained may be PCR amplified by using for instance Pfu and Taq DNA polymerases and amplification primers specific for the viral genomic cDNA sequences. Also complete commercially available systems may be used for RT-PCR (e.g. the Access and AccessQuick™ RT-PCR Systems of Promega (Madison Wis., USA), or the Titan™ One Tube RT-PCR System or two-step RT-PCR systems provided by Roche Diagnostics (a division of F. Hoffmann-La Roche Ltd, Basel, Switzerland)).

In order to amplify a nucleic acid sequence with a small number of mismatches to one or more of the amplification primers, an amplification reaction may be performed under conditions of reduced stringency (e.g. a PCR amplification using an annealing temperature of 38° C., or the presence of 3.5 mM $MgCl_2$). The person skilled in the art will be able to select conditions of suitable stringency.

The primers herein are selected to be "substantially" complementary (i.e. at least 65%, at least 70%, at least 80%, at least 90%, at least 95% perfectly complementary) to their target regions present on the different strands of each specific sequence to be amplified. It is possible to use primer sequences containing e.g. inositol residues or ambiguous bases or even primers that contain one or more mismatches when compared to the target sequence. In general, sequences that exhibit at least 65%, at least 70%, at least 80%, at least 90%, at least 95%, at least 99% homology with the target DNA or RNA oligonucleotide sequences, are considered suitable for use in a method of the present invention. Sequence mismatches are also not critical when using low stringency hybridization conditions. The detection of the amplification products can in principle be accomplished by any suitable method known in the art. The amplified fragments may be directly stained or labeled with radioactive labels, antibodies, luminescent dyes, fluorescent dyes, or enzyme reagents. Direct DNA stains include for example intercalating dyes such as alcidine orange, ethidium bromide, ethidium monazite or Hoechst dyes. Alternatively, the DNA or RNA fragments may be detected by incorporation of labeled dNTP bases into the synthesized fragments. Detection labels which may be associated with nucleotide bases include e.g. fluorescein, cyanine dye, digoxigenin (DIG) or bromodeoxyuridine (BrdUrd).

When using a probe-based detection system, a suitable procedure for use in the present invention may for example comprise an enzyme immunoassay (EIA) format (Jacobs et al., 1997). For performing a detection by manner of the EIA procedure, either the forward or the reverse primer used in the amplification reaction may comprise a capturing group, such as a biotin group for immobilization of target DNA PCR amplicons on e.g. a streptavidin coated microtiter plate wells or streptavidin coated Dynabeads® (Dynal Biotech, Oslo, Norway) for subsequent EIA detection of target DNA-amplicons. The skilled person will understand that other groups for immobilization of target DNA PCR amplicons in an EIA format may be employed.

Probes useful for the detection of the target nucleic acid sequences as disclosed herein preferably bind only to at least a part of the nucleic acid sequence region as amplified by the nucleic acid amplification procedure. Also the complementary nucleotide sequences, whether DNA or RNA or chemically synthesized analogues, of the target nucleic acid may suitably be used as type-specific probes in a method of the invention, provided that such a complementary strand is amplified in the amplification reaction employed.

Suitable detection procedures for use herein may for example comprise immobilization of the amplicons and probing the nucleic acid sequences thereof by e.g. Northern and Southern blotting. Other formats may comprise an EIA format as described above. To facilitate the of binding, the specific amplicon probes may comprise a label moiety such as a fluorophore, a chromophore, an enzyme or a radio-label, so as to facilitate monitoring of binding of the probes to the reaction product of the amplification reaction. Such labels are well known to those skilled in the art and include, for example, fluorescein isothiocyanate (FITC), β-galactosidase, horseradish peroxidase, streptavidin, biotin, digoxigenin, $^{35}S$, $^{14}C$, $^{32}P$ or $^{125}I$. Other examples will be apparent to those skilled in the art.

Detection may also be performed by a so called reverse line blot (RLB) assay, such as for instance described by Van den Brule et al. (2002). For this purpose RLB probes are preferably synthesized with a 5' amino group for subsequent immobilization on e.g. carboxyl-coated nylon membranes. The advantage of an RLB format is the ease of the system and its speed, thus allowing for high throughput sample processing.

The use of nucleic acid probes for the detection of RNA or DNA fragments is well known in the art. Mostly these procedures comprise the hybridization of the target nucleic acid with the probe followed by post-hybridization washings. Specificity is typically the function of post-hybridization washes, the critical factors being the ionic strength and temperature of the final wash solution. For nucleic acid hybrids, the Tm can be approximated from the equation of Meinkoth and Wahl (1984): Tm=81.5° C.+16.6 (log M)+0.41 (% GC)−0.61 (% form)−500/L; where M is the molarity of monovalent cations, % GC is the percentage of guanosine and cytosine nucleotides in the nucleic acid, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, the hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, 1993; Ausubel et al., 1998.

Oligonucleotide probes for the detection of MeSMV-specific nucleic acids can be produced. The probes are selected to be "substantially" complementary to a single stranded RNA molecule, or to one of the strands of the double stranded nucleic acids generated by an amplification reaction of the invention. Preferably the probes are substantially complementary to the, optionally immobilized (e.g. biotin labeled) antisense strands of the amplicons generated from the target RNA or DNA.

It is allowable for detection probes of the present invention to contain one or more mismatches to their target sequence. In general, sequences that exhibit at least 65%, at least 70%, at least 75%, at least 80% homology with the target oligonucleotide sequences are considered suitable for use in a method of the present invention.

The detecting step can comprise amplification of one or more MeSMV-specific nucleic acid sequences, using one or more MeSMV-specific primer sets, and determining the presence or absence of said MeSMV-specific nucleic acid sequences. In one embodiment, the MeSMV-specific nucleic acid sequences can be of one or more different genes in the biological sample. The biological sample can be prepared by any method, wherein the sample contains a template selected from the group consisting of DNA, RNA, and otherwise, so long as the template fits the criteria for amplification purposes by those skilled in the art. The template can be RNA, and amplified through RT-PCR. The RT-PCR can be real time RT-PCR.

Alternatively, in the detection method based on nucleic acid detection, and the detecting step comprises detecting a MeSMV-specific nucleic acid sequence by nucleic acid hybridization. The MeSMV-specific nucleic acid sequence can be from purified RNA from MeSMV. The MeSMV-specific nucleic acid sequence can be from cDNA which is obtained by reverse-transcribing the MeSMV RNA. The probe for hybridization can be derived from any other nucleic acid sequence of MeSMV.

Method of Screening MeSMV Resistant or Susceptible Plants

The present invention provides a method of screening for a plant population, plant, plant tissue or plant cell that is resistant or susceptible to MeSMV, comprising:
a) growing said plant population, plant, plant tissue or plant cell;
b) challenging said plant population, plant, plant tissue or plant cell with an infective amount of the isolated virus strain of claim 1 or 2;
c) evaluating the resistance in the plant, plant, plant tissue and plant cell.

In one embodiment, said plant is a dicot. In another embodiment, said plant is a monocot. In one embodiment, said plant is a cucurbit crop. For example, the plant is a melon, a watermelon, a squash, or a cucumber, or a zucchini.

An infective dosage may vary between plants and between MeSMV-isolates tested. Theoretically, an amount of about 1 to 10, about 10 to 100, about 100 to 1000, about 1000-10000, or about 10000-100000 viral particles of said virus will be sufficient. Infection in this way may be achieved by mechanical inoculation of purified virus particles or virus nucleic acid on healthy plants. Alternatively, infection may be achieved by, for instance:
1) growing a healthy scion on a MeSMV-infected rootstock, or vice versa;
2) exposing a healthy plant to transmission vectors containing the virus (including infected plants, e.g. parasitic plants like cucurbit plants and *N. benthamiana*);
3) introducing into a healthy plant an expression vector harboring a coding region of the MeSMV virus genome;
4) use of agro-infectious clones, such as *Agrobacterium tumefaciens* strains containing an expression vector harboring a coding region of the MeSMV virus genome.

Thus, in the context of the present invention, methods for challenging a plant, plant part, or plant cell to an infective dosage of MeSMV are not limited to any particular method. For example, infection may comprise mechanical inoculation of the virus on healthy plants. In one embodiment, a portion of a diseased leaf may be rubbed directly onto a leaf of a plant that is to be challenged. In an alternative procedure, an inoculum may for instance be prepared by grinding virus-containing plant tissue, e.g., young leaves showing symptoms, with a mortar and pestle, or any other suitable type of homogeniser, in for instance a buffer suitable for inoculation (e.g. a 0.03 M phosphate buffer, pH 7.7). After grinding, the obtained homogenate (the sap) is preferably filtered, e.g. through cheese cloth. The sap may then be inoculation, for instance by gently contacting leaves with an amount of the sap. The leaves are preferably pre-treated in order to damage the lower epidermis and enhance entry of the virus. This may for instance be achieved by pre-dusting the leaves with carborundum powder. Excessive wounding is preferably avoided. For example, a carborundum powder is used having microscopically small angular particles of silicon carbide (400-500 mesh). Carborundum powder may also be added directly to the sap, in which case the pre-treatment is omitted. The sap may, for instance, be applied by the forefinger, a pad of sap-soaked foam or fabric (e.g., a sponge pad with scouring side), or even with the pestle used for grinding, a glass spatula, a stiff brush, or a spray gun. Another method of preparing inoculum containing MeSMV is, soaking virus-containing plant tissue in suitable solution for a period of time wherein sufficient amount of virus is released from said plant tissue.

A plant, plant part, or plant cell resistant to MeSMV may have at least one characteristics as described below:
1) disease-symptoms in said plant, plant part, or plant cell remain absent, delayed, reduced in severity, or more localized compared to a susceptible control plant, plant part, or plant cell.
2) MeSMV nucleic acid sequences are not present, or at least quantitatively reduced in density in said plant, plant part, or plant cell compared to a susceptible control plant, plant part, or plant cell.
3) MeSMV amino acids sequences are not present, or at least quantitatively reduced in density in said plant, plant part, or plant cell compared to a susceptible control plant, plant part, or plant cell.

To determine the severity of infection in a plant, quantitative and/or qualitative methods can be taken. In a non-limiting exemplary quantitative method, the period required for the development of certain level of disease symptom is compared. In a non-limiting exemplary qualitative method, after a certain period, the plant is inspected for symptom development.

In other embodiments, the presence/absence of the virus is detected in the plant, plant part, or plant cell, and used to measure the resistance level. Any method of virus detection in the art may in principle be used, such as the methods described above in the present invention. For instance, a method may be employed wherein an immunological detection of MeSMV-specific proteins by antibodies, and/or a nucleic detection of MeSMV-specific nucleic acid sequences by probe hybridization and/or amplification (e.g., RT-PCT). In one embodiment, the plant is resistant to MeSMV when one or more methods fail to detect the nucleic acids and/or amino acids of MeSMV, or when the nucleic acids and/or amino acids of MeSMV is detectable, but compared to that of a susceptible control plant, the nucleic acids and/or amino acids density in the test plant is statistically higher compared to the control plant. The skilled person will understand that for such methods it is important to decontaminate the surface of the test plant, in order to distinguish between a transmission vector, a tolerant test-plant and a resistant test plant.

In terms of severity of infection, the following results may be obtained. If, after successful inoculation (e.g. after the establishment of a plant-virus contact under conditions that would result in infection in a susceptible and sensitive control plant):
  i) disease-symptoms remain absent; or viral particles, or viral RNA cannot be detected, which indicates the plant is resistant;
  ii) disease-symptoms are delayed or reduced in severity; or systemic low titres of viral particles or viral RNA can be detected, indicates the plant is partially resistant;
  iii) disease-symptoms are severe, but remain local, limited to the inoculated leaf and do not systemically spread beyond inoculated tissue; or viral particles, or viral RNA can only be detected locally, indicates the plant is hypersensitive;
  iv) if disease-symptoms remain absent; and viral particles, or viral RNA can be detected, indicates the plant is tolerant.
  v) if the plant develops disease-symptoms and has high systemic virus titres, then the plant is susceptible and sensitive. Examples of such plants are the plants from which the virus of the present invention was isolated. These plants may serve as suitable control plants in methods of the present invention.

For the purpose of producing resistant plants, and from a viewpoint of phytosanitation, only outcomes i), ii) and iii) may be considered of interest. For the purpose of obtaining plants suitable for the production of symptomless crops and products, outcome iv) may also be of particular commercial interest.

In one embodiment, said method comprises a control plant, plant tissue or plant cell, the population of which is also challenged with the virus strain, under similar environmental conditions and pest or pathogen pressure. Resistance level of the screened plant, plant tissue or plant cell is compared to the resistance level of the control plant, plant tissue or plant cell. In one further embodiment, the control plant, plant tissue or plant cell is susceptible to the virus strain, and the screening is targeting a plant, plant tissue or plant cell that is more resistant to the virus strain compared to the control plant, plant tissue or plant cell. In another further embodiment, the control plant, plant tissue or plant cell is resistant to the virus strain, and the screening is targeting a plant, plant tissue or plant cell that is more susceptible to the virus strain compared to the control plant, plant tissue or plant cell.

In one embodiment, the evaluating step comprises visual observation to determine the severity of the virus infection, using a resistance scoring system. The resistance scoring system is well known in the art. A resistance scoring system can be used to evaluate the resistance of a plant by signing a resistance score to a plant which ranges from 1 to 3, 1 to 5, or 1 to 10, et al., depending the severity of the infection or symptoms. For example, in a resistance scoring system 1 to 5, level 5 is the most resistant level (or the least symptomatic level), level 1 is the least resistant level (or the most symptomatic level), and level 3 is the intermediate level. A plant population is resistant if the it has about 50%, about 55%, about 60%, about 65%, about 70%, about 75%, about 80%, about 85%, about 90%, about 95%, or about 100% of the plants in the least symptomatic levels of 4 and 5. In one embodiment, a plant population is some resistant to the virus if it has greater than 60% of the plants in the least symptomatic levels of 4 and 5. In one embodiment, a plant population is obviously resistant to the virus if it has great than 70% of the plants in the least symptomatic levels of 4 and 5. In one embodiment, a plant population is highly resistant to the virus if it has greater than 80% of the plants in the least symptomatic levels of 4 and 5. In one embodiment, a plant population is extremely resistant to the virus if it has greater than 90% of the plants in the least symptomatic levels of 4 and 5. A plant population is susceptible if the it has about 50%, about 55%, about 60%, about 65%, about 70%, about 75%, about 80%, about 85%, about 90%, about 95%, or about 100% of the plants in the most symptomatic levels of 1 and 2. In one embodiment, a plant population is some susceptible to the virus if it has greater than 60% of the plants in the most symptomatic levels of 1 and 2. In one embodiment, a plant population is obviously susceptible to the virus if it has great than 70% of the plants in the most symptomatic levels of 1 and 2. In one embodiment, a plant population is highly susceptible to the virus if it has greater than 80% of the plants in the most symptomatic levels of 1 and 2. In one embodiment, a plant population is extremely susceptible to the virus if it has greater than 90% of the plants in the most symptomatic levels of 1 and 2.

In another embodiment, said evaluating step comprises one or more molecular biological tests of virus density in the plants. In one embodiment, said molecular biological tests comprise testing the density of MeSMV-specific nucleic acid sequence and/or MeSMV-specific protein. For example, the molecular biological test can involve probe hybridization and/or amplification of nucleic acid (e.g., measuring viral nucleic acid density by Northern or Southern hybridization, RT-PCR) and/or immunological detection (e.g., measuring viral protein density, such as precipitation and agglutination tests, ELISA (e.g., Lateral Flow test or DAS-ELISA), Western blot, RIA, immunogod labeling, immunosorbent electron microscopy (ISEM), and/or dot blot). A plant is resistant to the virus strain if it has a virus nucleic acid and/or protein density that is about 50%, about 40%, about 30%, about 20%, about 10%, about 5%, about 2%, about 1%, about 0.1%, about 0.01%, about 0.001%, or about 0.0001% of the virus nucleic acid and/or protein density in a susceptible plant. For example, a plant population is some resistant to the virus if it has a virus RNA and/or protein density that is about 10% of the RNA and/or protein density in a susceptible plant. A plant population is obviously resistant to the virus if it has a virus RNA and/or protein density that is about 1% of the RNA and/or protein density in a susceptible plant. A plant population is highly resistant to the virus if it has a virus RNA and/or protein density that is about 0.1% of the RNA and/or protein density in a susceptible plant. A plant population is extremely resistant to the virus if it has a virus RNA and/or protein density that is about 0.01% of the RNA and/or protein density in a susceptible plant.

The procedure to perform a nucleic acid hybridization, an amplification of nucleic acid (e.g., RT-PCR) or an immunological detection (e.g., precipitation and agglutination tests, ELISA (e.g., Lateral Flow test or DAS-ELISA), Western blot, RIA, immunogod labeling, immunosorbent electron microscopy (ISEM), and/or dot blot tests) as described below is well-known by one skilled in the art.

In one embodiment, the evaluating step comprise RT-PCR (semi-quantitative or quantitative), wherein MeSMV-specific primers are used to amplify one or more MeSMV-specific nucleic acid sequences. In one embodiment, said MeSMV-specific nucleic acid sequences are from the same gene of MeSMV. In another embodiment, said MeSMV-specific nucleic acid sequences are from different genes of MeSMV. In one embodiment, said MeSMV-specific nucleic acid sequences are selected from the group consisting of SEQ ID NOs. 1-5, a portion of any one of SEQ ID NOs. 1-5, a nucleic acid sequence that is at least about 80% homology to any one of SEQ ID NOs. 1-5, and combination thereof. In one embodiment, the MeSMV-specific primers are selected from the group consisting of SEQ ID NOs. 10-14. In one embodiment, said RT-PCT is a real-time RT-PCT.

In another embodiment, the evaluating step comprise immunological detection (e.g., precipitation and agglutination tests, ELISA (e.g., Lateral Flow test or DAS-ELISA), Western blot, RIA, immunogod labeling, immunosorbent electron microscopy (ISEM), and/or dot blot), wherein one or more MeSMV-specific antibodies are used to detect one or more MeSMV-specific proteins. In one embodiment, said MeSMV-specific antibody is selected from the group consisting of polyclonal antibodies, monoclonal antibodies, and combination thereof. In one embodiment, said MeSMV-specific protein is selected from the group consisting of MeSMV NSs protein, N protein, Glycoprotein, RdRp, and combination thereof. In one embodiment, said MeSMV-specific amino acid is selected from the group consisting of SEQ ID NOs. 6-9, a portion of any one of SEQ ID NOs. 6-9, an amino acid that is at least about 80% homology to any one of SEQ ID NOs. 6-9, and combination thereof.

Reverse Transcription Polymerase Chain Reaction (RT-PCR) can be utilized in the present invention to determine the virus RNA density in a plant. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the cDNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 50° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cations concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using agarose gel electrophoresis and ethidium bromide (or other nucleic acid staining).

Conventional RT-PCR is a time-consuming technique with important limitations when compared to real time PCR techniques. This, combined with the fact that ethidium bromide has low sensitivity, yields results that are not always reliable. Moreover, there is an increased cross-contamination risk of the samples since detection of the PCR product requires the post-amplification processing of the samples. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general non specific DNA Binding Dyes such as SYBR Green I, TaqMan Probes and Molecular Beacons (including Scorpions).

The real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

MeSMV Resistant/Susceptible Plants

Once an MeSMV resistant or susceptible plant is isolated from the screening as described above, it can be used for many purposes. Thus, the present invention provides plants resistant or susceptible to the isolated virus of present invention. In one embodiment, said plant is a cucurbit germplasm. In a further embodiment, said cucurbit germplasm is selected from the group consisting of melon, watermelon, squash/pumpkin, cucumber, or zucchini.

The present invention also provides a tissue culture of the isolated plant population, plant, plant tissue or plant cell, wherein said tissue culture retains resistance to the isolated virus of present invention.

The present invention also provides a seed derived from the isolated plant population, plant, plant tissue or plant cell, wherein said seed can give rise to a plant that is also resistant to the isolated virus of present invention.

The present invention also provides a progeny derived from the isolated plant as described above, whether produced sexually or asexually, wherein said progeny retains resistance to the virus.

In one embodiment, an MeSMV resistant plant is used as a donor plant of genetic material which can be transferred to produce a recipient plant which has the transferred genetic material and is also resistant to MeSMV. Any suitable method known in the art can be applied to transfer genetic material from a donor plant to a recipient plant. In most cases, such genetic material is genomic material.

In one embodiment, at least the resistance-conferring parts of the donor plant's genome are transferred. In some cases, the resistance conferring part is a single locus in the genome. In other cases, the resistance conferring parts are multiple loci in the genome.

Thus, the present invention provides methods of isolating a nucleic acid sequence conferring the entire resistance to MeSMV from a MeSMV-resistant plant, plant tissue, or plant cell, comprising:
  a) crossing the isolated plant resistant to the isolated MeSMV as a donor with a suitable plant susceptible, or partially susceptible to MeSMV to get offspring plants as a mapping population;
  b) challenging said offspring plants with said virus and determining the resistance in said offspring plants;
  c) cloning the nucleic acid sequence. For example, by map-based cloning or association mapping.

One skilled in the art will know how to choose a suitable plant for crossing, and how to clone a nucleic acid sequence by map-based cloning (see, Varshney and Tuberisa, *Genomics-assisted crop improvement: Genomics application in crops, Volume 2 of Genomics-assisted Crop Improvement*, 2008, Springer, Loze and Wenzel, *Molecular marker systems in plant breeding and crop improvement*, 2007, Springer, ISBN. 3540740066 9783540740063; Kang, *Quantitative genetics, genomics, and plant breeding*, 2002, CABI, ISBN 0851996019, 9780851996011, each of which is incorporated herein by reference in its entirety). Such cloned nucleic acid sequence can be transformed into a plant susceptible to MeSMV to make it become resistant. Methods of plant transformation is well-known in the art, and described separately below. Alternatively, genome fragment comprising said nucleic acid from a donor plant which is resistant to MeSMV can be transferred to a recipient plant through any transferring and/or breeding method described separately below.

While the resistance conferring parts are multiple loci in the genome, a QTL (quantitative trait locus) mapping can be applied to determine the parts of the donor plant's genome conferring the MeSMV resistance.

Thus, the present invention provides methods of detecting a QTL associated with the resistance to MeSMV in a donor plant, comprising:

a) crossing the isolated plant resistant to the isolated virus of the present invention as a donor with a suitable plant that is susceptible to said virus to produce offspring plants;
  b) challenging one or more said offspring plants with an infective dosage of said virus;
  c) quantitatively determining the resistance in said one or more offspring plants;
  d) establishing a genetic linkage map that links the observed resistance to the presence of chromosomal markers of said donor plant in said one or more offspring plants;
  e) assigning to a QTL the contiguous markers on said map that are linked to enhanced disease resistance.

Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. level of resistance to virus) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait—these QTLs are often found on different chromosomes. Knowing the number of QTLs that explains variation in the phenotypic trait tells about the genetic architecture of a trait. It may tell that plant resistance to virus of the present invention is controlled by many genes of small effect, or by a few genes of large effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describe cis- and trans-controlling elements for the expression of often disease-associated genes. Observed epistatic effects have been found beneficial to identify the gene responsible by a cross-validation of genes within the interacting loci with metabolic pathway- and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping*. 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing a gene that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and do those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a low distance between markers on a chromosome. Comparing all recombination frequencies will result in the most logical order of the molecular markers on the chromosomes. This most logical order can be depicted in a linkage map (Paterson, 1996). A group of adjacent or contiguous markers on the linkage map that is associated to a reduced disease incidence and/or a reduced lesion growth rate pinpoints the position of a QTL.

The nucleic acid sequence of a QTL of the present invention may be determined by methods known to the skilled person. For instance, a nucleic acid sequence comprising said QTL or a resistance-conferring part thereof may be isolated from a MeSMV-resistant donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with the resistance to MeSMV in a donor plant can be transformed into a plant susceptible to MeSMV to make it become resistant. Methods of plant transformation is well-known in the art, and described separately below. Alternatively, genome fragment comprising said QTLs from a donor plant which is resistant to MeSMV can be transferred to a recipient plant through any transferring and/or breeding method described separately below.

Figure 6:
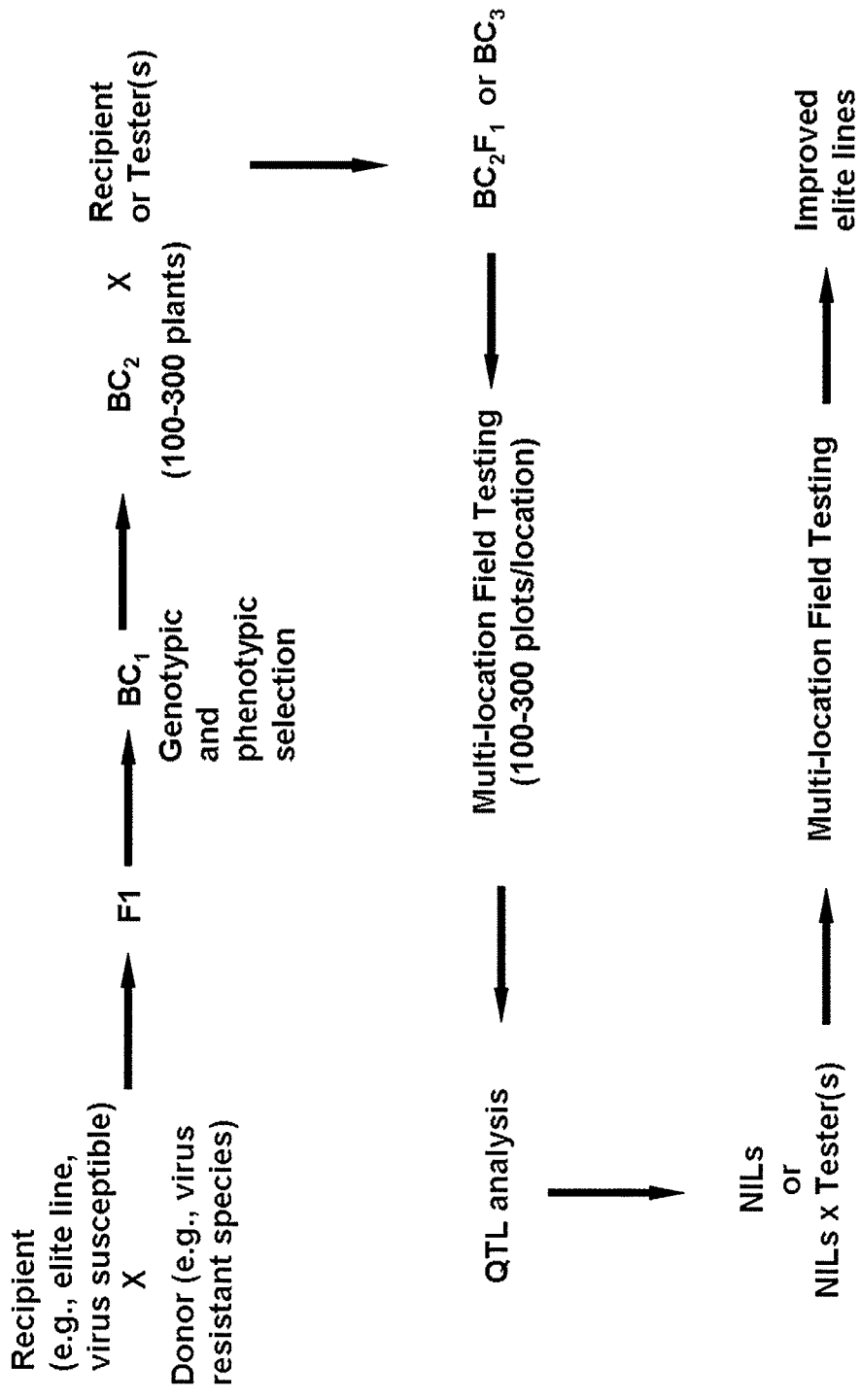
FIG. 6 depicts exemplary scheme of the Advanced Backcross QTL mapping strategy.

In one embodiment, an advanced backcross QTL analysis (AB-QTL) is used to discover the nucleotide sequence or the QTLs responsible for the resistance or susceptibility of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet.* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. A non-limiting exemplary scheme of AB-QTL mapping strategy is shown in FIG. 6. AB-QTL strategy was initially developed and tested in tomato, and has been adapted for use in other crops include rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred as near isogenic lines (NILs), introgression lines (ILs), backcross inbred lines (BILs), backcross recombinant inbred lines (BCRIL), recombinant chromosome substitution lines (RC-SLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises of a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL covers usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.*; 2(10): e245).

In one embodiment, when it is not determined that which parts of the donor plant's genome confer the MeSMV resistance, complete chromosomes of the donor plant are transferred. For example, the MeSMV resistant plant can serve as a male or female parent in a cross pollination to produce resistant offspring plants, wherein by receiving the genomic material form the resistant donor plant, the offspring plants are resistant to MeSMV.

In a method for producing a MeSMV-resistant plant, protoplast fusion can also be used for the transfer of resistance-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbred in nature, is tissue cultured into a hybrid plant exhibiting the desirable combination of traits. More specifically, a first protoplast can be obtained from a plant line that is resistant to MeSMV. For example, a protoplast from a MeSMV-resistant (melon, watermelon, squash or cucumber) line may be used. A second protoplast can be obtained from a susceptible second plant line, optionally from another plant species or variety, preferably from the same plant species or variety, that comprises commercially desirable characteristics, such as, but not limited to disease resistance, insect resistance, valuable fruit characteristics, etc. The protoplasts are then fused using traditional protoplast fusion procedures, which are known in the art to produce the cross.

Alternatively, embryo rescue may be employed in the transfer of resistance-conferring genomic material from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (see Pierik, 1999, *In vitro culture of higher plants*, Springer, ISBN 079235267x, 9780792352679, which is incorporated herein by reference in its entirety).

In addition, in one embodiment, a method for producing a MeSMV-resistant plant comprises grafting a susceptible recipient plant onto resistant rootstocks of MeSMV resistant plants, which is proved to be an effective methodology developed for intensive cultivation in the Far East (Lee and Oda, 2003, Grafting of herbaceous vegetable and ornamental crops, *Hort. Rev.* 28:61-124).

Method of Control Virus by Recombinant Virus Coat Protein

Traditional methods of controlling plant virus include used of virus-free seeds and insecticides for the control of insect vectors. These methods can only achieve some level of success in reducing the level of infection in a crop, but they are time consuming and relatively expensive. One alternative approach to control virus infection is though viral coat protein-mediated protection.

Expression of the coat protein from tobacco mosaic virus, alfalfa mosaic virus, cucumber mosaic virus, watermelon II mosaic virus, papaya ringspot virus, zucchini yellow mosaic virus and potato virus X in transgenic plants has resulted in plants which are resistant to infection by the respective virus (see, references Nos. 91 to 99). Thus, the present invention also provides method of controlling virus by expression one or more recombinant virus coat protein in a plant. In one embodiment, said virus is the isolated virus as described in the present invention. In one embodiment, said virus coat protein is a virus glycoprotein.

In further embodiments, one or more genes encoding virus coat proteins of the isolated virus, for example, gene encoding glycoprotein of the isolated virus, is operably linked to genetic regulatory sequence necessary for gene expression in a plant (e.g., a plant promoter) to form a chemic gene. As used herein, the phrase "plant promoter" refers to any promoter that is capable of initiating transcription in plant cells. The promoter can be constitutive, inducible or specific for an organ, tissue, or cell. In embodiment of the invention, the promoter directs expression of the coat protein gene in shoot vegetative organs/structures, such as leaf, stem and tuber. In one embodiment, the promoter directs expression of coat protein gene in roots. In another embodiment, the promoter directs expression coat protein gene in flowers or floral organs/structures, such as bracts, sepals, petals, stamens, carpels, anthers and ovules. In different embodiments, the promoter directs expression coat protein gene in seeds (e.g. embryo, endosperm, and seed coat) or fruit.

An expression vector comprising said chimeric gene which comprises one or more virus coat proteins is assembled, and then transformed to a plant, plant part, or plant cell which are then used to generate transgenic plants that are capable of expressing the viral coat protein, wherein the plant gets more resistant to viral infection compared to its non-transgenic counterpart. Detailed methods of making such plants resistant to plant virus by expression the virus's coat protein are described in U.S. Pat. Nos. 5,514,570, 6,002,072, 6,337,431, 6,750,382, and 6,903,248, which are incorporated herein by reference in their entireties.

Methods of Inducing Antiviral Response by RNA Silencing

Natural antiviral RNA silencing happens in plant as an evolutionary conserved way to fight against viral pathogen. Virus infection can triggers RNA silencing in infected plants that specifically targets the viral and homologous RNAs for degradation. For example, virus-specific siRNAs of both sense and antisense polarities is observed in plants infected with plus-strand RNA virus (Hamilton, et al., 1999. A species of small antisense RNA in posttranscriptional gene silencing in plants. *Science* 286, 950-952.).

The mechanism behind the RNA silencing is often known as post-transcriptional gene silencing (PTGS), which is initiated by dicer cleavage of the viral dsRNA replicative intermediates. The viral siRNA population may also contain siRNAs derived from Dicer cleavage of ssRNAs or dsRNAs generated by the action of a cellular RNA dependent RNA polymerase (Szittya et al., 2002, Short defective interfering RNAs of tombusviruses are not targeted but trigger post-transcriptional gene silencing against their helper virus. *Plant Cell* 14, 359-372, Vaistij et al., 2002, Spreading of RNA targeting and DNA methylation in RNA silencing requires transcription of the target gene and a putative RNA-dependent RNA polymerase. *Plant Cell* 14, 857-867).

Thus, the present invention provides a method of inducing antiviral response in a plant, wherein the plant becomes resistant to the isolated virus of the present invention. In one embodiment, said method is based on RNA interference technology.

RNA interference (RNAi) is the process of sequence-specific, post-transcriptional gene silencing or transcriptional gene silencing in animals and plants, initiated by double-stranded RNA (dsRNA) that is homologous in sequence to the silenced gene. It is known in the art that viral genomes, especially RNA viral genomes, are variable to accommodate resistance to changes in the environment. Thus, in order to knock down viral genome replication using RNAi, there is a need to identify conserved and unique regions in the viral genome. It is also important to ensure that conserved viral sequences targeted for silencing according to the invention be substantially non-homologous to any naturally occurring, normally functioning, host polynucleotide sequence, so that the dsRNA molecule does not adversely affect the function of any essential, naturally occurring, host polynucleotide sequences, when used in the methods of this invention. Such naturally occurring functional polynucleotide sequences include sequences that encode desired proteins, as well as sequences that are non-coding but essential regulatory sequences in a healthy host organism. Thus, the preferred RNA effector molecules useful in this invention must be sufficiently distinct in sequence from any host polynucleotide sequences for which function is intended to be undisturbed after any of the methods of this invention are performed. Computer algorithms may be used to define the essential lack of homology between the RNA molecule polynucleotide sequence and host, essential, normal sequences.

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to the RNA of MeSMV, or an opposite strand replication intermediate, or the anti-genomic plus strand or non-mRNA plus strand sequences of MeSMV. In one embodiment, said double-stranded RNA effector molecules are provided by providing to a plant, plant tissue, or plant cell an expression construct comprising one or more double-stranded RNA effector molecules. One skilled in the art will be able to design suitable double-strand RNA effector molecule based on the nucleotide sequences of MeSMV in the present invention.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

The expression construct comprising one or more double-stranded RNA effector molecules of the present invention can be transformed into a plant, wherein the plant becomes resistant to MeSMV by RNAi. The target sequence to be inhibited by the dsRNA effector molecule include, but are not limited to, coding region of MeSMV virus NSs gene, N gene, glycoprotein gene, and RNA dependent RNA polymerase gene, or any other sequence that is necessary for biogenesis of MeSMV. In one embodiment, said plant is a cucurbit crop, for example, a melon, a watermelon, a squash, a cucumber, or a zucchini.

Plant Transformation

The present invention provides methods of isolating resistance-conferring parts (e.g., a nucleic acid, or QTLs) conferring the resistance to the isolated virus of the present invention from a plant. Such resistance-conferring parts can be transformed into a plant variety of the same species, a closely-related species, or any other species, wherein the transgenic plant is more resistant compared to the non-transgenic plant of the same species.

Methods used for selection or screening of transformed cells, tissues and whole plants: 1) must be safe for the technicians or practitioners of transformation method, 2) must not introduce mutations in the donor or transforming DNA nor the recipient DNA, and 3) must not create environmental concerns, either with the process or with the resulting whole plant. By far the most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No.

4,399,216, WO8303259, U.S. Pat. No. 5,731,179, EP068730, WO9516031, U.S. Pat. No. 5,693,512, U.S. Pat. No. 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. No. 5,204,253, U.S. Pat. No. 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. No. 5,767,378; U.S. Pat. No. 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. No. 5,034,322, U.S. Pat. No. 6,174,724 and U.S. Pat. No. 6,255,560). In addition, several herbicides and herbicide resistance genes have been used for transformation purposes, including the bar gene, which confers resistance to the herbicide phosphinothricin (White et al., Nucl Acids Res 18: 1062 (1990), Spencer et al., Theor Appl Genet. 79: 625-631 (1990), U.S. Pat. No. 4,795,855, U.S. Pat. No. 5,378,824 and U.S. Pat. No. 6,107,549). In addition, the dhfr gene, which confers resistance to the anticancer agent methotrexate, has been used for selection (Bourouis et al., EMBO J. 2(7): 1099-1104 (1983).

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J. 3:835-846 (1984)) or the nopaline synthase signal (Depicker et al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host, preferably a broad host range prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736369; Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species. Currently, methods for gene transformation in Cucurbit plants are available, including but not limited to *Agrobacterium* mediated transformation and biolistic methods (e.g., a gene gun). A great number of melon, cucumber and squash genotypes have been transformed with different genes, as described by Victoriano Valpuesta (Fruit and vegetable biotechnology, Woodhead publishing in food science and technology, 2002, ISBN 1855734672, 9781855734678, which is incorporated herein by reference in its entirety), most of which is *Agrobacterium* mediated transformation (e.g., as described in Guis et al., "A reliable system for the transfoimation of cantaloupe chrentais melon (*Cucumis melo* L. var. *cantalupensis*) leading to a majority of diploid regenerants", *Scientia Hort.* 1999, 84:91-99; Gal-On et al., "Transgenic cucumbers harboring the 54-kDa putative gene of Cucumber fruit mottle mosaic tobamovirus are highly resistant to viral infection and protect non-transgenic scions from soil infection", *Transgenic Res.* 2005, 14:81-93).

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method, including cucurbitaceous species. For example, biolistic transformation has been used for the generation of transgenic cucumber and melon plants from highly embryogenic cell suspension cultures (Schulze et al., Biolistic transformation of cucumber using embryogenic suspension cultures: long-term expression of reporter genes. *Plant Sci.*, 1995, 112:197-206).

For more information of production of transgenic cucurbit crops, see Gaba et al. ("Invited review: Cucurbit biotechnology—the importance of virus resistance", 2004, *Invitro Cell. Dev. Biol.—Plant,* 40:346-358, which is incorporated herein by reference in its entirety).

Developed by ICI Seeds Inc. (Garst Seed Company) in 1993, WHISKERS™ is an alternative to other methods of inserting DNA into plant cells (e.g., the Biolistic® Gene Gun, *Agrobacterium tumefaciens*, the "Shotgun" Method, etc.); and it consists of needle-like crystals ("whiskers") of silicon carbide. The fibers are placed into a container along with the plant cells, then mixed at high speed, which causes the crystals to pierce the plant cell walls with microscopic "holes" (passages). Then the new DNA (gene) is added, which causes the DNA to flow into the plant cells. The plant cells then incorporate the new gene(s); and thus they have been genetically engineered.

The essence of the WHISKERS™ technology is the small needle-like silicon carbide "whisker" (0.6 microns in diameter and 5-80 microns in length) which is used in the following manner. A container holding a "transformation cocktail" composed of DNA (e.g., agronomic gene plus a selectable marker gene), embryogenic corn tissue, and silicon carbide "whiskers" is mixed or shaken in a robust fashion on either a dental amalgam mixer or a paint shaker. The subsequent collisions between embryogenic corn cells and the sharp silicon carbide "whiskers" result in the creation of small holes in the plant cell wall through which DNA (the agronomic gene) is presumed to enter the cell. Those cells receiving and incorporating a new gene are then induced to grow and ultimately develop into fertile transgenic plants.

Silicon carbide "whisker" transformation has now produced stable transformed calli and/or plants in a variety of plants species such as Zea mays. See, for example, U.S. Pat. Nos. 5,302,523 and 5,464,765, each of which is incorporated herein by reference in their entirety; Frame et al., The Plant Journal 6: 941-948 (1994); Kaeppler et al., Plant Cell Reports 9:415-418 (1990); Kaeppler et al., Theoretical and Applied Genetics 84:560-566 (1992); Petolino et al., Plant Cell Reports 19(8):781-786 (2000); Thompson et al., Euphytica 85:75-80 (1995); Wang et al., In Vitro Cellular and Developmental Biology 31:101-104 (1995); Song et al., Plant Cell Reporter 20:948-954 (2002); Petolino et al., Molecular Methods of Plant Analysis, In Genetic Transformation of Plants, Vol. 23, pp. 147-158, Springer-Verlag, Berlin (2003). Other examples include Lolium multiflorum, Lolium perenne, Festuca arundinacea, Agrostis stolonifera (Dalton et al., Plant Science 132:31-43 (1997)), Oryza sativa (Nagatani et al., Biotechnology Techniques 11:471-473 (1997)), and Triticum aestivum and Nicotiana tobacum (Kaeppler et al., Theoretical and Applied Genetics 84:560-566 (1992)). Even Chlamydomonas (see, for example, Dunahay, T. G., Biotechniques 15:452-460 (1993)) can be transformed with a "whiskers" approach. As it is currently practiced on higher plants, the "whisker" system is one of the least complex ways to transform some plant cells.

Genes successfully introduced into plants using recombinant DNA methodologies include, but are not limited to, those coding for the following traits: seed storage proteins, including modified 7S legume seed storage proteins (see, for example, U.S. Pat. Nos. 5,508,468, 5,559,223 and 5,576,203); herbicide tolerance or resistance (see, for example, De Greef et al., Bio/Technology 7:61 (1989); U.S. Pat. No. 4,940,835; U.S. Pat. No. 4,769,061; U.S. Pat. No. 4,975,374; Marshall et al. (1992) Theor. Appl. Genet. 83, 435; U.S. Pat. No. 5,489,520; U.S. Pat. No. 5,498,544; U.S. Pat. No. 5,554,798; Powell et al., Science 232:738-743 (1986); Kaniewski et al., Bio/Tech. 8:750-754 (1990)); Day et al., Proc. Natl. Acad. Sci. USA 88:6721-6725 (1991)); phytase (see, for example, U.S. Pat. No. 5,593,963); resistance to bacterial, fungal, nematode and insect pests, including resistance to the Lepidoptera insects conferred by the Bt gene (see, for example, U.S. Pat. Nos. 5,597,945 and 5,597,946; Johnson et al., Proc. Natl. Acad. Sci. USA, 86:9871-9875 (1989); Perlak et al., Bio/Tech. 8:939-943 (1990)); lectins (U.S. Pat. No. 5,276,269); flower color (Meyer et al., Nature 330:677-678 (1987); Napoli et al., Plant Cell 2:279-289 (1990); van der Krol et al., Plant Cell 2:291-299 (1990)); Bt genes (Voisey et al., supra); neomycin phosphotransferase II (Quesbenberry et al., supra); the pea lectin gene (Diaz et al., Plant Physiology 109(4): 1167-1177 (1995); Eijsden et al., Plant Molecular Biology 29(3):431-439 (1995)); the auxin-responsive promoter GH3 (Larkin et al., Transgenic Research 5(5):325-335 (1996)); seed albumin gene from sunflowers (Khan et al., Transgenic Research 5(3):179-185 (1996)); and genes encoding the enzymes phosphinothricin acetyl transferase, beta-glucuronidase (GUS) coding for resistance to the Basta® herbicide, neomycin phosphotransferase, and an alpha-amylase inhibitor (Khan et al., supra), each of which is expressly incorporated herein by reference in their entirety.

A transgenic plant fanned using Agrobacterium transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Assuming normal hemizygosity, selfing will result in maximum genotypic segregation in the first selfed recombinant generation, also known as the R1 or $R_1$ generation. The R1 generation is produced by selfing the original recombinant line, also known as the R0 or $R_0$ generation. Because each insert acts as a dominant allele, in the absence of linkage and assuming only one hemizygous insert is required for tolerance expression, one insert would segregate 3:1, two inserts, 15:1, three inserts, 63:1, etc. Therefore, relatively few R1 plants need to be grown to find at least one resistance phenotype (U.S. Pat. Nos. 5,436,175 and 5,776,760).

As mentioned above, self-pollination of a hemizygous transgenic regenerated plant should produce progeny equivalent to an F2 in which approximately 25% should be homozygous transgenic plants. Self-pollination and testcrossing of the F2 progeny to non-transformed control plants can be used to identify homozygous transgenic plants and to maintain the line. If the progeny initially obtained for a regenerated plant were from cross-pollination, then identification of homozygous transgenic plants will require an additional generation of self-pollination (U.S. Pat. No. 5,545,545).

Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly Apis mellifera L. or Megachile rotundata F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, Principles of Plant Breeding, John Wiley & Sons, Inc. (1960);

Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BAS). BAS, a.k.a. bulked segregation analysis, or bulk segregant analysis, is a method is described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences*, USA, 99:9828-9832) and Quarrie et al. (Quarrie et al., Bulk segregant analysis with molecular markers and its use for improving drought resistance in maize, 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

It should be understood that the examples and embodiments described herein are for illustrative purposes only and that various modifications or changes in light thereof will be suggested to persons skilled in the art and are to be included within the spirit and purview of this application.

DEPOSIT INFORMATION

A representative sample of the isolated MeSMV strain and the seeds of MeSMV resistant germplasm will be deposited.

To satisfy the enablement requirements of 35 U.S.C. 112, and to certify that the deposit of the isolated strain of the present invention meets the criteria set forth in 37 CFR 1.801-1.809, Applicants hereby make the following statements regarding the deposit of the isolated MeSMV strain and the resistant germplasm:

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the enforceable life of the patent, whichever is longer; and
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to the deposit.

EXAMPLES

Example 1

Materials and Methods

Virus Isolation and Maintenance

The virus was isolated from symptomatic honeydew melon (*C. melo*) plants during the melon-growing season in Mexico. Symptomatic plants were first checked for Cucurbit Potyviruses (ZYMV, PRSV, and WMV) and general Potyviruses, Cucumber Mosaic Virus (CMV), Squash Mosaic Virus (SQMV), Begomovirus and TSWV presence. Agdia® ELISA was used for the detection of ZYMV, PRSV, CMV, and SQMV, and AC Diagnostic ELISA kit was used for the detection of WMV. Detection of TSMV was performed by using specific double-antibody sandwich enzyme-linked immunosorbent assay (DAS-ELISA) using a commercial kit from Agdia (Elkhart, Ind.) and the DAS-ELISA kit as described before (24). The virus was mechanically transferred onto *C. melo* and *Nicotiana benthamiana* plants, and leaves were stored in liquid nitrogen to be used as the source of successive mechanical inoculations. To avoid the possibility of generating deletions or mutations in the virus genome, mechanical inoculations were limited to not more than three to four serial passages. The presence of Tospovirus sp.-like virions in infected plants was confirmed by electron-microscopic observation (Philips CM10, Eindoven, the Netherlands) of crude sap negatively stained in 0.5% aqueous uranyl acetate. DNA testing was also conducted for Begomovirus and general Potyvirus.

Host Range

Leaves of symptomatic *C. melo* and *N. benthamiana* plants showing strong mosaic symptoms 2 weeks post inoculation were homogenized with 50 mM phosphate buffer, pH 7, containing 1 mM Na-EDTA, 5 mM Na-DIECA, and 5 mM Na-thioglycolate (extraction buffer) and mechanically inoculated onto leaves of a series of herbaceous plants to determine the partial host range (Table 1, described below) as previously described (35). Plants were grown in an insect-proof glasshouse at a variable temperature between 20 and 25° C., and three individual plants for each species were inoculated when the first true leaves were fully expanded; symptoms were monitored after 1 and 4 weeks post inoculation. DAS-ELISA (as described below) was used to confirm the presence of MeSMV in both symptomatic and asymptomatic inoculated plants.

Nucleocapsid Purification and Antiserum Production

Viral nucleocapsids were purified from 100 g of MeSMV infected *N. benthamiana* plants following the method used for other Tospovirus spp. (23,24). The partially purified preparation was then layered on a 10- to 50-% sucrose gradient and centrifuged at 270,000 times g for 2 h. A band corresponding to the nucleocapsids was collected, and purity was assessed by electron microscopy and by Coomassie staining of the samples separated in 10% tris-tricine sodium dodecyl sulfate polyacrylamide gel electrophoresis (SDS-PAGE) as described (35).

A polyclonal antiserum was obtained from a 'New Zealand' rabbit injected intramuscularly with the nucleocapsid suspension. Purified nucleocapsid (1 mg) emulsified with Freund's complete adjuvant (1:1, vol/vol) was used for the first injection. Booster injections were given after 2, 4, and 6 weeks with incomplete Freund's adjuvant. Blood was collected three times, every 15 days, beginning 2 weeks from the second injection. Serum was separated after overnight incubation at 4° C. and cross-absorbed with healthy plant extract (*N. benthamiana*). Immunoglobulin G (IgG) was purified through affinity chromatography on protein G columns (Pharmacia, Skokie, Ill.) according to the manufacturer's instructions.

ELISA and Western Blot Analysis

The specificity of purified MeSMV-IgG was assessed by antigen-coated plate (ACP) ELISA using dilutions of infected and healthy plants (35). An aliquot of the IgG was conjugated with alkaline phosphatase using the glutaraldehyde two-step method and DAS-ELISA was performed as previously detailed (23).

For the Western blot analysis, purified nucleocapsid preparations or total leaf protein extracts were separated by 10% SDS-PAGE and transferred to 0.45-μm nitrocellulose parablot NCP membranes (Macherey-Nagel, Duren, Germany) as described (36). Purified IgGs diluted 1:1000 in TBS-Tween+7% dried skimmed milk were used as primary antibody, and anti-rabbit IgG conjugated with horseradish peroxidase (Sigma-Aldrich, St. Louis; dilution 1:5000 in TBS-Tween+7% dried skimmed milk) was used as the secondary antibody. Super Signal West Pico Chemiluminescent substrate (Pierce, Rockford, Ill.) was used following the manufacturer's instructions to detect the presence of bound secondary antibodies.

RNA Extraction, cDNA Cloning, and Sequence Analyses

Total RNA was extracted from purified nucleocapsids using TRIZOL reagent (Invitrogen, Carlsbad, Calif.) according to the manufacturer's instructions. The Universal RiboClone Synthesis System (Promega Corp., Madison, Wis.) was used to obtain complementary DNA (cDNA) following the protocol provided by the manufacturer for first- and second-strand synthesis. A step including adaptor ligation and further polymerase chain reaction (PCR) amplification of the cDNA was performed as previously described (37). Selected PCR fragments were purified (Geneclean; qBiogene, Irvine, Calif.) and cloned in pGEM-T easy vector (Promega Corp.), and white colonies were screened by PCR with M13 forward and reverse primers. Positive colonies were grown in 4 ml of Luria-Bertani with ampicillin at 0.05 mg/ml, and plasmids were purified with the QIAprep spin Miniprep kit (Qiagen, Hilden, Germany). Plasmid inserts were sequenced using the dideoxy chain terminator method (25).

In order to obtain the full-length S segment sequence, reverse transcription on purified viral RNAs was performed using the Thermoscript reverse-transcription (RT)-PCR System (Invitrogen) using random hexamers to prime cDNA synthesis. PCR was then performed using primers designed from initial S-segment genomic fragment sequences (Table 2). Selected PCR products were purified (Qiagen), cloned in pGEM-T Easy, and sequenced. The S segment 5' and 3' ends were cloned using the oligonucleotide J13 generic for Tospovirus ends as previously described (6) and internal specific primers (Table 2). Clustal X version 1.81 was used for multiple sequence alignments (32). Statistical significance was calculated by performing 100 replications of bootstrap re-sampling of the original alignment using SEQBOOT. Phylogenetic trees were constructed with the PROTML algorithm in the Phylip version 3.6 (10) using the Dayhoff substitution matrix, one randomized sequence-input order, the global rearrangement option, and a mixed heterogeneity among sites variation model (one invariable plus six Gamma rates). TREEPUZZLE 5.0 (30) was used to estimate the relative rate for each category. Trees were generated with TreeView (19). Amino acid sequences of the other Tospovirus spp.

used for the analysis were taken from GenBank, EMB, DDBJ, and PDB databases. RNA secondary structures were predicted using the MFold web server (41).

Survey of Mexican Cucurbits Crops

A survey of cucurbit crops across Mexico was carried out in four different regions, ranging from Sinaloa in the northwest to the state of Chiapas in the south. In all, 147 plants showing possible virus-caused symptoms (including *C. melo, Cucurbita pepo, Cucumis sativus*, and *Citrullus lanatus*) were collected and analyzed throughout the growing season (February to May) for the presence of the new Tospovirus sp. by using MeSMV-specific lateral flow (LF) devices. Commercial LF devices were prepared from the polyclonal nucleocapsid antibodies and used for the field survey. Symptomatic plant development stage ranged from flowering to ripe fruit ready for harvest. For confirmation of the serological analysis, RT-PCR was carried out on 30 RNA samples extracted from leaves as described above using the oligonucleotides MeSMV-2490F and MeSMV-2900R (Table 2), with 30 cycles of PCR using a denaturing step of 30 s at 94° C., an annealing step at 55° C. for 30 s, and a step for polymerase activity at 72° C. for 20 s. Ten samples (including positives and negatives by LF) were also analyzed by DAS-ELISA for further validation.

Example 2

Virion Morphology, Symptoms, and Partial Host Range

Enveloped pleomorphic particles with features typical for members of the Tospovirus genus were observed by electron microscopy of leaf extracts of symptomatic melon plants. Similar particles were seen from plants showing a variety of symptoms, including an early onset of mosaic and leaf blistering symptoms on honeydew melon leaves (FIG. 1A); advanced blistering, mosaic, and leaf deformation on honeydew melon (FIG. 1B); necrotic lesions on mature honeydew melon (FIG. 1C); and immature honeydew fruit exhibiting necrotic fruit splitting (FIG. 1D). No other virus-like particles were observed or detected by other methods, including DAS-ELISA, for the most common cucumo- and potyviruses present in the region, such as Watermelon mosaic virus (WMV), Zucchini yellow mosaic (ZYMV), and Cucumber mosaic virus (CMV). Some squash samples collected were positive for Papaya ringspot virus (PRSV). When leaves were used for mechanical inoculation of *N. benthamiana* and *Cucumis melo* plants, symptoms were clear on inoculated plants by 7 days post inoculation (dpi). In fact, severe symptoms similar to those seen on the original diseased plants, such as mosaic, leaf deformation, and growth arrest, were observed. MeSMV was able to systemically infect plants of *N. benthamiana, N. megalosiphon, Datura stramonium*, and *N. clevelandii*, and caused deformation, mosaic, or necrosis; the virus infection caused also chlorotic spots on *Emilia sonchifolia* plants. DAS-ELISA confirmed the presence of MeSMV in inoculated and un-inoculated leaves (Table 1). Interestingly, MeSMV did not infect the other two Cucurbitaceae spp. present in the host range study: *C. sativus* and *Cucurbita pepo* cv. Genovese.

TABLE 1

Partial host range analysis of Melon severe mosaic virus[a]

| | | Symptoms | | ELISA results | |
| --- | --- | --- | --- | --- | --- |
| | | Inoculated | | | |
| Family | Species | leaves | Systemic | Local | Systemic |
| Solanaceae | *Datura stramonium* | cll | 0 | + | − |
| | *Capsicum annum* cv. Q.A. | cll | 0 | + | − |
| | *C. chinense* 152225 | 0 | 0 | − | − |
| | *Solanum lycopersicum* cv. York | 0 | 0 | − | − |
| | *S. lycopersicum* cv. Marmande | 0 | 0 | − | − |
| | *Nicotiana clevelandii* | nll | Deformation/mosaic | + | + |
| | *N. megalosiphon* | nll | Necrosis/deformation | − | + |
| | *N. rustica* | 0 | 0 | + | − |
| | *N. tabacum* cv. White Burley | cll/nll | 0 | + | − |
| | *N. glutinosa* | nll | 0 | − | − |
| | *N. benthamiana* | cll/nll | Mosaic/deformation | + | + |
| | *Emilia sonchifolia* | 0 | Chlorotic spot | + | + |
| | *Petunia × hybrida* | nll | 0 | − | − |
| Cucurbitaceae | *Cucurbita pepo* cv. Genovese | 0 | 0 | − | − |
| | *Cucumis melo* | cll | Mosaic/deformation | + | + |
| | *Cucumis sativus* | 0 | 0 | − | − |
| Apocynaceae | *Vinca rosea* | 0 | 0 | − | − |
| Labiatae | *Ocimum basilicum* | 0 | 0 | − | − |
| Leguminosae | *Phaseolus vulgaris* cv. Saxa | 0 | 0 | − | − |
| Chenopodiaceae | *Chenopodium quinoa* | 0 | 0 | − | − |
| | *Chenopodium amaranticolor* | 0 | 0 | − | − |
| Amaranthaceae | *Beta vulgaris* | cll/nll | 0 | + | − |
| | *Gomphrena globosa* | 0 | 0 | + | − |

[a]Three individual plants for each species tested were mechanically inoculated when their first true leaves were fully expanded using leaf sap from symptomatic *Nicotiana benthamiana* and *Cucumis melo* leaves collected 2 weeks post inoculation. Host range results are based on visual evaluation and confirmed by double-antibody sandwich enzyme-linked immunosorbent assay (DAS-ELISA) results (visual evaluation was the same for each of the three plants and a mixed sample for each species was evaluated by DAS-ELISA). Cll = chlorotic local lesion; nll = necrotic local lesion; 0 = no symptom; + and − symbols correspond to infected/healthy ratio (I/H) of absorbance values above or below 3 in DAS-ELISA.

Example 3

Virus Purification and Serology

Figure 2:
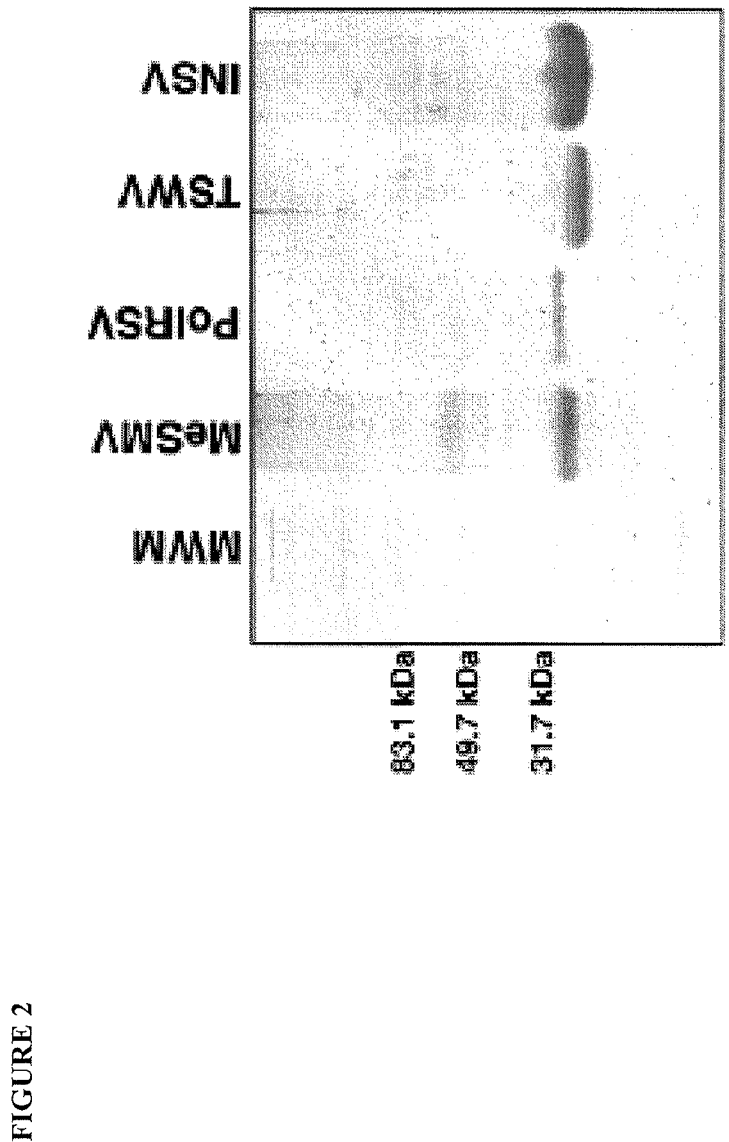
FIG. 2 depicts coomassie stained 10% polyacrylamide gel showing purified nucleocapsid proteins of MeSMV, Impatiens necrotic spot virus (INSV), Polygonum ringspot virus (PolRSV), and Tomato spotted wilt virus (TSWV). MWM, molecular weight markers. Numbers at left indicate positions for proteins of the respective size ($\times 10^{-3}$).

Typical Tospovirus spp.-like nucleocapsids were observed by electron microscopy in negatively stained purified MeSMV nucleocapsid preparations. The molecular weight of the N protein was estimated to be about 30 kDa by SDS-PAGE (FIG. 2).

Figure 3:
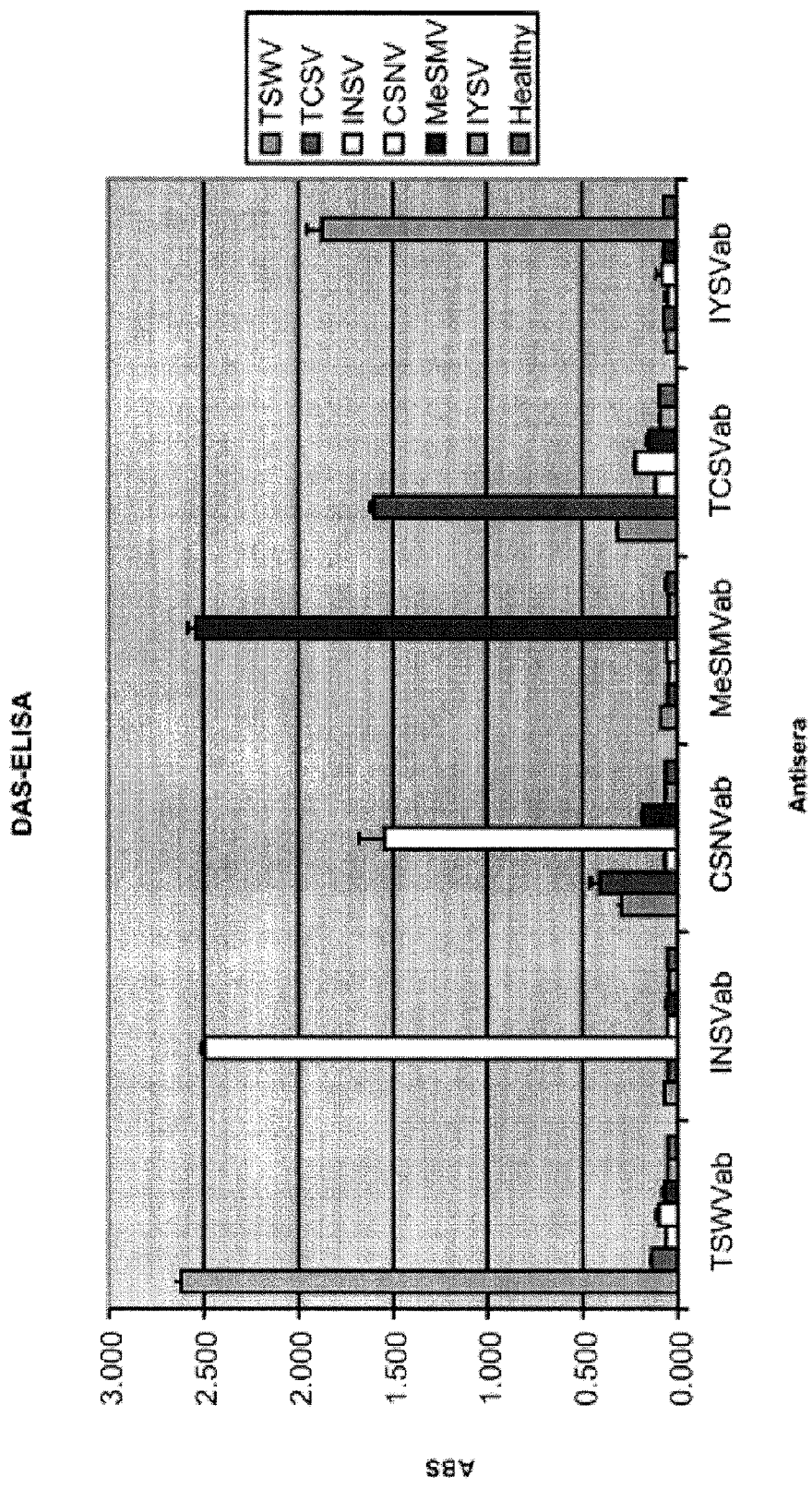
FIG. 3 depicts serological reactions in double-antibody sandwich enzyme-linked immunosorbent assay among six Tospovirus spp. using antisera made against the nucleocapsids of each virus (X axis) and, as antigens, *Nicotiana benthamiana* plants infected with each of the homologous viruses detailed in the legend. Numbers in the Y axis indicate absorbance values at 405 nm. Error bars represent standard deviation calculated from four replicates for each sample. Viruses: Tomato spotted wilt virus (TSWV) BAA03025, Tomato chlorotic spot virus (TCSV) AAG23654, Impatiens necrotic spot virus (INSV) AAA47974, Chrysanthemum stem necrosis virus (CSNV) AAF04197, Melon severe mosaic virus (MeSMV), and Iris yellow spot virus (IYSV) AAF75556.
Figure 4:
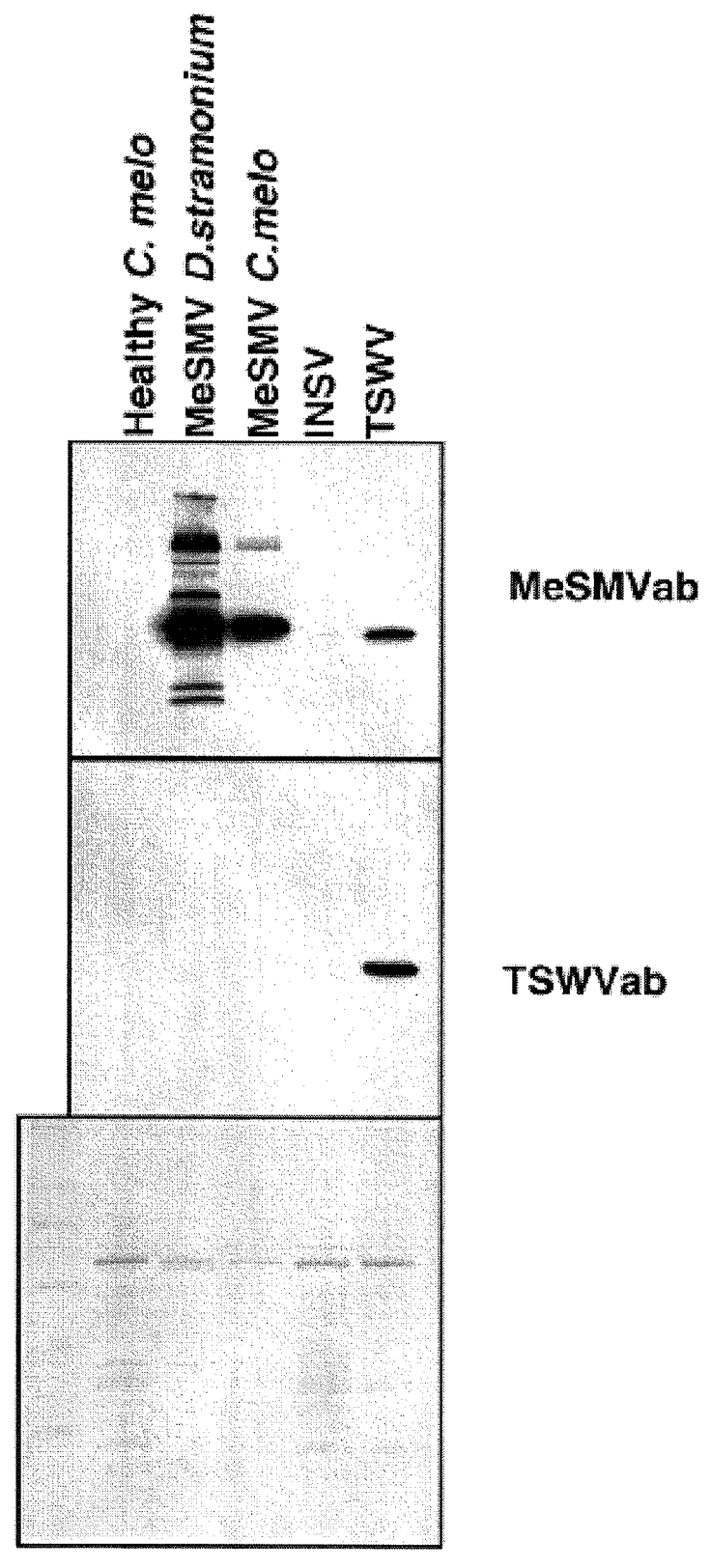

In DAS-ELISA, the MeSMV antibody did not cross-react with other Tospovirus antigens tested, whereas some cross-reactivity was shown for a number of Tospovirus antigens (including a very low value for MeSMV) when anti-CSNV and anti-TCSV antibodies were used (FIG. 3). Western blot analysis using anti-MeSMV antibodies on total soluble proteins extracted from infected leaves confirmed the serological reactions seen in DAS-ELISA. MeSMV antibodies showed a strong reaction with its corresponding infected plant but also a positive reaction with TSWV infected plants (FIG. 4). However, TSWV antibodies (A353) did not show a similar cross-reaction with MeSMV in Western blot (FIG. 4).

Example 4

Sequence Analysis and Virus Phylogenetic and Taxonomic Placement

The MeSMV complete nucleotide sequence of the S RNA was obtained from a number of overlapping clones (SEQ ID NO. 1, National Center for Biotechnology Information (NCBI) accession no. EU275149). The S RNA was 3,283 nucleotides (nt) and contained two open reading frames (ORF). The first ORF, from nucleotide 81 to 1,448 (SEQ ID NO. 2), encoded the NSs protein (SEQ ID NO. 6, 455 aa) with an estimated molecular weight of 50.9 kDa. The second ORF, from nucleotide 2,336 to 3,124 (SEQ ID NO. 3), encoded the N protein (SEQ ID NO. 7, 262 aa) with an estimated molecular weight of 29.5 kDa, which was similar to the N protein molecular weight estimate based on electrophoretic mobility of the purified nucleocapsids.

The noncoding intergenic region (IR) was 888 nt, rich in A and U residues (74%), and predicted to form the typical hairpin secondary structure (not shown). The sequences of a 1-kb fragment of the M RNA (SEQ ID NO. 4) and a 1.5-kb fragment of the L RNA (SEQ ID NO. 5) were also obtained and deposited in GenBank (NCBI accession nos. FJ157984 and FJ157985, respectively).

To clarify the taxonomic position of MeSMV, the N protein and a part of the glycoprotein (G) precursor protein (SEQ ID NO. 8) from amino acid position 430 to 917 when aligned to TSWV G precursor protein, therefore covering part of the Gc region) were compared with corresponding regions of other known Tospovirus spp. For the N protein, the highest similarity was with CSNV (67%; Table 3). For partial G protein, the highest similarity was with TSWV (72%; Table 4).

Figure 5:
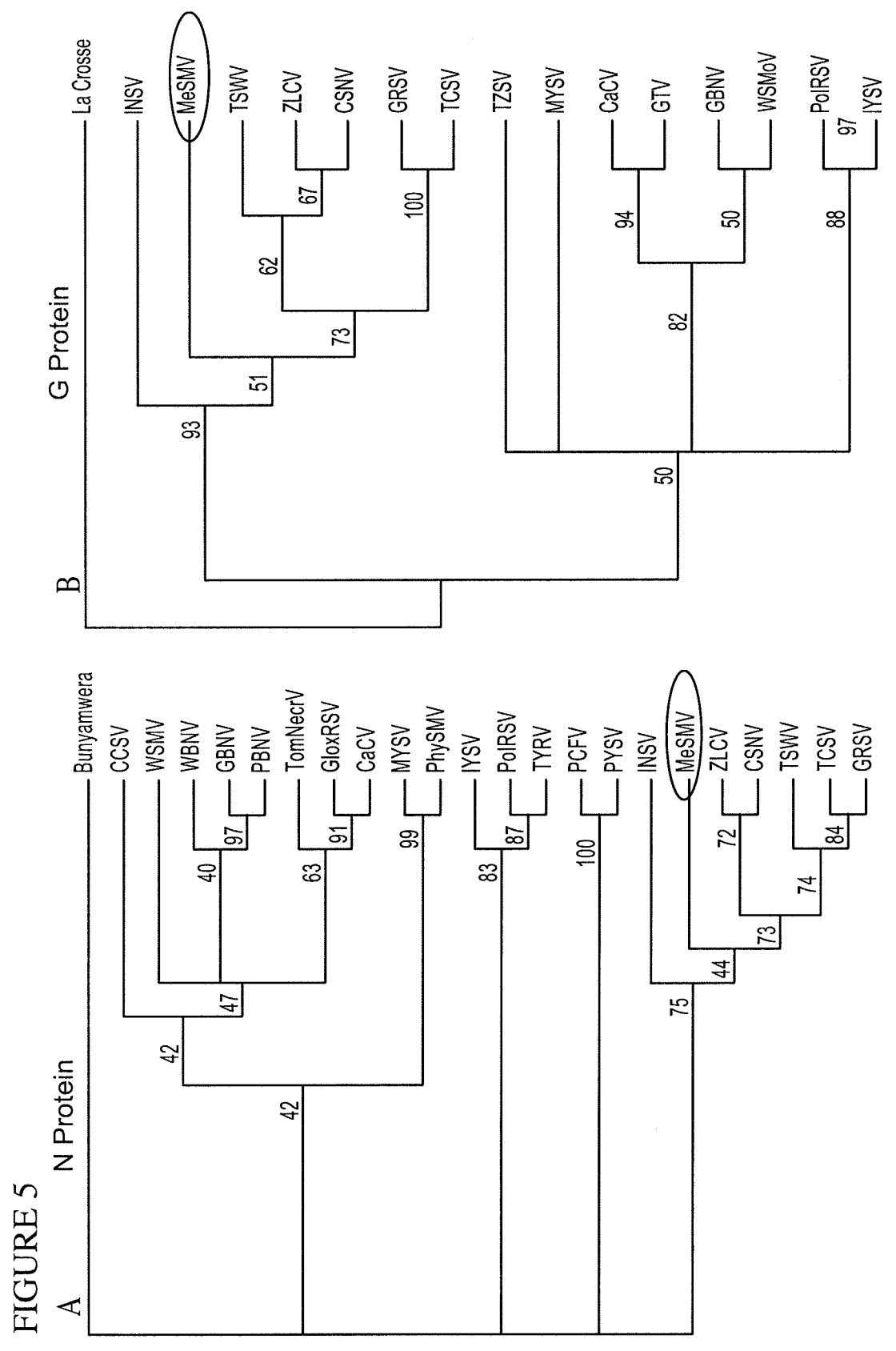

A phylogenetic tree based on Tospovirus N proteins (FIG. 5A) showed the presence of four main clusters: one with viruses distributed mainly in North and South America, assuming that TSWV and Impatiens necrotic spot virus (INSV) are likely of American origin; a second cluster of the tospoviral species from Asia; a third cluster containing Iris yellow spot virus (IYSV), Polygonum ring spot virus (PolRSV), and Tomato yellow ring virus (TYRV), three Tospovirus spp. likely of Middle-Eastern origin (12); and a fourth cluster composed of Peanut yellow spot virus (PYSV) and Peanut chlorotic fanspot virus (PCFV), two viruses with possible origin in south-eastern Asia. MeSMV is in the clade of

TABLE 3

Similarity based on the alignment of the nucleocapsid protein of 22 *Tospovirus* spp.[a]

| Virus | GloxRSV | CaCV | TomNecrV | GBNV | PBNV | WBNV | WSMoV | CCSV | MYSV | PhySMV | PolRSV | TYRV |
|---|---|---|---|---|---|---|---|---|---|---|---|---|
| GloxRSV | 1.000 | 1.000 | 0.974 | 0.888 | 0.887 | 0.841 | 0.886 | 0.707 | 0.629 | 0.635 | 0.488 | 0.528 |
| CaCV | — | 1.000 | 0.974 | 0.888 | 0.887 | 0.841 | 0.886 | 0.709 | 0.633 | 0.638 | 0.493 | 0.533 |
| TomNecrV | — | — | 1.000 | 0.880 | 0.880 | 0.845 | 0.890 | 0.684 | 0.631 | 0.637 | 0.491 | 0.531 |
| GBNV | — | — | — | 1.000 | 0.996 | 0.883 | 0.907 | 0.691 | 0.608 | 0.608 | 0.469 | 0.489 |
| PBNV | — | — | — | — | 1.000 | 0.886 | 0.906 | 0.691 | 0.613 | 0.613 | 0.473 | 0.493 |
| WBNV | — | — | — | — | — | 1.000 | 0.886 | 0.686 | 0.575 | 0.575 | 0.457 | 0.468 |
| WSMoV | — | — | — | — | — | — | 1.000 | 0.703 | 0.610 | 0.615 | 0.475 | 0.500 |
| CCSV | — | — | — | — | — | — | — | 1.000 | 0.630 | 0.630 | 0.486 | 0.530 |
| MYSV | — | — | — | — | — | — | — | — | 1.000 | 0.992 | 0.524 | 0.527 |
| PhySMV | — | — | — | — | — | — | — | — | — | 1.000 | 0.529 | 0.532 |
| PolRSV | — | — | — | — | — | — | — | — | — | — | 1.000 | 0.825 |
| TYRV | — | — | — | — | — | — | — | — | — | — | — | 1.000 |
| IYSV | — | — | — | — | — | — | — | — | — | — | — | — |
| CSNV | — | — | — | — | — | — | — | — | — | — | — | — |
| ZLCV | — | — | — | — | — | — | — | — | — | — | — | — |
| GRSV | — | — | — | — | — | — | — | — | — | — | — | — |
| TCSV | — | — | — | — | — | — | — | — | — | — | — | — |
| TSWV | — | — | — | — | — | — | — | — | — | — | — | — |
| MeSMV | — | — | — | — | — | — | — | — | — | — | — | — |
| INSV | — | — | — | — | — | — | — | — | — | — | — | — |
| PCFV | — | — | — | — | — | — | — | — | — | — | — | — |
| PYSV | — | — | — | — | — | — | — | — | — | — | — | — |

| Virus | IYSV | CSNV | ZLCV | GRSV | TCSV | TSWV | MeSMV | INSV | PCFV | PYSV |
|---|---|---|---|---|---|---|---|---|---|---|
| GloxRSV | 0.509 | 0.270 | 0.277 | 0.283 | 0.282 | 0.294 | 0.288 | 0.313 | 0.274 | 0.238 |
| CaCV | 0.514 | 0.277 | 0.284 | 0.290 | 0.288 | 0.301 | 0.286 | 0.319 | 0.271 | 0.235 |
| TomNecrV | 0.516 | 0.272 | 0.280 | 0.286 | 0.284 | 0.302 | 0.286 | 0.306 | 0.282 | 0.243 |
| GBNV | 0.452 | 0.272 | 0.295 | 0.281 | 0.270 | 0.272 | 0.309 | 0.306 | 0.256 | 0.227 |
| PBNV | 0.457 | 0.275 | 0.298 | 0.284 | 0.272 | 0.275 | 0.312 | 0.299 | 0.259 | 0.227 |
| WBNV | 0.436 | 0.277 | 0.290 | 0.276 | 0.250 | 0.262 | 0.304 | 0.296 | 0.249 | 0.213 |
| WSMoV | 0.459 | 0.273 | 0.305 | 0.296 | 0.256 | 0.259 | 0.311 | 0.306 | 0.247 | 0.246 |
| CCSV | 0.484 | 0.260 | 0.282 | 0.262 | 0.222 | 0.254 | 0.278 | 0.245 | 0.200 | 0.192 |

TABLE 3-continued

Similarity based on the alignment of the nucleocapsid protein of 22 *Tospovirus* spp.[a]

| | | | | | | | | | | |
|---|---|---|---|---|---|---|---|---|---|---|
| MYSV | 0.536 | 0.316 | 0.309 | 0.300 | 0.288 | 0.304 | 0.299 | 0.299 | 0.201 | 0.197 |
| PhySMV | 0.541 | 0.319 | 0.312 | 0.302 | 0.291 | 0.307 | 0.302 | 0.301 | 0.201 | 0.199 |
| PolRSV | 0.709 | 0.377 | 0.385 | 0.382 | 0.371 | 0.348 | 0.343 | 0.311 | 0.240 | 0.261 |
| TYRV | 0.722 | 0.371 | 0.410 | 0.412 | 0.390 | 0.367 | 0.356 | 0.300 | 0.223 | 0.244 |
| IYSV | 1.000 | 0.332 | 0.330 | 0.350 | 0.353 | 0.405 | 0.338 | 0.308 | 0.190 | 0.236 |
| CSNV | — | 1.000 | 0.814 | 0.776 | 0.781 | 0.782 | 0.670 | 0.580 | 0.254 | 0.268 |
| ZLCV | — | — | 1.000 | 0.775 | 0.744 | 0.708 | 0.642 | 0.571 | 0.235 | 0.230 |
| GRSV | — | — | — | 1.000 | 0.863 | 0.761 | 0.636 | 0.587 | 0.253 | 0.257 |
| TCSV | — | — | — | — | 1.000 | 0.785 | 0.638 | 0.564 | 0.235 | 0.260 |
| TSWV | — | — | — | — | — | 1.000 | 0.570 | 0.598 | 0.230 | 0.239 |
| MeSMV | — | — | — | — | — | — | 1.000 | 0.569 | 0.240 | 0.281 |
| INSV | — | — | — | — | — | — | — | 1.000 | 0.232 | 0.244 |
| PCFV | — | — | — | — | — | — | — | — | 1.000 | 0.708 |
| PYSV | — | — | — | — | — | — | — | — | — | 1.000 |

[a]Virus acronyms: *Gloxinia* ringspot virus (GloxRSV) AAQ83791, *Capsicum* chlorosis virus (CaCV) ABC86907, Tomato necrosis virus (TomNecrV) AAT68025, Groundnut bud necrosis virus (GBNV) AAR24021, Peanut bud necrosis virus (PBNV) AAM76063, Watermelon bud necrosis virus (WBNV) ABD39046, Watermelon silver mottle virus (WSMoV) AAW64930, *Calla* lily chlorotic spot (CCSV) AAW58115, Melon yellow severe virus (MYSV) BAB79455, *Physalis* severe mosaic virus (PhySMV) AAD34201, *Polygonum* ringspot virus (PolRSV) EF445397, Tomato yellow ring virus (TYRV) ABF59486, *Iris* yellow spot virus (IYSV) AAF75556, *Chrysanthemum* stem necrosis virus (CSNV) AAF04197, Zucchini lethal chlorosis virus (ZLCV) AAF04198, Groundnut ring spot virus (GRSV) AAF25255, Tomato chlorotic spot virus (TCSV) AAG23654, Tomato spotted wilt virus (TSWV) BAA03025, Melon severe mosaic virus (MeSMV), *Impatiens* necrotic spot virus (INSV) AAA47974, Peanut chlorotic fanspot virus (PCFV) AAC99405, and Peanut yellow spot virus (PYSV) AAB94022. Similarity values were obtained by the software PROTDIST as detailed in the material and methods section. In bold are the values relative to MeSMV nucleocapsid alignment with the other *Tospovirus* spp.

TABLE 4

Similarities between a fragment of the glyco-protein of 15 *Tospovirus* spp.[a]

| Virus | CSNV | TSWV | GRSV | TCSV | ZLCV | INSV | MeSMV | GTV |
|---|---|---|---|---|---|---|---|---|
| CSNV | 1.000 | 0.907 | 0.862 | 0.865 | 0.874 | 0.708 | 0.694 | 0.393 |
| TSWV | | 1.000 | 0.867 | 0.883 | 0.870 | 0.719 | 0.720 | 0.398 |
| GRSV | | | 1.000 | 0.975 | 0.831 | 0.706 | 0.715 | 0.406 |
| TCSV | | | | 1.000 | 0.844 | 0.712 | 0.710 | 0.407 |
| ZLCV | | | | | 1.000 | 0.692 | 0.674 | 0.393 |
| INSV | | | | | | 1.000 | 0.670 | 0.399 |
| MeSMV | | | | | | | 1.000 | 0.402 |
| GTV | | | | | | | | 1.000 |
| CaCV | | | | | | | | |
| GBNV | | | | | | | | |
| WSMoV | | | | | | | | |
| TZSV | | | | | | | | |
| MYSV | | | | | | | | |
| IYSV | | | | | | | | |
| PolRSV | | | | | | | | |

| Virus | CaCV | GBNV | WSMoV | TZSV | MYSV | IYSV | PolRSV |
|---|---|---|---|---|---|---|---|
| CSNV | 0.384 | 0.394 | 0.385 | 0.388 | 0.405 | 0.403 | 0.420 |
| TSWV | 0.395 | 0.401 | 0.414 | 0.402 | 0.419 | 0.412 | 0.424 |
| GRSV | 0.389 | 0.399 | 0.414 | 0.398 | 0.403 | 0.411 | 0.403 |
| TCSV | 0.390 | 0.394 | 0.410 | 0.399 | 0.403 | 0.411 | 0.403 |
| ZLCV | 0.388 | 0.394 | 0.400 | 0.394 | 0.419 | 0.412 | 0.429 |
| INSV | 0.398 | 0.397 | 0.395 | 0.394 | 0.406 | 0.384 | 0.411 |
| MeSMV | 0.399 | 0.399 | 0.402 | 0.395 | 0.397 | 0.417 | 0.411 |
| GTV | 0.929 | 0.918 | 0.903 | 0.770 | 0.726 | 0.741 | 0.746 |
| CaCV | 1.000 | 0.905 | 0.881 | 0.764 | 0.745 | 0.738 | 0.727 |
| GBNV | | 1.000 | 0.930 | 0.791 | 0.738 | 0.759 | 0.733 |
| WSMoV | | | 1.000 | 0.791 | 0.732 | 0.770 | 0.735 |
| TZSV | | | | 1.000 | 0.749 | 0.706 | 0.724 |
| MYSV | | | | | 1.000 | 0.671 | 0.675 |
| IYSV | | | | | | 1.000 | 0.861 |
| PolRSV | | | | | | | 1.000 |

[a]Virus acronyms: *Chrysanthemum* stem necrosis virus (CSNV) AAF04197, Tomato spotted wilt virus (TSWV) BAA03025, Groundnut ring spot virus (GRSV) AAF25255, Tomato chlorotic spot virus (TCSV) AAG23654, Zucchini lethal chlorosis virus (ZLCV) AAF04198, *Impatiens* necrotic spot virus (INSV) AAA47974, Melon severe mosaic virus (MeSMV), *Gloxinia tospovirus* (GTV) (AAC15466.1), *Capsicum* chlorosis virus (CaCV) ABC86907, Groundnut bud necrosis virus (GBNV) AAR24021, Watermelon silver mottle virus (WSMoV) AAW64930, Tomato zonate spot virus (TZSV), Melon yellow severe virus (MYSV) BAB79455, *Iris* yellow spot virus (IYSV) AAF75556, and *Polygonum* ringspot virus (PolRSV) EF445397. Similarity values were obtained by the software PROTDIST American species but in a separate branch. The consensus tree relative to G protein alignments (FIG. 5B) showed that MeSMV clusters with "new world" Tospovirus spp.

Example 5

Survey of Mexican Cucurbits Crops

Following the initial identification of MeSMV as a new Tospovirus sp., a survey to assess its incidence and distribution in several melon-growing areas of Mexico was undertaken. Of the 147 symptomatic plants that were tested, MeSMV was found in melon, zucchini, cucumber, and watermelon plants (Table 5). The results from LF were confirmed when validated by both DAS-ELISA (carried out on 10 samples) and RT-PCR (carried out on 30 samples). Given the surprising results for the field infected cucumber sample, we checked whether significant molecular differences were present in the cucumber isolate when compared with the melon isolate we had cloned and sequenced; the RT-PCR product obtained from the same sample was sequenced directly, confirming 99% identity with the MeSMV sequence deposited in GenBank (not shown). In summary, the majority of the 147 plants (66%) from various states in Mexico were MeSMV positive by LF, indicating its relatively wide geographic distribution and presence in different cucurbit crops (Table 5).

reasons, including different cultivars, mechanical versus thrips transmission, or biological diversity of the virus isolates from different hosts, even though no evidence of such occurrence was shown for other Tospovirus spp. (33). Nevertheless, MeSMV has a broad host range among cucurbits and could represent a new virus problem in the Americas. The N protein amino acid sequence is an important criterion to classify Tospovirus spp. (7,9,15,21). Less than 80% similarity is considered the limit to separate different species (15). Analysis of the S RNA genomic segment showed that maximum similarity between the MeSMV N protein amino acid sequence and those of other Tospovirus spp. is 67% with CSNV, well below the threshold and, thus, supporting the idea that MeSMV is a distinct Tospovirus spp.

Like the host range and sequence analyses, serological analysis for Tospovirus N proteins showed that MeSMV is a distinct Tospovirus sp. The Western blot analysis showed that MeSMV antibodies cross reacted with TSWV N proteins but only when tested under these denaturing conditions. This warns against using this technique for open-field diagnostic purposes. By contrast, the specificity of the MeSMV antibodies in DAS-ELISA well suits the requirements for a sensitive and specific diagnostic kit to process a large number of field samples.

TABLE 5

Survey of Mexican cucurbit crops

| Locations in Mexico | Number of MeSMV-positive samples over the number tested [a] | | | |
|---|---|---|---|---|
| | Watermelon | Melon | Cucumber | Zucchini |
| Puebla | — | — | — | 28/35 (18 by Lateral Flow; 10 by RT-PCR) |
| Guerrero, Michoacan de Ocampo | — | 43/55 (32 by Lateral Flow; 11 by RT-PCR) | — | — |
| Campeche, Chiapas and Jalisco | 15/30 (5 by Lateral Flow; 10 by RT-PCR) | — | — | — |
| Sinaloa | — | — | 1/2 (1 by RT-PCR) | — |
| Mexico | — | — | — | 13/25 (9 by Lateral Flow; 4 by RT-PCR) |

[a] Samples were analyzed by later flow devices in the field, and a subset was confirmed to be infected by Melon severe mosaic virus (MeSMV) by reverse-transcription polymerase chain reaction and double-antibody sandwich enzyme-linked immunosorbent assay.

Discussion

Cantaloupe is one of the most economically important cucurbit crops in Mexico. PRSV, WMV, ZYMV, and CMV are the major viruses reported in Mexican cucurbit crops (8). Squash leaf curl virus is also prevalent in some parts of Mexico (3,5,22) and, recently, Cucurbit yellowstunting disorder virus has been reported (4).

In recent years, a new disease has been spreading in cucurbits crops, especially on melon and watermelon, sometimes reducing production by as much as 20 to 30%. Applicants' study showed that a new Tospovirus spp. is associated with this new disease. Specificity of the host range and serological and N-protein relationship indicate that MeSMV is a new Tospovirus sp. It was somewhat surprising to confirm MeSMV infection of zucchini and cucumber in the open fields, because plants of these species did not get infected in the host range experiments. This could be due to several The vector for MeSMV is not yet known, although western flower thrips (*Frankliniella occidentalis*), a known Tospovirus vector species, was present on MeSMV-infected plants. CSNV is transmitted by *F. occidentalis* and *F. schultzei* (1), whereas ZLCV (another cucurbitinfecting Tospovirus sp. from the Americas) is transmitted only by *F. zucchini* (17). It is unknown exactly how long MeSMV has been present in Mexico because symptoms are not always specific, and the presence of the most common cucurbit Potyvirus spp. (e.g., ZYMV) could have masked the presence of MeSMV. The widespread presence of MeSMV on different cucurbit crops and in different states of Mexico also suggests that MeSMV has already been established and, given the contiguous nature of cucurbit cultivation between Mexico and the southern states of the United States, a close inspection of cucurbit crops in the southern United States to determine the presence of MeSMV should be undertaken.

Example 6

Breeding of *Cucurbita Pepo* Varieties Resistant to MeSMV

In preliminary trials in Mexico with natural infection of MeSMV, the inventors had a number of varieties of *Cucurbita pepo*, as well as several varieties of *Cucurbita moschata*. The results were that all the *C. pepo* varieties were susceptible, whereas all the *C. moschata* varieties were resistant, as shown in Table 6 (Aratichangio, MX) and Table 7 (Capeo, MX).

Specifically, HMX 7732 (*C. moschata*), WSXP 1030 (Native Squash, *C. moschata*), SSXP 3793 (Nigerian, *C. moschata*), WSXP 1035 (Menina, *C. moschata*), WSXP 1036 (Ws, *C. moschata*), WSXP 1037 (Sk, *C. moschata*) and SSXP 4513 (*C. maxima*) are resistant to MeSMV, and all tested *C. pepo* varieties are susceptible to MeSMV. Based on the results of these studies, we concluded that *C. moschata* is a good source of resistance for breeding and it was, therefore, chosen as a donor of resistance to MeSMV-caused viral diseases.

TABLE 6

Field trial in Aratichangio, MX, Squash varieties with natural infection of MeSMV

| Variety/ Exp./PI line | # Plants | Res | Int. | Sus | MeSMV Rxn | Comments | | Species |
|---|---|---|---|---|---|---|---|---|
| HMX 7732[1] | 7 | 7 | 0 | 0 | Neg (2) | Resistant | | *C. moschata* |
| WSXP 1030 | 6 | 6 | 0 | 0 | Neg | Resistant | Native Squash | *C. moschata* |
| SSXP 3793 | 5 | 5 | 0 | 0 | | Resistant | Nigerian | *C. moschata* |
| WSXP 1035 | 7 | 7 | 0 | 0 | NEG | Resistant; Leaves curled under Neg SLCV and MeSMV; A 2nd virus may present | Menina | *C. moschata* |
| WSXP 1036 | 8 | 8 | 0 | 0 | NEG | Resistant; Leaves curled under Neg SLCV and MeSMV; A 2nd virus may present | Ws | *C. moschata* |
| WSXP 1037 | 3 | 3 | 0 | 0 | Neg | Resistant | Sk | *C. moschata* |
| WSXP 1038 | 8 | 0 | 0 | 8 | Pos (2) | A few fruit but clean | 312167 | *C. argyrosperma* |
| WXSP 1039 | 7 | 0 | 0 | 7 | Pos | no fruit | Ce | *C. ecuadorensis* |
| Zucchini Elite | 7 | 0 | 0 | 7 | Pos (2) | foliage and fruit symptoms | | *C. pepo* |
| Hurakon | 8 | 0 | 0 | 8 | | Z.E. symptoms more severe then Hurakon | | *C. pepo* |
| Linda | 8 | 3 | 1 | 4 | Pos | | | *C. pepo* |
| Citlali | 8 | 4 | 0 | 4 | | 10% fruit effected | | *C. pepo* |
| SSXP 4511 | 7 | 0 | 0 | 7 | | | NY247 | *C. pepo* |
| Golden Arrow | 8 | 0 | 0 | 8 | Pos | highly susceptible | | *C. pepo* |
| SSXP 4506 | 8 | 0 | 0 | 8 | | | ZYBWO3 | *C. pepo* |
| Zucchini Elite | 8 | 2 | 0 | 6 | Pos (2) | fruit expressing symptoms | | *C. pepo* |
| Huaso | 7 | 1 | 1 | 5 | | | | *C. pepo* |
| SSXP 4507 | 7 | 0 | 0 | 7 | | shortened internodes; | ZYZap | *C. pepo* |
| Arte | 6 | 0 | 0 | 6 | | very few fruit | | *C. pepo* |
| SSXP 4512 | 6 | 0 | 0 | 6 | | fruit looked alright; infection late as old leaves clean and new leaves severe | ZYJ1D | *C. pepo* |
| Redondo de Trunco | 6 | 0 | 1 | 5 | Pos | | | *C. maxima* |
| SSXP 4513 | 4 | 4 | 0 | 0 | Pos | Resistant; fruit exhibited white spots and tested positive in fruit | ZYCM1 | *C. maxima* |

This trial was done in Aratichangio, MX

[1]HMX 7732 is a commercially available variety named "Butterfly".

TABLE 7

Field trial in Capeo, MX, Squash varieties with natural infection of MeSMV

| Variety/Exp./PI line | # Plants | Res | Int. | Sus | MeSMV Rxn | Comments | | Species |
|---|---|---|---|---|---|---|---|---|
| HMX 7732 | 6 | 6 | 0 | 0 | | Resistant | | C. moschata |
| WSXP 1030 | 8 | 0 | 0 | 0 | | Resistant | Native Squash | C. moschata |
| SSXP 3793 | 4 | 0 | 0 | 0 | | Resistant | Nigerian | C. moschata |
| WSXP 1035 | 10 | 0 | 0 | 0 | NEG | Resistant | Menina | C. moschata |
| WSXP 1036 | 10 | 0 | 0 | 0 | NEG | Resistant | $Ws^2$ | C. moschata |
| WSXP 1037 | 2 | 0 | 0 | 0 | | Resistant | $Sk^3$ | C. moschata |
| WSXP 1038 | 6 | 6 | 0 | 0 | | NO Virus present | 312167 | C. argyrosperma |
| WXSP 1039 | 9 | 9 | 0 | 0 | | NO Virus present | Ce | C. ecuadorensis |
| Zucchini Elite | 10 | 0 | 0 | 10 | Pos | | | C. pepo |
| Hurakon | 10 | 1 | 0 | 9 | Pos | | | C. pepo |
| Linda | 10 | 1 | 0 | 9 | | | | C. pepo |
| Citlali | 10 | 1 | 0 | 9 | | | | C. pepo |
| SSXP 4511 | 10 | 2 | 0 | 8 | | | NY247 | C. pepo |
| Golden Arrow | 10 | 4 | 0 | 6 | | | | C. pepo |
| SSXP 4506 | 10 | 0 | 0 | 10 | | | ZYBWO3 | C. pepo |
| Zucchini Elite | 7 | 0 | 0 | 7 | | | | C. pepo |
| Huaso | 4 | 0 | 0 | 4 | | | | C. pepo |
| SSXP 4507 | 8 | 1 | 5 | 2 | | Moderate infection (possibly later infection) | ZYZap | C. pepo |
| Arte | 7 | 2 | 0 | 5 | | | | C. pepo |
| SSXP 4512 | 6 | 0 | 1 | 5 | | | ZYJ1D | C. pepo |
| Redondo de Trunco | 5 | 5 | 0 | 0 | | | | C. maxima |
| SSXP 4513 | 1 | 1 | 0 | 0 | | Resistant | ZYCM1 | C. maxima |

This trial was done in Capeo, MX
[2]Mexucan "land race"
[3]Shimer Kobocha

Several germplasms are being created in order to develop a molecular marker map and develop resistance to viruses, which can be used in the process of transferring MeSMV resistance from C. moschata to C. pepo.

Mapping germplasms will be created with the goal of collecting approx. 100 C. pepo lines that are identical expect for having different small pieces of C. moschata chromosome embedded in their genomes, by backcrossing. The total of all the small pieces would encompass the total genome of C. moschata. These lines will form an introgression line library which would be the ideal material for transferring resistance. These 100 lines are to be inoculated with the isolated MeSMV strain to select certain line(s) that is/are resistant to the virus infection. These resistant line(s) can then used to backcross resistance into other susceptible wild type C. pepo lines. In addition, some backcross F3 and F4 lines derived from the first backcross of the ILL creation will be created and can be used in the same way. These would be 75% C. pepo.

In addition, congruity interspecific hybrids between C. moschata and C. pepo are being created by alternating backcrosses each generation between the two species. Several varieties of C. moschata will be used to generate these congruity interspecific backcrosses. Germplasm materials, such as hybrid lines of ⅔ C. pepo, ⅓ C. moschata, or hybrid lines of ⅓ C. pepo, ⅔ C. moschata are being generated, which can be also tested and used as the starting point of resistance breeding.

After identification of the starting line that is resistant to the isolated MeSMV strain, such line can be used as the resistance donor for backcrossing to a preferred C. pepo variety which is susceptible to the isolated MeSMV strain. Hurakan grey zucchini, a type commonly grown all over Mexico, as well as Prestige dark zucchini lines, a type that is grown primarily in western Mexico for export to the US, are chosen as the recipient lines. Segregating populations from the backcrosses are to be inoculated with the isolated MeSMV strain, and resistant plants are selected for further backcrossing.

Under the situation when the resistance is due to dominant or partially dominant locus/loci, backcrossing can be done without interruption. Plants can be selected on the basis of rated visual symptoms first, and the use of MeSMV immunostrips and RT-PCR asymptomatic plants will be checked to verify their resistance level. A few susceptible plants will also be checked to validate presence of MeSMV.

Under the situation when the resistance is due to recessive locus/loci, self pollinations between backcross generations can be applied. An ILL is a good starting line in this situation, if a molecular marker associated with the resistance can be identified. This would eliminate the need to inoculate with virus each generation and would enable continuous backcrossing.

After several rounds of backcrossing (e.g., 1, 2, 3, 4, 5, 6 or more rounds of backcrosses), a MeSMV resistant Hurakan grey zucchini hybrid variety and a MeSMV resistant Prestige dark zucchini hybrid variety can be created.

Example 7

Breeding of Squash Varieties Resistant to MeSMV

Figure 7:
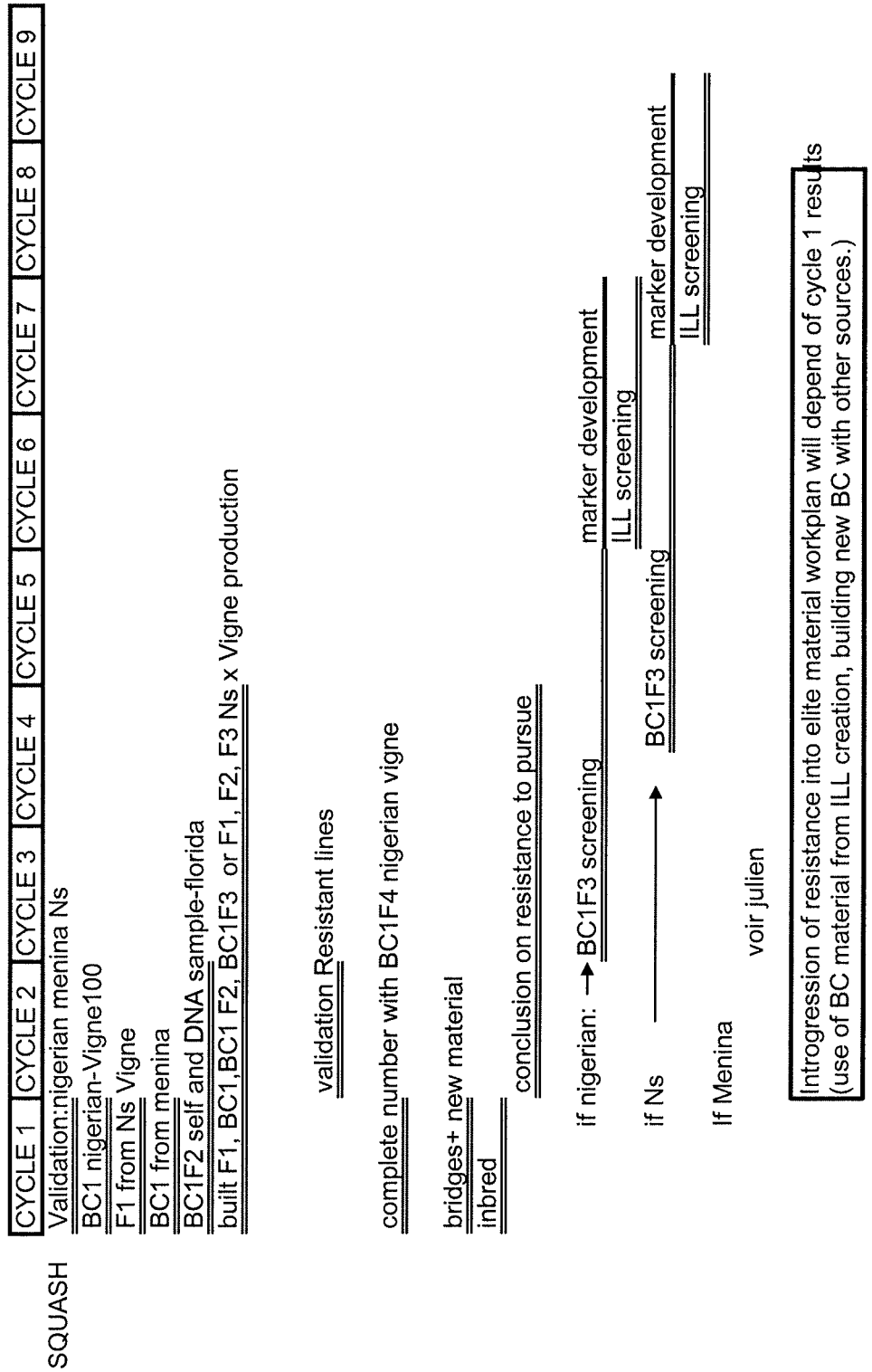
FIG. 7 depicts breeding scheme of creating improved elite squash line resistant to MeSMV.

Three squash varieties, Menina Rajada Seca (C. moschata), Native squash (Ns, C. moschata), and Nigerian (*C. moschata*) were tested for resistance to MeSMV (see Table 6 and Table 7). Each line is MeSMV resistant. Any of these three varieties, or any other MeSMV resistant varieties listed in Table 6 and Table 7, can be used for breeding of squash varieties that are resistant to MeSMV. A breeding strategy illustrated in FIG. 7 can be carried out to introgressed MeSMV resistance segment into an elite recipient line.

Initially, a cross between the donor line (MeSMV resistant squash species selected from the group consisting of Menina, Ns and Nigerian) is crossed with a recipient line (an elite commercial line that is susceptible to MeSMV, e.g., Vigne squash variety) to generate F1. The F1 is then self-pollinated to create F2 population, or backcrossed with the elite line to create at least 100 BC1 lines, which are then used to determine the resistance inheritance. Either F1, F2 or the BC1 can be inoculated with isolated MeSMV strain and screened. The behavior of these three populations give a strong initial indication of whether the resistance is dominant or recessive and whether one or more genes are involved in controlling the resistance. Four possible inheritance categories are, monogenic dominant, multigenic dominant, monogenic recessive and multigenic recessive. The determination of inheritance would influence the approach for resistance introgression into elite lines.

Concurrently, F1, F2 (or BC1F2), F3 (or BC1F3), and F4 (or BC1F3) families (ILLs) can be developed for screening. These families also serve as populations for molecular marker discovery in BSA (Bulk Segregant Analysis). For example, at least 100 F3 (or BC1F3) families of a MeSMV resistant donor line selected from Nigerian, Ns or the Menina can be screened against MeSMV, and data is collected and F2 progenitor DNA is analyzed to identify common marker patterns that correlate well with the F3 family virus indexing data. These well validated markers are of great benefit in the eventual rapid introgression of the resistance into elite lines. Meanwhile, marker assistant backcross of F3 with the elite recipient line can be carried out with the help of molecular marker identified, in order to screen for resistant individual IL that has most of genome from the elite line, with only the MeSMV segment from the donor line, from the ILL. Self cross between each backcross may be needed. As a result, an elite squash line introgressed with MeSMV resistant segment can be produced.

Example 8

Breeding of Melon Varieties Resistant to MeSMV

In preliminary trials, all of the putative identified melon varieties resistant to MeSMV come from the lines listed in Table 8 (Aratichangio, MX) and Table 9 (Capeo, MX). Details of melon accessions used in the field trails are shown in Table 10. All of these lines are characterized by small yellow fruit types, bitter white flesh and late maturity. They are phenotypically somewhat similar to a source well known to be resistant to CYSDV (cucurbit yellows stunting disorder virus). Specifically, varieties PI 482393, PI 482394, PI 482395, PI 482398, PI 482403, PI 482409, PI 482411, PI 482414, PI 482417, PI 482419, PI 482431, PI 505600, PI 505602, and PI 505603 were resistant to MeSMV in at least one field trial. Any of these can be used for breeding of melon varieties that are resistant to MeSMV.

TABLE 8

Field trial in Aratichangio, MX, Melon varieties with natural infection of MeSMV

| Variety/ Exp./PI line | # Plants | Res | Int | Sus | MeSMV Rxn. | Comments |
|---|---|---|---|---|---|---|
| PI 482393 | 11 | 11 | 0 | 0 | | Resistant HDGF 3 plts 100% infected next to plot |
| PI 482394 | 11 | 11 | 0 | 0 | | Resistant |
| PI 482395 | 11 | 11 | 0 | 0 | | Resistant |
| PI 482396 | 11 | 3 | 0 | 8 | POS (2) | |
| PI 482397 | 12 | 0 | 0 | 12 | POS (2) | Extremely susceptible MeSMV |
| PI 482398 | 11 | 10 | 1 | 0 | NEG | resistant |
| PI 482399 | 9 | 0 | 0 | 9 | | |
| PI 482400 | NO SEED | | | | | |
| PI 482401 | 11 | 0 | 0 | 11 | POS (2) | |
| PI 482402 | 8 | 8 | 0 | 0 | | |
| PI 482403 | 10 | 10 | 0 | 0 | | Resistant |
| PI 482406 | Plants Died | | | | | |
| PI 482407 | 3 | 1 | 0 | 2 | | 4 plants had died |
| PI 482408 | 11 | 9 | 0 | 2 | | |
| PI 482409 | 10 | 10 | 0 | 0 | | Resistant |
| PI 482410 | 12 | 5 | 0 | 7 | POS | |
| PI 482411 | 11 | 11 | 0 | 0 | | Resistant |
| PI 482414 | 10 | 10 | 0 | 0 | | Resistant |
| PI 482417 | 8 | 8 | 0 | 0 | | Resistant |
| PI 482419 | 2 | 2 | 0 | 0 | | Resistant |
| PI 482421 | 9 | 6 | 0 | 3 | | |
| PI 482422 | 7 | 3 | 0 | 4 | | |
| PI 482424 | 6 | 0 | 0 | 6 | | |
| PI 482427 | Plants Died | | | | | |
| PI 482429 | Plants Died | | | | | |
| PI 482430 | NO SEED | | | | | |
| PI 482431 | 11 | 0 | 0 | 11 | | |
| PI 482 433 | Plants Died | | | | | |
| PI 482434 | 3 | 0 | 0 | 3 | | |
| PI 500362 | 2 | 0 | 0 | 2 | | |
| PI 505599 | 5 | 0 | 0 | 5 | | |
| PI 505600 | 8 | 8 | 0 | 0 | NEG | Resistant |
| PI 505601 | 8 | 5 | 0 | 3 | POS | |
| PI 505602 | 7 | 7 | 0 | 0 | | Resistant |
| PI 505603 | 6 | 6 | 0 | 0 | | Resistant |
| Co (lot: 05-2713) | 8 | 6 | 0 | 2 | | |
| TGR 1551 (lot: 05-2133) | 7 | 4 | 0 | 3 | | |
| P41 (lot: 04-1017) | 8 | 2 | 0 | 6 | | |

This trial was done in Aratichangio, MX

TABLE 9

Field trial in Capeo, MX, Melon varieties with natural infection of MeSMV

| Variety/ Exp./PI line | # Plants | Res | Int | Sus | MeSMV Rxn. | Comments |
|---|---|---|---|---|---|---|
| PI 482393 | 11 | 11 | 0 | 0 | | Resistant |
| PI 482394 | 11 | 11 | 0 | 0 | | Resistant |
| PI 482395 | 11 | 11 | 0 | 0 | | Resistant |
| PI 482396 | 9 | 6 | 0 | 3 | | |
| PI 482397 | 8 | 4 | 2 | 2 | | |
| PI 482398 | 9 | 9 | 0 | 0 | | Resistant |
| PI 482399 | 9 | 3 | 2 | 4 | | |

TABLE 9-continued

Field trial in Capeo, MX, Melon varieties with natural infection of MeSMV

| Variety/Exp./PI line | # Plants | Res | Int | Sus | MeSMV Rxn. | Comments |
|---|---|---|---|---|---|---|
| PI 482400 | NO SEED | | | | | |
| PI 482401 | 11 | 4 | 0 | 7 | | |
| PI 482402 | 10 | 9 | 0 | 1 | | |
| PI 482403 | 3 | 3 | 0 | 0 | | Resistant |
| PI 482406 | Plants Died | | | | | |
| PI 482407 | 8 | 4 | 0 | 4 | | |
| PI 482408 | 9 | 7 | 0 | 2 | | |
| PI 482409 | 6 | 2 | 0 | 4 | | |
| PI 482410 | 7 | 2 | 0 | 5 | | |
| PI 482411 | 10 | 8 | 0 | 2 | | |
| PI 482414 | 12 | 6 | 0 | 6 | | |
| PI 482417 | 8 | 8 | 0 | 0 | | Resistant |
| PI 482419 | 2 | 1 | 0 | 1 | | |
| PI 482421 | 10 | 8 | 0 | 2 | | |
| PI 482422 | 10 | 5 | 0 | 5 | | |
| PI 482424 | 10 | 2 | 0 | 8 | | |
| PI 482427 | 5 | 1 | 0 | 4 | | |
| PI 482429 | 9 | 3 | 0 | 6 | | |
| PI 482430 | NO SEED | | | | | |
| PI 482431 | 11 | 10 | 0 | 0 | | Resistant |
| PI 482 433 | Plants Died | | | | | |
| PI 482434 | 10 | 0 | 0 | 10 | | |
| PI 500362 | 8 | 0 | 0 | 8 | | |
| PI 505599 | 8 | 0 | 0 | 8 | | |
| PI 505600 | 10 | 10 | 0 | 0 | | Resistant |
| PI 505601 | 6 | 2 | 0 | 4 | | |
| PI 505602 | 11 | 11 | 0 | 0 | | Resistant |
| PI 505603 | 11 | 11 | 0 | 0 | | Resistant |
| Co (lot: 05-2713) | 10 | 7 | 0 | 3 | | |
| TGR 1551 (lot: 05-2133) | 9 | 3 | 0 | 6 | | |
| P41 (lot: 04-1017) | 10 | 3 | 0 | 7 | | |

This trial was done in Capeo, MX

TABLE 10

Melon Accessions for the MeSMV work in Mexico

| Plot # | IVP | IVNO | IVS | IVT | ITEM | TAXON | QUANT |
|---|---|---|---|---|---|---|---|
| 1 | PI | 482393 | 87ncsi01 | SD | TGR 96 | Cucumis melo subsp. melo | 50 |
| 2 | PI | 482394 | 00ncai01 | SD | Mudyiwa | Cucumis melo subsp. melo | 50 |
| 3 | PI | 482395 | 94ncai01 | SD | Chikakaumbe | Cucumis melo subsp. melo | 50 |
| 4 | PI | 482396 | 87ncsi01 | SD | TGR 141 | Cucumis melo subsp. melo | 50 |
| 5 | PI | 482397 | 87ncsi01 | SD | TGR 150 | Cucumis melo subsp. melo | 50 |
| 6 | PI | 482398 | 87ncsi01 | SD | TGR 185 | Cucumis melo subsp. melo | 50 |
| 7 | PI | 482399 | 92ncab01 | SD | TGR 228 | Cucumis melo subsp. melo | 50 |
| 8 | PI | 482400 | 89ncai01 | SD | TGR 234 | Cucumis melo subsp. melo | 0 |
| 9 | PI | 482401 | 89ncai01 | SD | TGR 240 | Cucumis melo subsp. melo | 50 |
| 10 | PI | 482402 | 87ncsi51 | SD | TGR 241 | Cucumis melo subsp. melo | 50 |
| 11 | PI | 482403 | 87ncsi01 | SD | TGR 271 | Cucumis melo subsp. melo | 50 |
| 12 | PI | 482406 | 99ncai01 | SD | TGR 335 | Cucumis melo subsp. melo | 50 |
| 13 | PI | 482407 | 89ncai01 | SD | TGR 336 | Cucumis melo subsp. melo | 50 |
| 14 | PI | 482408 | 87ncsi01 | SD | TGR 337 | Cucumis melo subsp. melo | 50 |
| 15 | PI | 482409 | 99ncai01 | SD | TGR 338 | Cucumis melo subsp. melo | 50 |
| 16 | PI | 482410 | 87ncsi51 | SD | TGR 365 | Cucumis melo subsp. melo | 50 |
| 17 | PI | 482411 | 90ncai01 | SD | TGR 554 | Cucumis melo subsp. melo | 50 |
| 18 | PI | 482414 | 87ncsi01 | SD | TGR 1250 | Cucumis melo subsp. melo | 50 |
| 19 | PI | 482417 | 99ncai01 | SD | TGR 1420 | Cucumis melo subsp. melo | 50 |
| 20 | PI | 482419 | 99ncai01 | SD | TGR 1534 | Cucumis melo subsp. melo | 50 |
| 21 | PI | 482421 | 87ncsi01 | SD | TGR 1681 | Cucumis melo subsp. melo | 50 |
| 22 | PI | 482422 | 87ncsi51 | SD | TGR 1687 | Cucumis melo subsp. melo | 50 |

TABLE 10-continued

Melon Accessions for the MeSMV work in Mexico

| Plot # | IVP | IVNO | IVS | IVT | ITEM | TAXON | QUANT |
|---|---|---|---|---|---|---|---|
| 23 | PI | 482424 | 92ncab01 | SD | TGR 1709 | Cucumis melo subsp. melo | 50 |
| 24 | PI | 482427 | 87ncsi01 | SD | TGR 1766 | Cucumis melo subsp. melo | 50 |
| 25 | PI | 482429 | 89ncai01 | SD | TGR 1843 | Cucumis melo subsp. melo | 50 |
| 26 | PI | 482430 | 89ncai01 | SD | TGR 1920 | Cucumis melo subsp. melo | 0 |
| 27 | PI | 482431 | 89ncai01 | SD | TGR 1937 | Cucumis melo subsp. melo | 50 |
| 28 | PI | 482433 | 89ncai01 | SD | TGR 2018 | Cucumis melo subsp. melo | 50 |
| 29 | PI | 482434 | 06ncai01 | SD | TGR 2047 | Cucumis melo subsp. melo | 50 |
| 30 | PI | 500362 | 87ncai01 | SD | ZM 1345 | Cucumis melo subsp. melo | 50 |
| 31 | PI | 505599 | 90ncab01 | SD | ZM/A 5317 | Cucumis melo subsp. melo | 50 |
| 32 | PI | 505600 | 90ncab01 | SD | ZM/A 5364 | Cucumis melo subsp. melo | 50 |
| 33 | PI | 505601 | 90ncab01 | SD | ZM/A 5370 | Cucumis melo subsp. melo | 50 |
| 34 | PI | 505602 | 88ncai01 | SD | ZM/A 5384 | Cucumis melo subsp. melo | 50 |
| 35 | PI | 505603 | 91ncai01 | SD | ZM/A 5390 | Cucumis melo subsp. melo | 50 |
| 36 | BC | HM | Co | | lot: 01-6095 | PRSV resistant source | 50 |
| 37 | BC | HM | TGR 1551 | | lot: 05-2133 | WMV resistant source | 50 |
| 38 | BC | HM | P41 | | lot: 04-1017 | ZYMV resistant source | 50 |

Figure 8A:
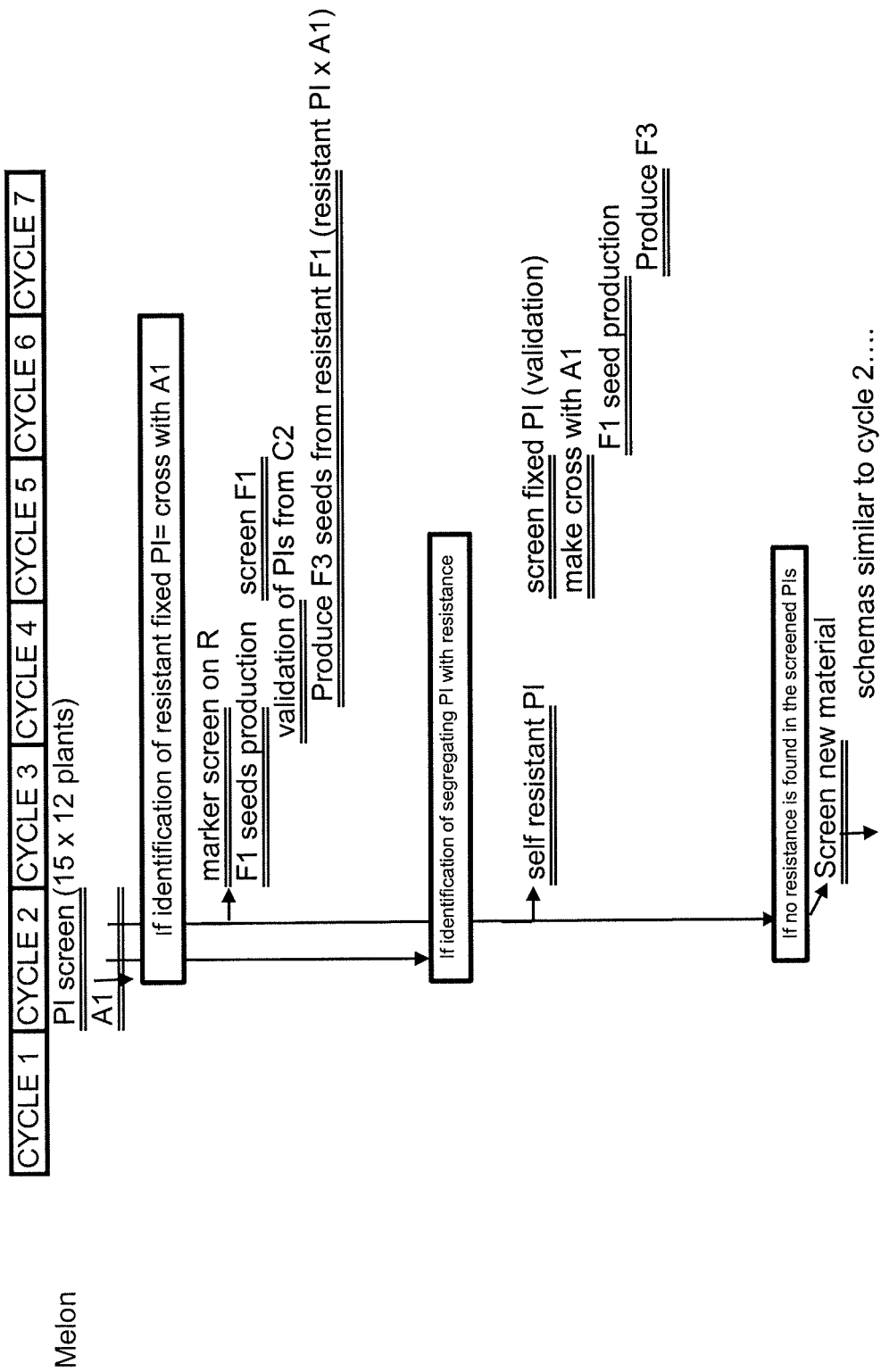
FIG. 8 depicts breeding scheme of creating improved elite melon line resistant to MeSMV. Stage of breeding cycles 1-7 is shown in FIG. 8a, and stage of breeding cycles 8 to 17+ is shown in FIG. 8b. PI is a donor variety resistant to MeSMV, and A1 is an elite recipient line susceptible to MeSMV.
Figure 8B:
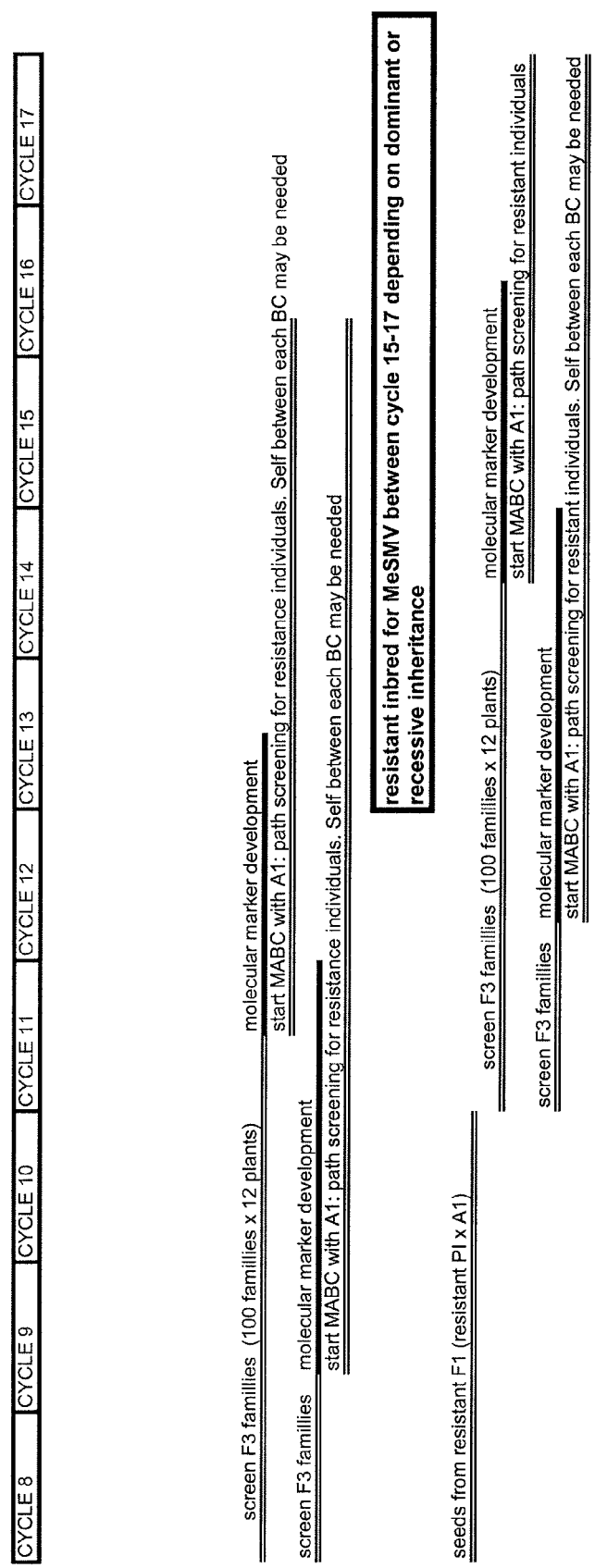

Another melon variety resistant to MeSMV is known as TGR 1551. A breeding strategy illustrated in FIG. 8 can be carried out to introgressed MeSMV resistance segment into an elite recipient line, wherein PI is a candidate MeSMV resistant donor line, and A1 is an elite recipient line.

Initially, a cross between the donor line (MeSMV resistant melon species, e.g., those listed in Table 8 and Table 9, or TGR 1551) can be crossed with a recipient line (e.g., an elite commercial line that is susceptible to MeSMV) to generate F1. The F1 can then self-pollinated to create F2 population, or backcrossed with the elite line to create at least 100 BC1 lines, which can then used to determine the resistance inheritance. Either F1, F2 or the BC1 can be inoculated with isolated MeSMV strain and screened. The behavior of these three populations will give a strong initial indication of whether the resistance is dominant or recessive and whether one or more genes are involved in controlling the resistance. Four possible inheritance categories are, monogenic dominant, multigenic dominant, monogenic recessive and multigenic recessive. The determination of inheritance would influence the approach for resistance introgression into elite lines.

Concurrently, F1, F2 (or BC1F2), F3 (or BC1F3), and F4 (or BC1F3) families (ILLs) can be developed for screening. These families also serve as populations for molecular marker discovery thought Bulk Segregant Analysis, and data can be collected and F2 progenitor DNA can be analyzed to identify common marker patterns that correlate well with the F3 family virus indexing data. These well validated markers can be used in rapid introgression of the resistance into elite lines. Meanwhile, marker assistant backcross of F3 with the elite recipient line can be carried out with the help of molecular marker identified, in order to screen for resistant individuals that has most of genome from the elite line, with only the MeSMV segment from the donor line. Self cross between each backcross may be needed. As a result, an individual introgressed elite melon line resistant to MeSMV is isolated.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Bezerra, I. C., Resende, R., Pozzer, L., Nagata, T., Kormelink, R., and De Avila, A. C. 1999. Increase of tospoviral diversity in Brazil with the identification of two new Tospovirus species, one from chrysanthemum and one from zucchini. Phytopathology 89:823-830.

2. Bucher, E., Sijen, T., de Haan, P., Goldbach, R., and Prins, M. 2003. Negative-strand Tospoviruses carry a gene for gene silencing at analogous genomic positions. J. Virol. 77:1329-1336.
3. Brown, J. K., and Bird, J. 1992. Whitefly transmitted geminiviruses in the americas and the Caribbean Basin: Past and present. Plant Dis. 76:220-225.
4. Brown, J. K., Guerrero, J. C., Matheron, M., Olsen, M., and Idris, A. M. 2007. Widespread outbreak of Cucurbit yellow stunting disorder virus in melon, squash and watermelon crops in the Sonoran desert of Arizona and Sonora, Mexico. Plant Dis. 91:773.
5. Brown, J. K., Idris, A. M., Alteri, C., and Stenger, D.C. 2002. Emergence of a new cucurbit-infecting Begomovirus species capable of forming viable reassortants with related viruses in the Squash leaf curl virus Cluster. Phytopathology 92:734-742.
6. Cortez, I., Saaijer, J., Wongjkaew, K. S., Pereira, A. M., Goldbach, R., Peters, D., and Kormelink, R. 2001. Identification and characterization of a novel Tospovirus species using RT-PCR approach. Arch. Virol. 146:265-278.
7. De Avila, A. C., De Haan, P., Kormelink, D., O., Resende, R., Goldbach, R. W., and Peters, D. 1993. Classification of tospoviruses based on phylogeny of nucleoprotein gene sequences. J. Gen. Virol. 74:153-159. 8. Delgadillo, S. F., Garzon, T. J. A., and Vega, P. A. 1989. Cucurbit viruses in Mexico: a survey. Rev. Mex. Fitopatol. 7:136-139.
9. Fauquet, C. M., Mayo, M. A., Maniloff, J., Desselberger, U., and Ball, L. A. 2005. Virus taxonomy. Pages 712-716 in: Eighth Rep. Int. Committee Taxonomy of Viruses. Elsevier Academic Press, London.
10. Felsenstein, J. 1989. PHYLIP—phylogeny inference package (version 3.2). Cladistics 5(2):164-166.
11. Goldbach, R., and Peters, D. 1996. Molecular and biological aspects of tospoviruses. Pages 129-157 in: The Bunyaviridae. R. M. Elliott, ed. Plenum Press, New York & London.
12. Hassani-Mehraban, A., Saaijer, J., Peters, D., Goldbach, R., and Kormelink, R. 2005. A new tomato-infecting tospovirus from Iran. Phytopathology 95:852-858.
13. Jain, R. K., Pappu, H. R., Pappu, S. S., Krishna Reddy, M., and Vani, A. 1998. watermelon bud necrosis tospovirus is a distinct virus species belonging to serogroup IV. Arch. Virol. 143:1637-1644.
14. Kato, K., and Hanada, K. 2000. Characterization of the S RNA segment of Melon yellow spot virus. Jpn. J. Phytopathol. 66:252-254.
15. Moyer, J. W. 1999. Tospoviruses (Bunyaviridae). Pages 1803-1807 in: Encyclopedia of Virology. A. Granoff and R. G. Webster, eds. Academic Press, New York.
16. Mumford, R. A., Barker, I., and Wood, K. R. 1996. The biology of the tospoviruses. Ann. Appl. Biol. 128:159-183.
17. Nagata, T., Carvalho, K. R., Noronha, E. F., Sodre, R. D. A., Dutra, L S, Oliveira, P. A., Lovato, F. A., Resende, R. O., De Avila, A. C., and Inouya-Nagata, A. K. 2007. The lycoprotein gene of Chrysanthemum stem necrosis virus and Zucchini lethal chlorosis virus and molecular relationship with other tospoviruses. Virus Genes 35:785-793.
18. Nathanson, N., and Gonzàles-Scarano, F. 1999. Bunyaviridae, general features. Pages 204-212 in: Encyclopedia of Virology. A. Granoff and R. G. Webster, eds. Academic Press, New York.
19. Page, R. D. M. 1996. TreeView: an application to display phylogenetic trees on personal computers. Comput. Appl. Biosci. 12:357-358.
20. Pappu, H. R. 2008. Tomato spotted wilt virus (Bunyaviridae). Pages 133-138 in: Encyclopedia of Virology, Vol V, 3rd ed. B. W. J. Mahy and M. H. V. van Regenmortel, eds. Elsevier Ltd., Oxford.
21. Pappu, S. S., Bhat, A. I., Pappu, H. R., Deom, C. M., and Culbreath, A. K. 2000. Phylogenetic studies of tospoviruses (family Bunyaviridae) based on intergenic region sequences of small and medium genomic RNAs. Arch. Virol. 145:1035-1045.
22. Ramirez-Arredondo, J. A., Armenta-Cardens, I., Delgadillo-Sanchez, F., Rivera-Bustamante, R. F., and Garzon-Tiznado, J. A. 1995. Geminiviruses transmitted by whitefly (Bemisia tabaci) in crops of pepper and squash in Mayo Valley, Sonora, Mexico. Rev. Mex. Fitopatol. 13:100-105.
23. Roggero, P., Ciuffo, M., Vaira, A. M., Accotto, G. P., Masenga, V., and Milne, R. G. 2000. An ophiovirus isolated from lettuce with big-vein symptoms. Arch. Virol. 145:2629-2642.
24. Roggero, P., Ciuffo, M., Vaira, A. M., and Milne, R. G., 1998. Rapid purification of tospovirus nucleocapsids for antibody production and RNA analysis. Pages 25-28 in: Recent Progress in Tospovirus and Thrips Research. D. Peters and R. Goldbach, eds. Wageningen University, Wageningen, The Netherlands.
25. Sanger, F., Bicken, S., and Coulson, A. R. 1977. DNA sequencing with chain terminating inhibitors. Proc. Natl. Acad. Sci. USA 74:5463-5467.
26. Sherwood, J. L., German, T. L., Moyer, J. W., Ullman, D. E., and Whitfield, A. E. 2000. Tomato spotted wilt virus. Pages 1030-1031 in: Encyclopedia of Plant Pathology. O. C. Maloy and T. D. Murray, eds. John Wiley & Sons, New York.
27. Sin, S.-H., McNulty, B. C., Kennedy, G. G., and Moyer, J. W. 2005. Viral genetic determinants for thrips transmission of Tomato spotted wilt virus. Proc. Natl. Acad. Sci. USA 102:5168-5173.
28. Soellick, T. R., Uhrig, J. F., Bucher, G. L., Kellmann J. W., and Schreier, P. H.2000. The movement protein NSm of Tomato spotted wilt tospovirus (TSWV): RNA binding, interaction with the TSWV N protein, and identification of interacting plant proteins. Proc. Natl. Acad. Sci. USA 70:2373-2378.
29. Storms, M. M. H., Kormelink, R., Peters D., Van Lent, J. W. M., and Goldbach, R. W. 1995. The nonstructural protein of Tomato spotted wilt virus induces tubular structures in plant and insect cells. Virology 214:485-493.
30. Strimmer, K., and von Heaselen, A.1996. Quartet puzzling: a quartet maximum likelihood method for reconstructing tree topologies. Mol. Biol. Evol. 13:964-969.
31. Takeda, A., Sugiyama, K., Nagano, H., Mori, M., Kaido, M., Mise, K., Tsuda, S., and Okumo, T. 2002. Identification of a novel RNA silencing suppressor, NSs protein of Tomato spotted wilt virus. FEBS Lett. 532:75-79.
32. Thompson, J. D., Higgins, D. G., and Gibson, T. J. 1994. Clustal W: improving the sensitivity of progressive multiple sequence alignment through sequence weighting, position-specific gap penalties and weight matrix choice. Nucleic Acids Res. 22:4673-4680.
33. Tsompana, M., Abad, J., Purugganan M., and Moyer, J. W. 2005. The molecular population genetics of the Tomato spotted wilt virus (TSWV) genome. Mol. Ecol. 14:53-66.
34. Tsompana, M., and Moyer, J. W. 2008. Tospoviruses. Pages 157-163 in: Encyclopedia of Virology, Vol. V, 3rd ed. B. W. J. Mahy and M. H. V. van Regenmortel, eds. Elsevier Ltd., Oxford.
35. Turina, M., Ciuffo, M., Lenzi, R., Rostagno, L., Mela, E., and Palmano. S. 2006. Characterization of four species belonging to the family Potyviridae isolated from *Ranunculus asiaticus*. Phytopathology 96:560-566.
36. Turina, M., Desvoyes, B., and Scholthof, K.-B. 2000. A gene cluster encoded by Panicum mosaic virus is associated with virus movement. Virology 266:120-128.
37. Turina, M., Ricker, M. D., Lenzi, R., Masenga, V., and Ciuffo, M. 2007. A severe disease of tomato in the Culiacan Area (Sinaloa, Mexico) is caused by a new picorna-like viral species. Plant Dis. 91:932-941.
38. van Knippernberg, I., Goldbach, R., and Kormelink, R. 2005. Tomato spotted wilt virus Segment mRNA have overlapping 3'-end containing a predicted stem loop structure and conserved sequence motif. Virus Res. 110:125-131.
39. Whitfield, A. E., Ullman, D. E., and German, T. L. 2005. *Tospovirus*-thrips interactions. Annu. Rev. Phytopathol. 43:459-89.
40. Yeh, S.-D., Lin, Y.-C., Cheng Y. H., Jih, C.-L., Chen, M.-J., and Chen, C.-C. 1992. Identification of tomato spotted wilt-like virus on watermelon in Taiwan. Plant Dis. 76:835-840.
41. Zucker, M. 2003. Mfold web server for nucleic acid folding and hybridization prediction. Nucleic Acids Res. 31:3406-3415.
42. Altschul, S. F., Gish, W., Miller, W., Myers, E. W., Lipman, D. J. (1990) "Basic local alignment search tool," J. Mol. Biol., 215:403-410.
43. Altschul, S. F., Madden, T. L., Schaffer, A. A., Zhang, J., Zhang, Z., Miller, W., Lipman, D. J. (1997) "Gapped BLAST and PSI-BLAST: A new generation of protein database search programs," Nucl. Acids Res., 25, 3389-3402.
44. Ausubel, F. M., Brent, R., Kingston, R. E., Moore, D. D., Seidman, J. G., Smith, J. A., Struhl, K. eds. (1998) Current Protocols in Molecular Biology, V. B. Chanda, series ed. New York: John Wiley & Sons.
45. Barany, F. (1991) "Genetic disease detection and DNA amplification using cloned thermostable ligase," Proc. Natl. Acad. Sci. USA, 88:189-193.
46. Boom, R., Sol, C. J. A., Salimans, M. M. M., Jansen, C. L., Wertheim-van Dillen, P. M. E., Noordaa, van der J. (1990) "Rapid and simple method for purification of nucleic acids," J. Clin. Microbiol., 28:495-503.
47. Chomczynski, P., Sacchi, N. (1987) "Single-step method of RNA isolation by acid guanidinium thiocyanate-phenol-chloroform extraction," Anal. Bio. 162:156-159.
48. Clark, M. F., Adams A. N. (1977) "Characteristics of the microplate method of enzyme-linked immunosorbent assay for the detection plant viruses," J. Gen. Virol. 34:475-483.
49. Coligan, J. E., Kruisbeek, A. M., Margulies, D. H., Shevach, E. M. Strober, W. (Eds.) (1997) Current Protocols in Immunology, John Wiley & Sons Inc. Baltimore.
50. Compton, J. (1991) "Nucleic acid sequence-based amplification," Nature 1991, 350:91-92.
51. Devereux, J., Haeberli, P., Smithies, O. (1984) "A comprehensive set of sequence
52. Dijkstra, J., de Jager, C. (Eds.) (1998) Practical Plant Virology—Protocols and Exercises, Springer
53. Duffus, J. E., Liu, H. Y., Wisler, G. C. (1996) "Tomato infectious chlorosis virus—a new clostero-like virus transmitted by *Trialeurodes vaporariorum*," European Journal of Plant Pathology, 102(3):219-226.
54. Felsenstein, J. 1989. PHYLIP—Phylogeny Inference Package (Version 3.2). Cladistics 5:164-166.
55. Guatelli, J. C., Whitfield, K. M., Kwoh, D. Y., Barringer, K. J., Richman, D. D., Gingeras, T. R. (1990) "Isothermal, in vitro amplification of nucleic acids by a mutienzyme reaction modeled after retroviral replication," Proc. Natl. Acad. Sci. USA 87:1874-1878.
56. Hagiwara, K., Ichiki, T. U., Ogawa, Y., Omura, T., Tsuda, S. (2002) "A single amino acid substitution in 126-kDa protein of Pepper mild mottle virus associates with symptom attenuation in pepper; the complete nucleotide sequence of an attenuated strain, C-1421," Arch. Virol., 147:833-340.
57. Harlow, E. and Lane, D. (1988) Antibodies: A Laboratory Manual, Cold Spring Harbor Laboratory, Cold Spring Harbor, N.Y.
58. Hirata, H., Lu, X., Yamaji, Y., Kagiwada, S., Ugaki, M. Namba, S. (2003) "A single silent substitution in the genome of Apple stem grooving virus causes symptom attenuation," J. Gen. Virol., 84:2579-2583.
59. Jacobs M. V., Snijders P. J., van der Brule A. J. (1997) "A general primer (GP5+/GP6+)-mediated PCR-enzyme immunoassay method for rapid detection of 14 high-risk and 8 low-risk human papillomavirus genotypes in cervical scrapings," J. Clin. Microbiol., 35:791-795.
60. Katz, E., Eksteen, R., Schoenmakers, P., Miller, N. (eds.) (1998) Handbook of HPLC, Marcel Dekker, New York.
61. Kinter, M., Sherman, N. E. (2000) "Protein Sequencing and Identification Using Tandem Mass Spectrometry," Wiley Interscience.
62. Koonin, E. V. (1991) "The phylogeny of RNA-dependent RNA polymerases of positive-strand RNA viruses," J. Gen. Virol., 72:2197-2206.
63. Kwoh, D. Y., Davis, G. R., Whitefield, K. M., Chappelle, H. L., DiMichele, L. J., Gingeras, T. R. (1989) "Transcription-Based Amplification System and Detection of Amplified Human Immunodeficiency Virus Type 1 with a Bead-Based Sandwich Hybridization Format," Proc. Natl. Acad. Sci. USA, 86:1173-1177.
64. Laemmli, U. K. (1970) "Cleavage of structural proteins during the assembly of the head of bacteriophage T4," Nature, 227:680-685.
65. Lerner, R. A., Kang, A. S., Bain, J. D., Burton, D. R., Barbas, C. F. (1992) "Antibodies without immunization," Science, 258:1313-1314.
66. Lizardi, P. M., Guerra, C. E., Lomeli, H., Tussie-Luna, I., Kramer, F. R. (1988) "Exponential amplification of recombinant RNA hybridization probes," Biotechnology, 6:1197-1202.
67. Lowman, H. B., Bass, S. H., Simpson, N., Wells, J. A. (1991) "Selecting high-affinity binding proteins by monovalent phage display," Biochem., 30(45):10832-10838.
68. Lu, X., Hirata, H., Yamaji, Y., Ugaki, M., Namaba, S. (2001) "Random mutagenesis in a plant viral genome using a DNA repair-deficient mutator *Escherichia coli* strain," J. Virol. Methods., 94:37-43.
69. Marks, J. D., Hoogenboom, H. R., Griffiths, A. D., Winter, G. (1992a) "Molecular evolution of proteins on filamentous phage," Journal of Biological Chemistry, 267:16007-16010.
70. Marks, J. D., Griffiths, A. D., Malmqvist, M., Clackson, T. P., Bye, J. M. Winter, G. (1992b). "Bypassing immunization: building high affinity human antibodies by chain shuffling," Biotechnology, 10:779:783.
71. Meinkoth J., Wahl G. (1984) "Hybridization of nucleic acids immobilized on solid supports," Anal. Biochem., 138(2):267-284.
72. Mullis, K. B., Faloona, F. A. (1987) "Specific synthesis of DNA in vitro via a polymerasecatalyzed chain reaction," Meth. Enzymol., 155:335-350.

73. Pierik, R. L. M. (1999) In vitro Culture of Higher Plants, 4th edition, 360 pages, ISBN: 0-7923-5267-X.
74. Rose, N., DeMacrio, E., Fahey, J., Friedman, H., Penn, G. (1997) Manual of Clinical Laboratory Immunology. American Soc. Microbiology Press, Washington, D.C.
75. Sambrook, J., Russell D. W., Sambrook, J. (2001) Molecular Cloning: a Laboratory Manual, Cold Spring Harbor Laboratory Press, Plainview, N.Y.
76. Sanger, F., Nicklen, S., Coulson, A. R. (1977) "DNA sequencing with chain-terminating inhibitors," Proc. Natl. Acad. Sci. U.S.A., 74:5463-5467.
77. Schagger H., von Jagow, G. (1987) "Tricine-sodium dodecyl sulfate-polyacrylamide gel electrophoresis for the separation of proteins in the range from 1 to 100 kDa," Analytical Biochemistry, 166:368-379.
78. Smith, L. M., Sanders, J. Z., Kaiser, R. J., Hughs, P., Dodd, C., Connell, C. R., Heins, C., Kent, S. B. H., Hood, L. E. (1986) "Fluorescent detection in automated DNA sequence analysis," Nature, 321:673-681.
79. Swofford, D. L. (2000) PAUP*: phylogenetic analysis using parsimony (* and other methods). 4th edition. Sinauer Associates, Sunderland, Mass.
80. Takeshita, M., Suzuki, M., Takanami, Y. (2001) "Combination of amino acids in the 3a protein and the coat protein of Cucumber mosaic virus determines symptom expression and viral spread in bottle gourd," Arch. Virol., 146: 697-711.
81. Thompson, J. D., Gibson, T. J., Plewniak, F., Jeanmougin, F., Higgins, D. G. (1997) "The ClustalX windows interface: flexible strategies for multiple sequence alignment aided by quality analysis tools," Nucleic Acids Research, 24:4876-4882.
82. Thompson, J. R., Perry, K. L., De Jong, W. (2004a) "A new potato virus in a new lineage of picorna-like viruses," Arch. Virol., 149:2141-2154.
83. Thompson, J. R., Perry, K. L., De Jong, W. (2004b) "The characterization of a new picorna-like virus infecting tomato," Abstract Book of the 23 rd Annual Meeting of the American Society for Virology, Montreal, Canada, July 2004.
84. Tijssen, P. (1993) Laboratory Techniques in Biochemistry and Molecular Biology—Hybridization with Nucleic Acid Probes, Part I, Chapter 2 "Overview of principles of hybridization and the strategy of nucleic acid probe assays," Elsevier. New York.
85. Van den Brule, A. J. C., Pol, R., Fransen-Daalmeijer, N., Schouls, L. M., Meijer, C. J. L. M., Snijders, P. J. F. (2002) "GP5+/6+PCR followed by Reverse Line Blot Analysis Enables Rapid and High-Throughput Identification of Human Papillomavirus Genotypes," J. Clin. Microbiol., 40:779-787.
86. Vela, C., Cambra, M., Cortes, E., Moreno, P., Miguet, J. G., Pérez de San Román, C., Sanz, A. (1986) "Production and characterization of monoclonal antibodies specific for citrus tristeza virus and their use for diagnosis," J. Gen. Virol., 67:91-96.
87. Walker, G. T., Fraiser, M. S., Schram, J. L., Little, M. C., Nadeau, J. G., Malinowski, D. P. (1992) "Strand displacement amplification—an isothermal, in vitro DNA amplification technique," Nucleic Acids Res., 20:1691-1696.
88. Walker, J. M. (2004) PCR Protocols on CD. Humana Press.
89. Wisler, G. C., Li, R. H., Liu, H. Y., Lowry, D. S., Duffus, J. E. (1998) "Tomato chlorosis virus: a new whitefly-transmitted, phloem-limited, bipartite closterovirus of tomato," Phytopathology, 88(5):402-409.
90. Young R. A., Davis, R. W. (1983) "Efficient isolation of genes using antibody probes," Proc. Natl. Acad. Sci. U.S.A., 80:1194-1198.
91. Beachy et al. "Coat Protein-Mediated Resistance Against Virus Infection," 1990, Annu. Rev. Phytopathology 28:451-74,
92. Cuozzo et al., "Viral Protection in Transgenic Tobacco Plants Expressing the Cucumber Mosaic Virus Coat Protein or its Antisense RNA," 1988, BioTechnology 6:549-57
93. Hemenway et al., "Analysis of the Mechanism of Protection in Transgenic Plants Expressing the Potato Virus X Coat Protein or its Antisense RNA," 1988, The EMBO J. 7(5):1273-80
94. Kawchuk, et al., "Resistance in Transgenic Potato Expressing the Potato Leafroll Virus Coat Protein Gene," 1990, Molecular Plant-Microbe Interactions, 3(5):301-07
95. Ling et al., "Protection Against Detrimental Effects of Potyvirus Infection in Transgenic Tobacco Plants Expressing the Papaya Ringspot Virus Coat Protein," 1991, BioTechnology 9:752-58
96. Abel et al., "Delay of Disease Development in Transgenic Plants that Express the Tobacco Mosaic Virus Coat Protein," Science 232:738-43 (1986)
97. Quemada et al., "Expression of Coat Protein Gene from Cucumber Mosaic Virus Strain C in Tobacco: Protection Against Infections by CMV Strains Transmitted Mechanically or by Aphids," Phytopathology 81(7):794-802 (1991).
98. Tumer, N. E. et al., "Expression of Alfalfa Mosaic Virus Coat Protein Gene Confers Cross-Protection in Transgenic Tobacco and Tomato Plants," The EMBO J. 6:1181-88 (1987).
99. vanDun, C. M. P. et al., "Transgenic Tobacco Expressing Tobacco Streak Virus or Mutated Alfalfa Mosaic Virus Coat Protein Does Not Cross-Protect Against Alfalfa Mosaic Virus Infection," Virology 164:388-89 (1988).
100. Adkins, Scott et al., "Tospovirus (Family Bunyaviridae, Genus Tospovirus)", University of Florida IFAS Extension Fact Sheet PP-212, 5 pages (October 2205).
101. Chiemsombat et al., "Biological and molecular characterization of tospoviruses in Thailand Pissawan", Arch Virol. 153:571-577 (2008)

The invention claimed is:

1. A method of breeding a *Cucurbita pepo* plant resistant to Melon Severe Mosaic Virus (MeSMV), wherein the method comprises the steps of:
   (i) providing a first cucurbit plant, said first cucurbit plant being resistant to MeSMV, wherein the first cucurbit plant is a *Cucurbita moschata* plant or a *Cucurbita maxima* plant;
   (ii) crossing the cucurbit plant provided in step (i) with a second cucurbit plant to produce progeny plants, wherein the second cucurbit plant is a *Cucurbita pepo* plant;
   (iii) when the resistance is due to dominant or partially dominant locus/loci, selecting one or more progeny plants that are resistant to MeSMV from the progeny of step (ii); when the resistance is due to recessive locus/loci, backcrossing the progeny of step (ii) to the second cucurbit plant to create a backcrossed progeny, or selfing the progeny of step (ii) to create a selfed progeny, and selecting one or more progeny plants that are resistant to MeSMV from the backcrossed progeny or the selfed progeny;
   (iv) backcrossing the selected progeny plants of step (iii) or selfed offspring thereof with the second cucurbit plant of step (ii) to produce backcross progeny plants;
   (v) when the resistance is due to dominant or partially dominant locus/loci, selecting for backcross progeny plants that are resistant to MeSMV from the backcross progeny plants of step (iv); when the resistance is due to recessive locus/loci, backcrossing the selected, backcrossed progeny of step (iv) to the second cucurbit plant to create a further backcrossed progeny, or selfing the backcrossed progeny of step (iv) to create a further selfed progeny, and selecting one or more progeny plants that are resistant to MeSMV from the backcrossed progeny or the selfed progeny; and
   (vi) repeating steps (iv) and (v) three or more times in succession to produce selected fourth or higher backcross progeny plants that are resistant to MeSMV.

2. The method of claim 1, wherein the *C. moschata* plant is 'Menian Rajada Seca', 'Nigerian', 'Native squash' (Ns), 'Butterfly', Mexican 'land race' (Ws), Shimer Kobocha (Sk), or a hybrid thereof.

3. The method of claim 1, wherein the second cucurbit plant is a plant having one or more desired physiological and morphological characteristics.

4. The method of claim 1, wherein the *C. pepo* plant is Vigne squash variety, Zucchini Elite, Hurakon, Linda, Citlali, SSXP 4511, Golden Arrow, SSXP 4506, Huaso, SSXP 4507, Arte, SSXP 4512, or hybrid thereof.

5. A method of breeding a *Cucurbita pepo* plant resistant to Melon Severe Mosaic Virus (MeSMV), wherein the method comprises the steps of:

(i) providing a first *Cucurbita pepo* plant resistant to MeSMV, wherein the first *Cucurbita pepo* plant is produced by the method of claim 1;

(ii) crossing the first *Cucurbita pepo* plant provided in step (i) with a second *Cucurbita pepo* plant to produce progeny plants;

(iii) when the resistance is due to dominant or partially dominant locus/loci, selecting one or more progeny plants that are resistant to MeSMV from the progeny of step (ii); when the resistance is due to recessive locus/loci, backcrossing the progeny of step (ii) to the second *Cucurbita pepo* plant to create a backcrossed progeny, or selfing the progeny of step (ii) to create a selfed progeny, and selecting one or more progeny plants that are resistant to MeSMV from the backcrossed progeny or the selfed progeny;

(iv) backcrossing the selected progeny plants of step (iii) or selfed offspring thereof with the second *Cucurbita pepo* plant of step (ii) to produce backcross progeny plants;

(v) when the resistance is due to dominant or partially dominant locus/loci, selecting for backcross progeny plants that are resistant to MeSMV from the backcross progeny plants of step (iv); when the resistance is due to recessive locus/loci, backcrossing the selected, backcrossed progeny of step (iv) to the second *Cucurbita pepo* plant to create a further backcrossed progeny, or selfing the backcrossed progeny of step (iv) to create a further selfed progeny, and selecting one or more progeny plants that are resistant to MeSMV from the backcrossed progeny or the selfed progeny; and (vi) repeating steps (iv) and (v) three or more times in succession to produce selected fourth or higher backcross progeny plants that are resistant to MeSMV.

* * * * *